United States Patent [19]
Dax et al.

[11] Patent Number: 6,140,354
[45] Date of Patent: Oct. 31, 2000

[54] N-SUBSTITUTED AMINOTETRALINS AS LIGANDS FOR THE NEUROPEPTIDE Y Y5 RECEPTOR USEFUL IN THE TREATMENT OF OBESITY AND OTHER DISORDERS

[75] Inventors: Scott L. Dax, Landenberg, Pa.; Timothy W. Lovenberg, San Diego, Calif.; James McNally, Souderton, Pa.; Allen B. Reitz, Lansdale, Pa.; Mark A. Youngman, Warminster, Pa.

[73] Assignee: Ortho-McNeil Pharmaceutical, Inc., Raritan, N.J.

[21] Appl. No.: 09/290,651

[22] Filed: Apr. 12, 1999

Related U.S. Application Data
[60] Provisional application No. 60/083,415, Apr. 29, 1998.

[51] Int. Cl.[7] .................. A61K 31/34; A61K 31/505; C07D 211/82; C07D 233/64; C07D 307/08
[52] U.S. Cl. .................. 514/357; 514/269; 514/396; 514/438; 514/471; 544/298; 546/333; 548/340.1; 549/75; 549/491
[58] Field of Search .................. 514/269, 275, 514/344, 357, 396, 447, 471, 602, 603, 604; 544/298; 546/285, 289, 333; 548/326.5, 327.1, 340.1; 549/61, 75, 474, 481, 491; 564/80, 90, 92

[56] References Cited

U.S. PATENT DOCUMENTS
5,026,857  6/1991  Schohe et al. .

FOREIGN PATENT DOCUMENTS
0 270 947 A2  11/1987  European Pat. Off. .
97/19682       5/1997   WIPO .
97/20823      12/1997   WIPO .

*Primary Examiner*—Joseph McKane
*Assistant Examiner*—Taofiq A. Solola
*Attorney, Agent, or Firm*—Ralph R. Palo

[57] ABSTRACT

β-Aminotetralin derivatives of the formula:

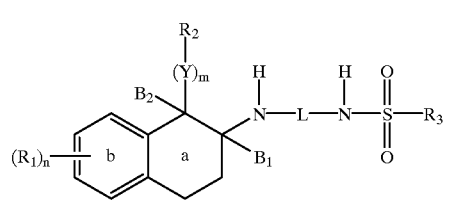

(1)

which are ligands for the neuropeptide Y Y5 (NPY5) receptor, methods of preparation and pharmaceutical compositions containing a β-aminotetralin derivative as the active ingredient are described. The β-aminotetralins are useful in the treatment of disorders and diseases associated with NPY receptor subtype Y5.

22 Claims, No Drawings

N-SUBSTITUTED AMINOTETRALINS AS LIGANDS FOR THE NEUROPEPTIDE Y Y5 RECEPTOR USEFUL IN THE TREATMENT OF OBESITY AND OTHER DISORDERS

This application is based on provisional application Ser. No. 60/083,415, filed Apr. 29, 1998.

FIELD OF THE INVENTION

This invention relates to a series of β-aminotetralin derivatives, pharmaceutical compositions containing them and intermediates used in their preparation. The compounds of the invention are ligands for the neuropeptide Y Y5 (NPY5) receptor, a receptor which is associated with a number of central nervous system disorders and affective conditions. In addition, many of the compounds of the invention reduce food consumption in a rodent model of feeding.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein which is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. *Nature* 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic α-helix joined by a characteristic PP-fold (Vladimir, S. et. Al. *Biochemistry* 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. *Ann. NY Acad. Sci.* 1990, 611, 7; Larhammar, D. et. al. *J. Biol. Chem.* 1992, 267, 10935; Wahlestedt, C. et. al. *Regul. Pept.* 1986, 13, 307; Fuhlendorff, J. U. et. al. *Proc. Natl. Acad. Sci. USA* 1990, 87, 182; Grundemar, L. et. al. *J. Pharmacol. Exp. Ther.* 1991, 258, 633; Laburthe, M. et. al. *Endocrinology* 1986, 118, 1910; Castan, I. et. al. *Endocrinology* 1992, 131, 1970; Gerald, C. et. al. *Nature* 1996, 382, 168; Weinberg, D. H. et. al. *Journal of Biological Chemistry* 1996, 271, 16435; Gehlert, D. et. al. *Current Pharmaceutical Design* 1995, 1, 295; Lundberg, J. M. et. al. *Trends in Pharmaceutical Sciences* 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. *Nature* 1996, 382,168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. *Psychopharmacology* 1989, 98, 524; Heilig, M. et. al. *Reg. Peptides* 1992, 41, 61; Heilig, M. et. al. *Neuropsycho-pharmacology* 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. *Journal of Neurochemistry* 1992, 59, 73), and rats treated with tricyclic antidepressants display significant increases of NPY relative to a control group (Heilig, M. et.

al. *European Journal of Pharmacology* 1988, 147, 465). These findings suggest that an inadequate NPY response may play a role in some depressive illnesses, and that compounds that regulate the NPY-ergic system may be useful for the treatment of depression.

Neuropeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of eating disorders such as obesity, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be attributed to antagonism of the Y1 receptor.

Several landmark studies strongly suggest that an "atypical Y1" receptor and/or the Y5 receptor, rather than the classic Y1 receptor, is responsible for invoking NPY-stimulated food consumption in animals. It has been shown that the NPY fragment $NPY_{2\text{-}36}$ is a potent inducer of feeding despite poor binding at the classic Y1 receptor (Stanley, B. G. et. al. *Peptides* 1992, 13, 581). Conversely, a potent and selective Y1 agonist has been reported to be inactive at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. *Nature* 1996, 382, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

Also pertinent to the invention described herein, are disclosures of arylsulfonamides that act as Y5 antagonists. In PCT WO 97/19682, aryl sulfonamides and sulfamides derived from arylalkylamines are described as Y5 antagonists and are reported to reduce food consumption in animals. In PCT WO 97/20820, PCT WO 97/20822 and PCT WO 97/20823, sulfonamides containing heterocyclic systems such as quinazolin-2,4-diazirines, are likewise claimed as Y5 antagonists and reported to reduce feeding. There is no disclosure in any of these publications of an α-substituted β-aminotetralin. The N-substituted aminotetralins described in this application are novel molecular entities that may have binding motifs that are different than these and other Y5 ligands that have been disclosed in patent applications or publications, and yet bind to a similar region of the Y5 receptor.

SUMMARY OF THE INVENTION

The present invention is related to compounds of formula 1

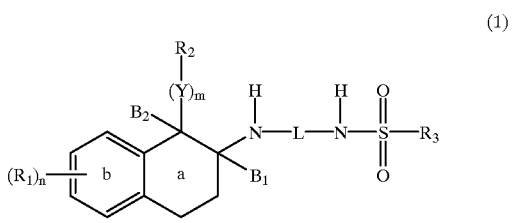

(1)

$R_1$ is independently selected from the group consisting of hydrogen; hydroxy; halo; $C_{1-8}$alkyl; substituted $C_{1-8}$ alkyl wherein the substituent is selected from halo, such as chloro, bromo, and fluoro; $C_{1-8}$alkoxy; substituted Cl, alkoxy wherein the substituent is selected from halo, such as chloro, bromo, fluoro and iodo; trifluoroalkyl; $C_{1-8}$alkylthio and substituted $C_{1-8}$alkylthio wherein the substituent is selected from halo, such as chloro, bromo, fluoro and iodo, trifluoroalkyl and $C_{1-8}$alkoxy; $C_{3-6}$cycloalkyl; $C_{3-8}$cycloalkoxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$B_2$ is selected from the group consisting of hydrogen; $C_{1-5}$alkyl; substituted $C_{1-5}$alkyl wherein the substituent is halogen;

$B_2$ may have either a cis- or trans-stereochemical orientation with respect to $B_1$; both enantiomers of each diastereomeric set are part of the present invention;

Y is methylene m 0–3

$R_2$ is selected from the group consisting of hydrogen; hydroxy; $C_{1-6}$alkyl; $C_{1-6}$alkenyl; halo, such as fluoro and chloro; $C_{3-7}$cycloalkyl; phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; naphthyl; phenoxy; substituted phenoxy wherein the substituent is selected from halo, $C_{1-6}$alkyl, $C_{1-6}$alkoxy, trifluoro$C_{1-6}$alkyl, cyano and nitro; phenylthio and substituted phenylthio wherein the substituent is selected from halo, $C_{1-6}$alkyl, nitro and amino; a heteroaryl group such as pyridyl, pyrimidyl, furyl, thienyl, and imidazolyl; substituted heteroaryl wherein the substituent is selected from $C_{1-6}$alkyl and halo; and heterocycloalkyl such as pyrrolidino or piperidino;

$B_1$ is selected from the group consisting of hydrogen; $C_{1-5}$alkyl; substituted $C_{1-5}$alkyl wherein the substituent is halo;

$B_1$ may have either a cis- or trans-stereochemical orientation with respect to $B_2$; both enantiomers of each diastereomeric set are part of this invention.

L is selected from the group consisting of
$C_{1-8}$alkylene; $C_{2-10}$alkenylene; $C_{2-10}$alkynylene;
$C_{1-4}$alkylene$C_{3-7}$cycloalkylene; $C_{1-6}$alkylene$C_{3-7}$cycloalkyl$C_{1-6}$alkylene;
$C_{2-4}$alkenylene$C_{3-7}$cycloalkyl$C_{2-4}$alkenylene;
$C_{2-4}$alkynylene$C_{3-7}$cycloalkyl$C_{2-4}$alkynylene;
$C_{1-4}$alkylenearyl$C_{1-4}$alkylene; and
$C_{2-4}$alkenylenearyl$C_{2-4}$alkenylene;

$R_3$ is selected from $C_{1-8}$alkyl; substituted $C_{1-8}$alkyl wherein the substituent is selected from alkoxy and halo; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

and enantiomers, diastereomers, and pharmaceutically acceptable salts thereof.

As used herein unless otherwise noted the terms "alkyl" and "alkoxy" whether used alone or as part of a substituent group, include straight and branched chains having 1–8 carbon atoms. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. The term "aryl" is intended to include phenyl and naphthyl. The term "halo", unless otherwise indicated, includes bromo, chloro, fluoro and iodo. The term "cycloalkyl" is intended to include cycloalkyl groups having 3–7 carbon atoms. With reference to substituents, the term "independently" means that when more than one of such substituent is possible, such substituents may be the same or different from each other.

Those compounds of the present invention which contain a basic moiety can be converted to the corresponding acid addition salts by techniques known to those skilled in the art. Suitable acids which can be employed for this purpose include hydrochloric, hydrobromic, hydriodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. In general, the acid addition salts can be prepared by reacting the free base of compounds of formula 1 with the acid and isolating the salt.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

For the treatment of disorders of the central nervous system, the pharmaceutical compositions described herein will typically contain from 1 to about 1000 mg of the active ingredient per dosage; one or more doses per day may be administered. Determination of optimum doses and frequency of dosing for a particular disease state or disorder is within the experimental capabilities of those knowledgeable in the treatment of central nervous system disorders. The preferred dose range is 1–100 mg/kg.

As modulators of the NPY5 receptor, the compounds of Formula 1 are useful for treating feeding disorders such as obesity, anorexia nervosa and bulimia nervosa, and abnormal conditions such as epilepsy, depression, anxiety and sexual/reproductive disorders in which modulation of the NPY5 receptor may be useful. The compounds compete with the endogenous ligands NPY and PYY and possibly non-endogenous ligands, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH).

The present invention comprises pharmaceutical compositions containing one or more of the compounds of Formula 1. Amide precursors to compounds of Formula 1 are also novel and are considered to be part of the invention.

Examples of particularly preferred compounds of formula 1 include:

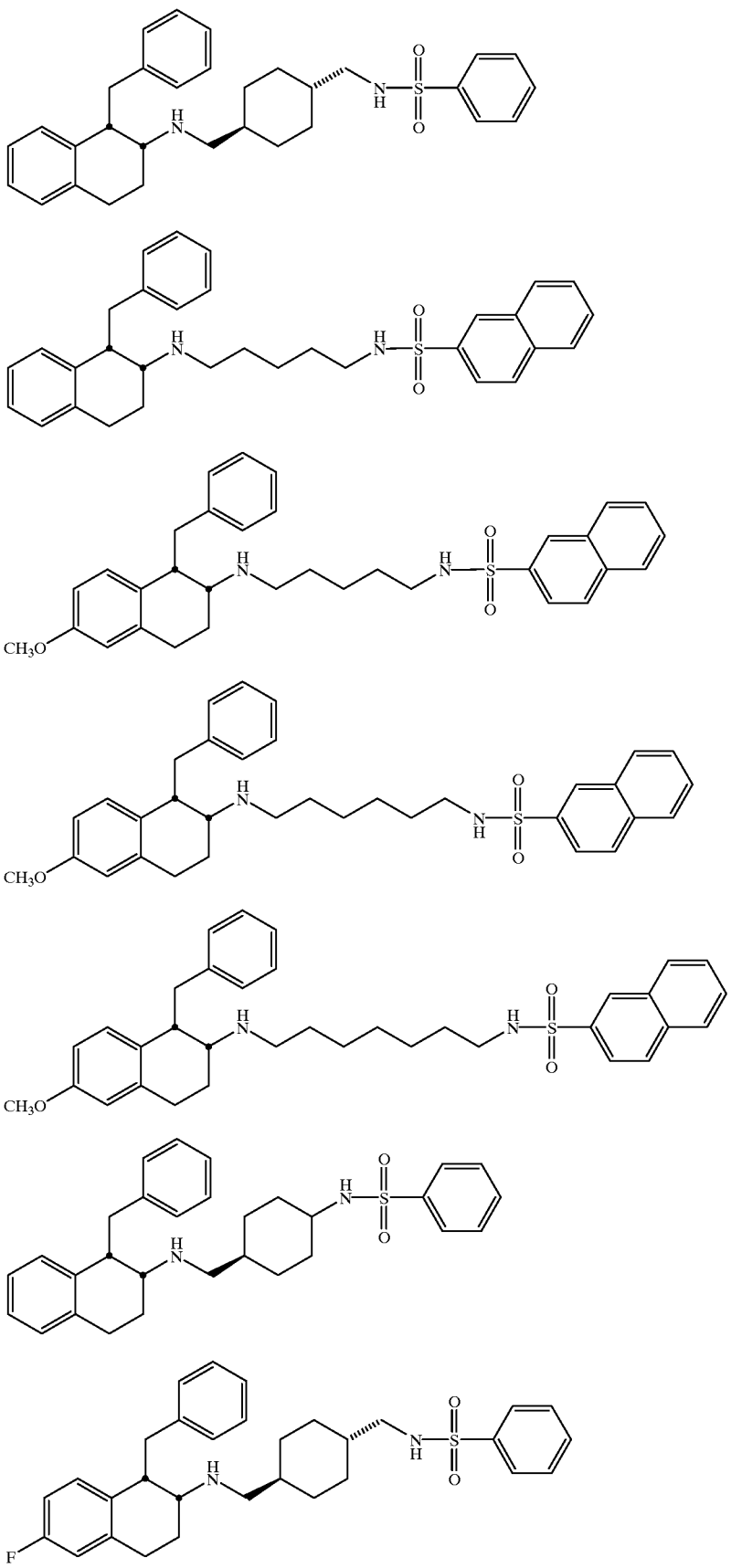

-continued
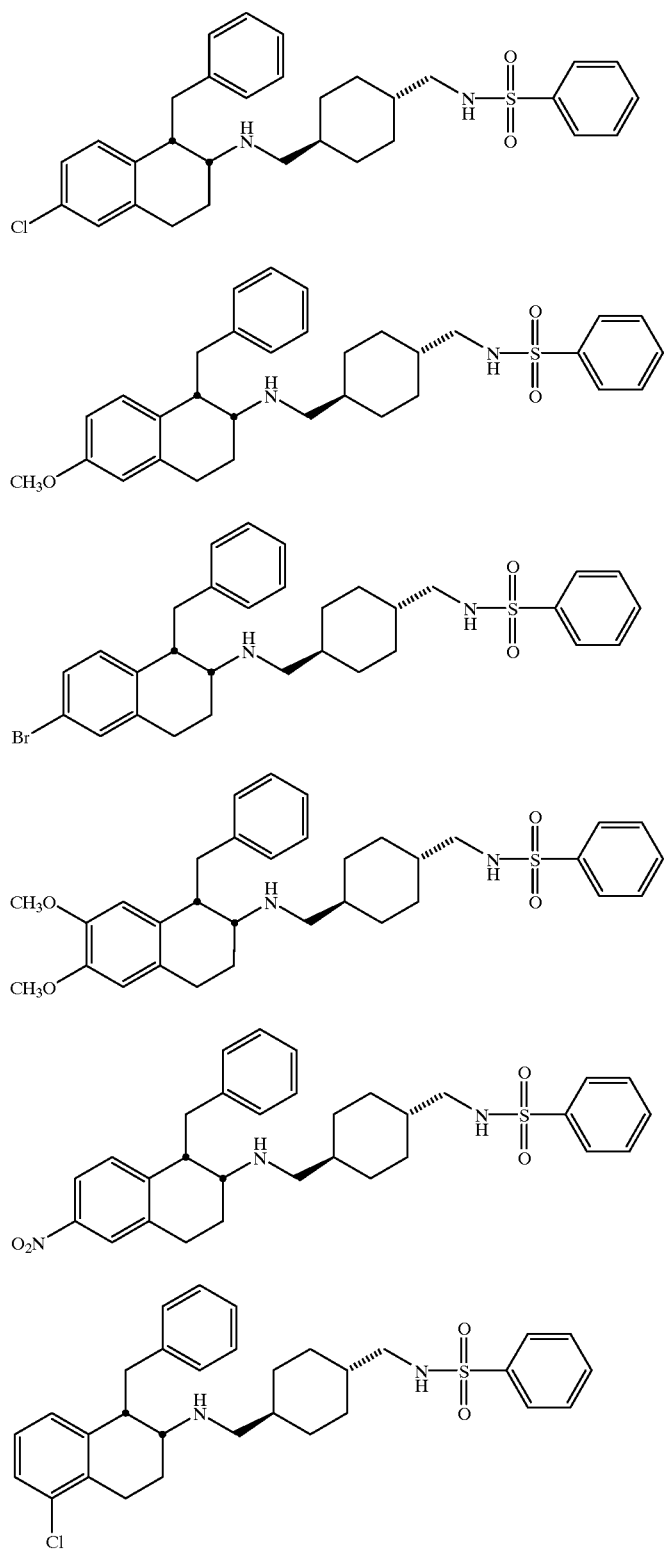

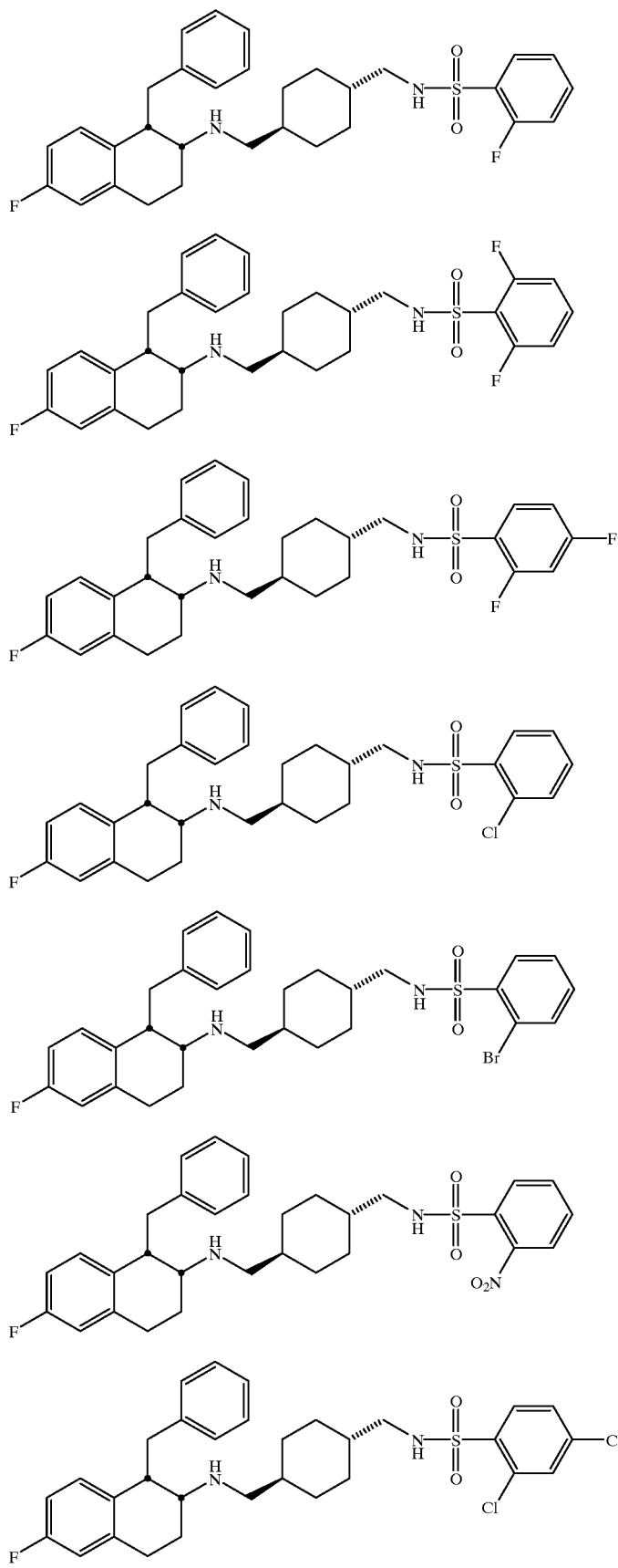

-continued
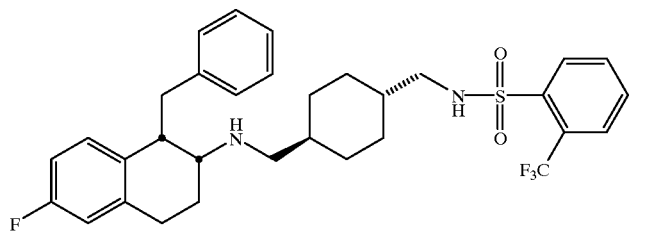
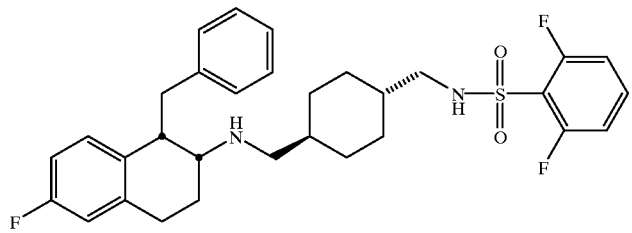
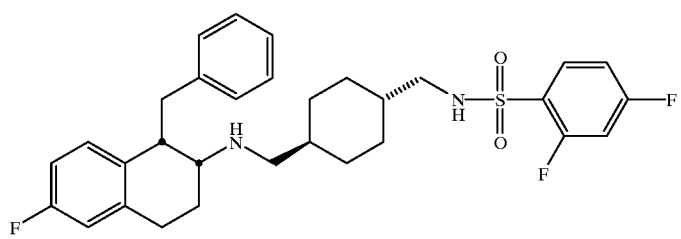
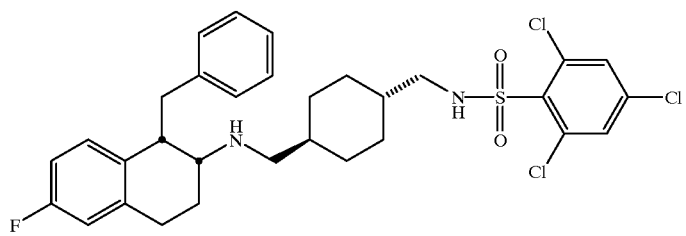
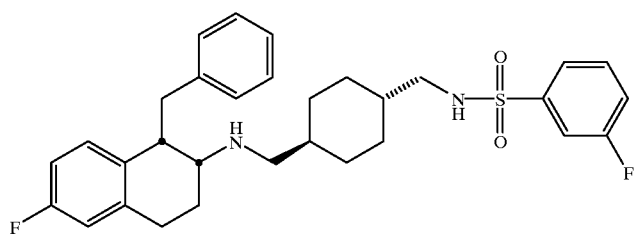
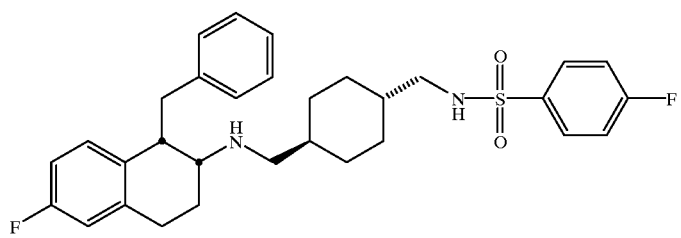
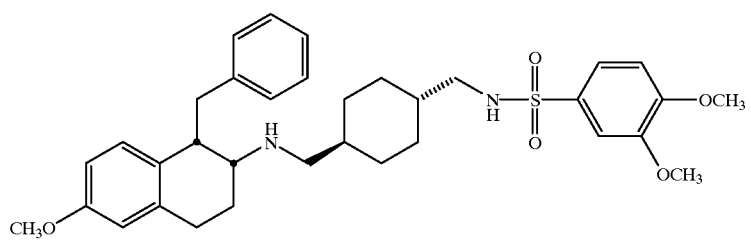

-continued
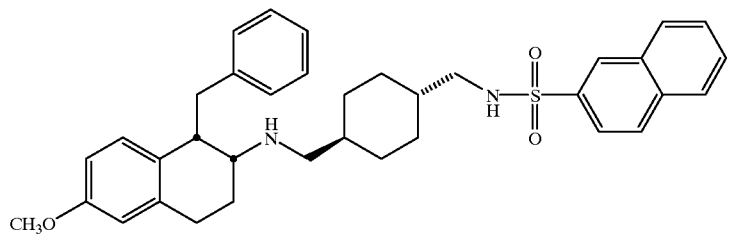
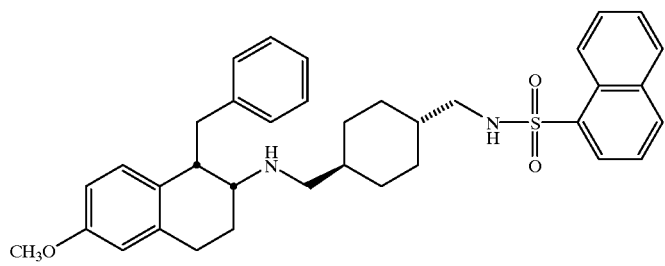
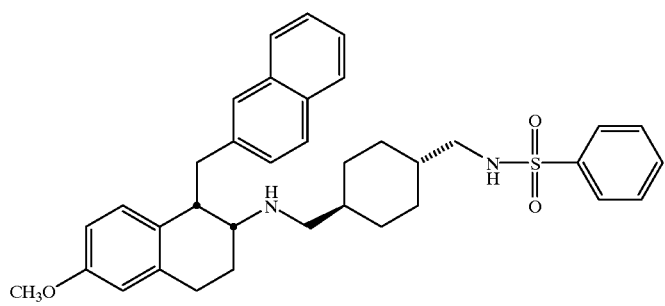
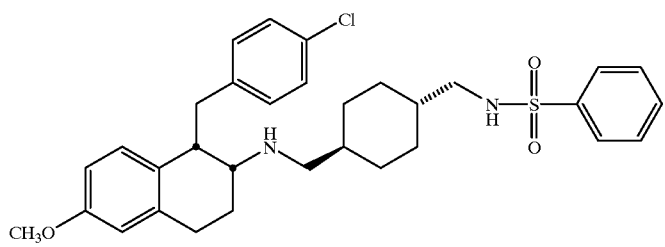
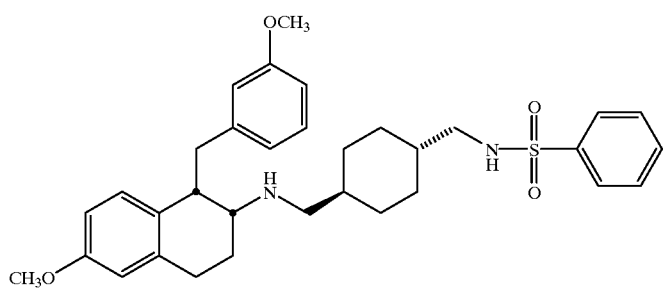
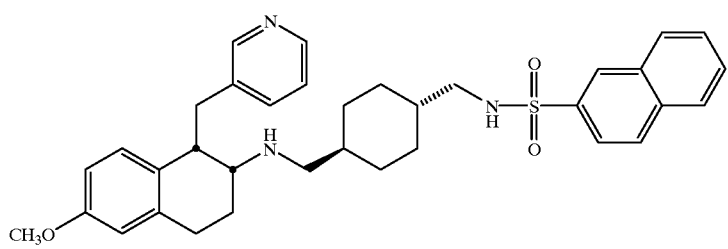

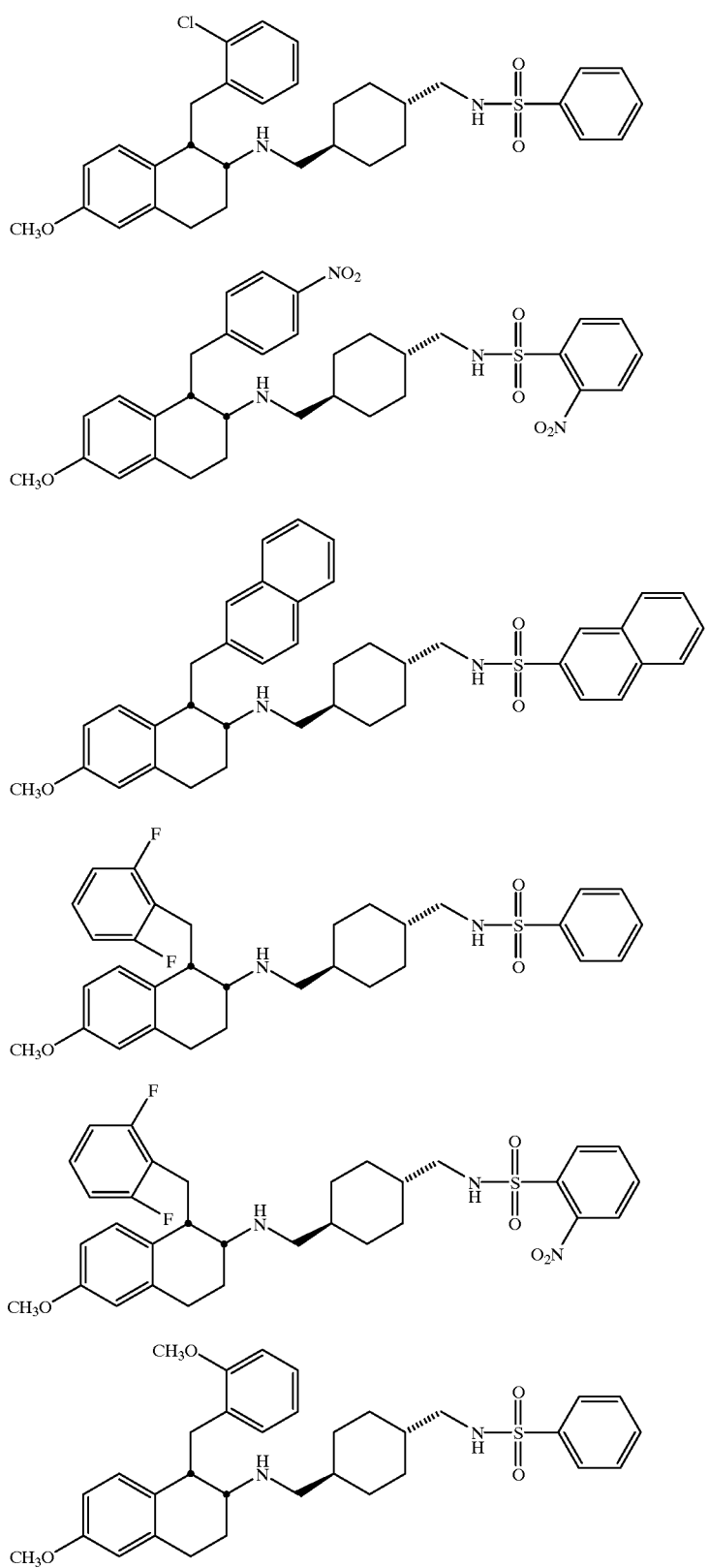

-continued
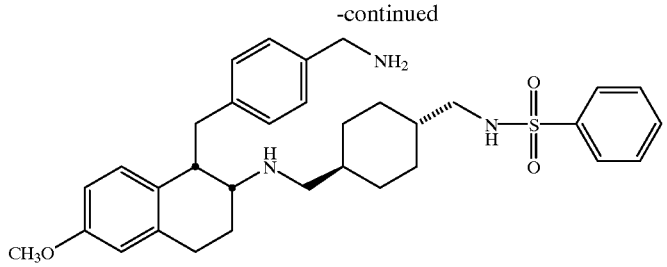
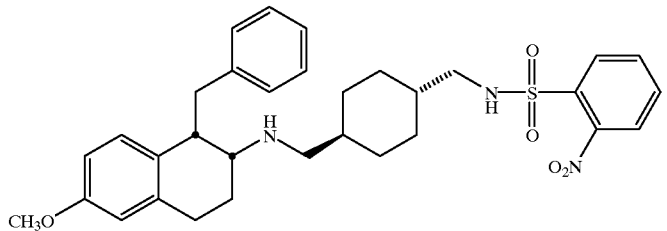
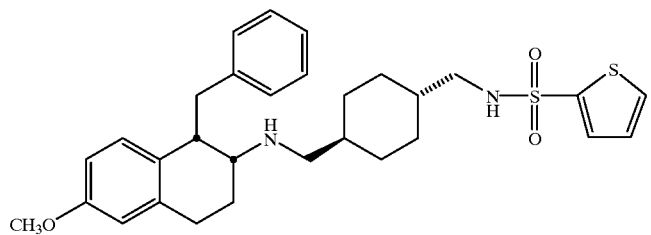
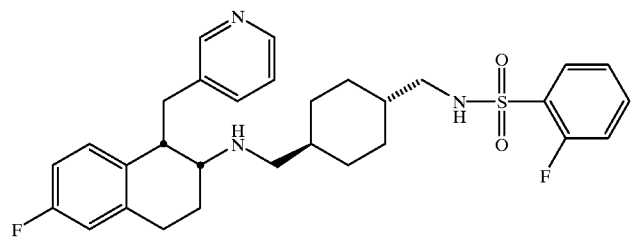
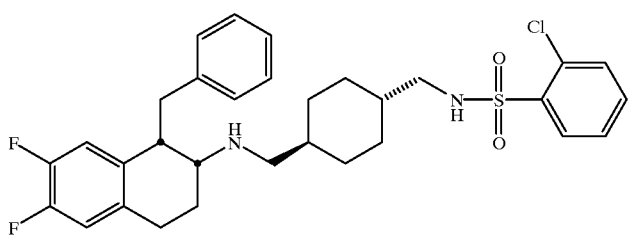
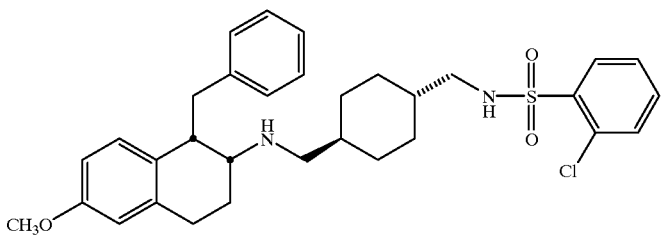
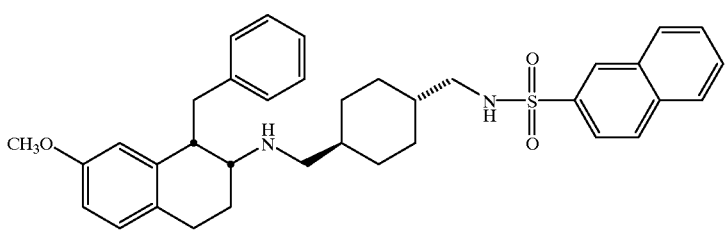

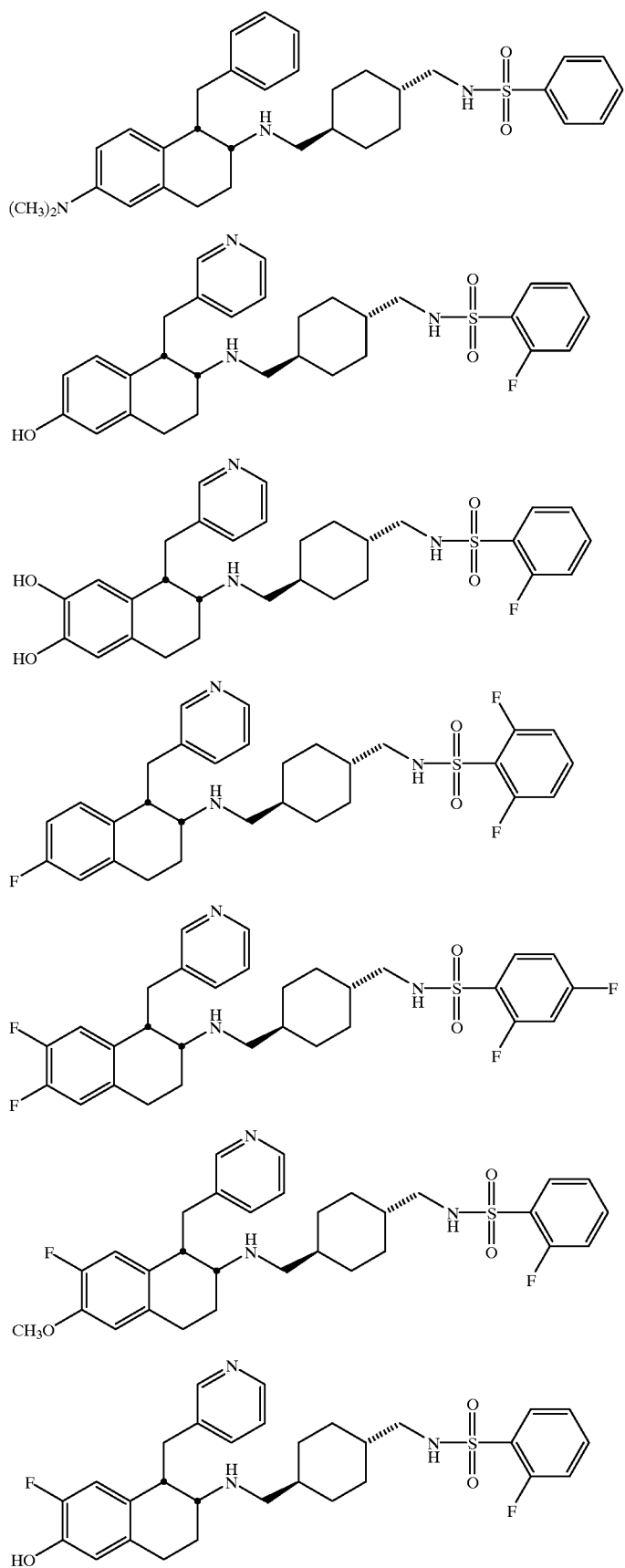

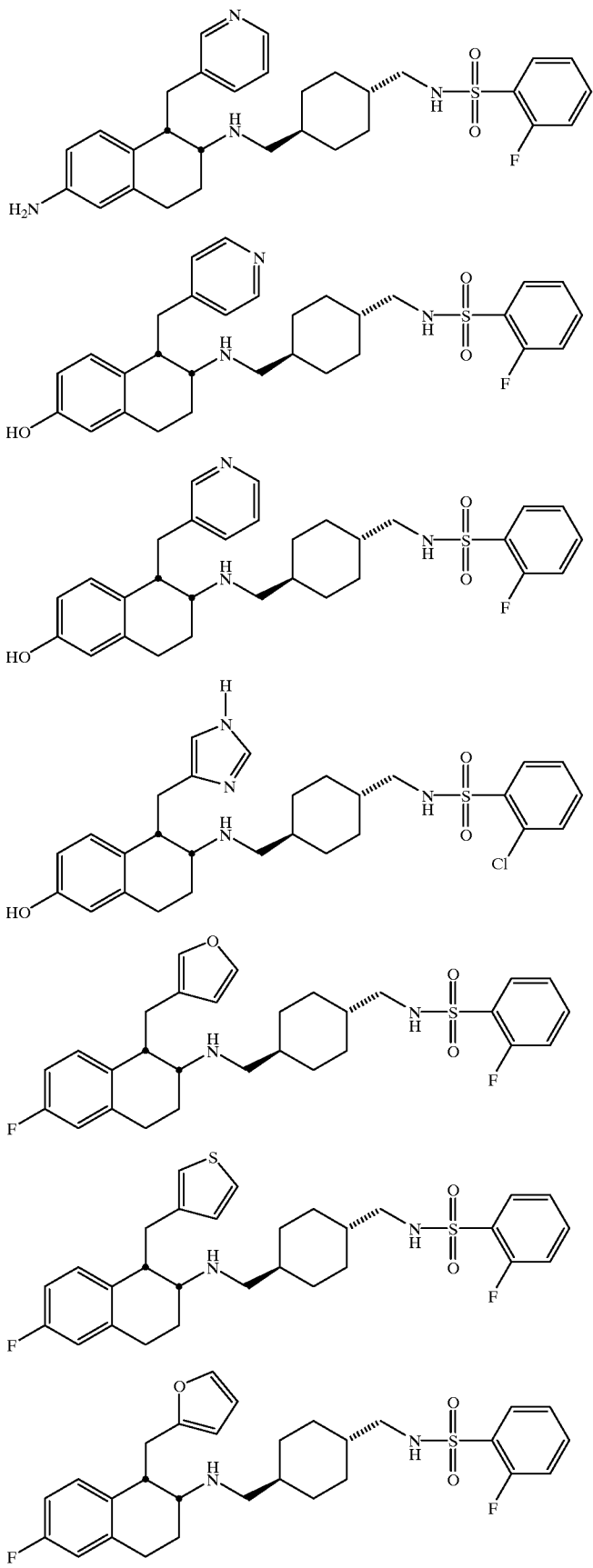

-continued
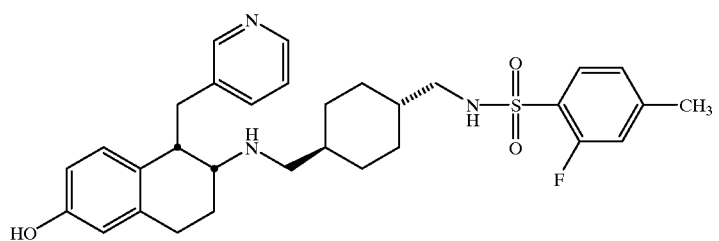
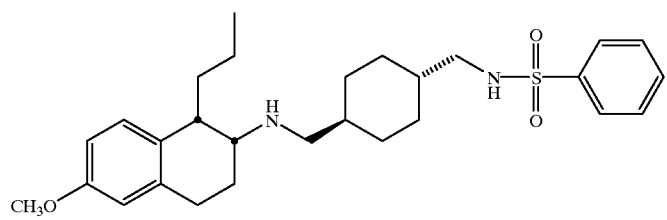
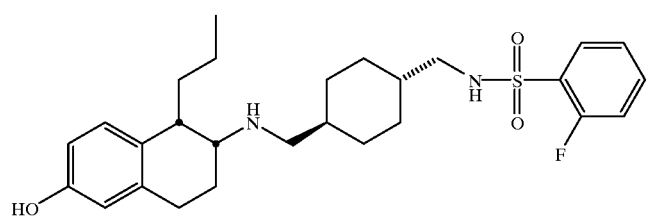
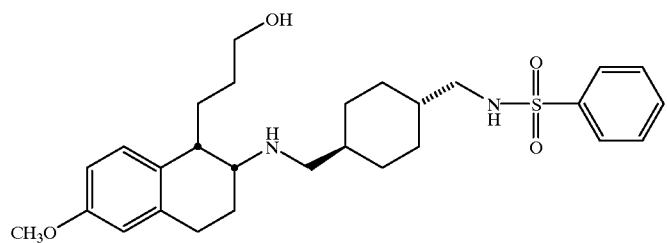
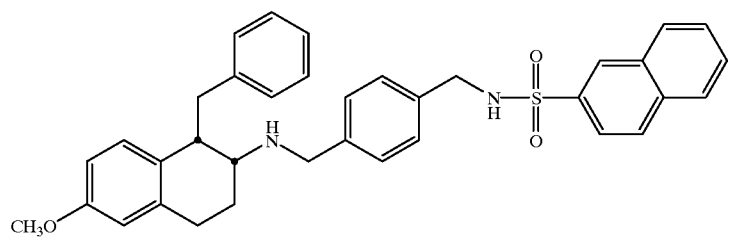
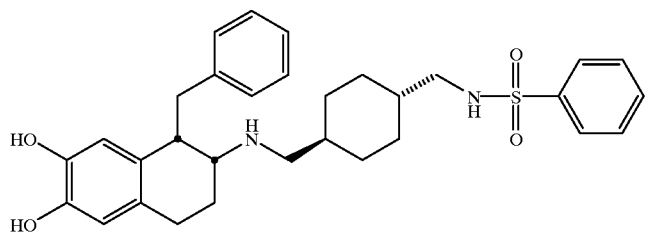
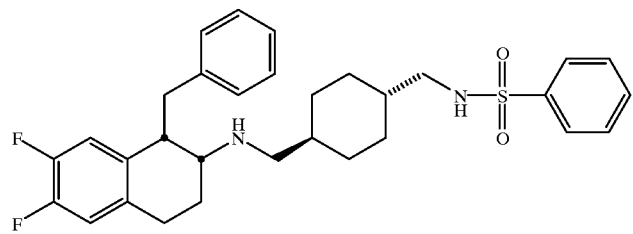

-continued
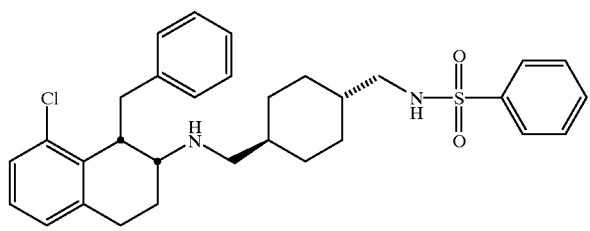
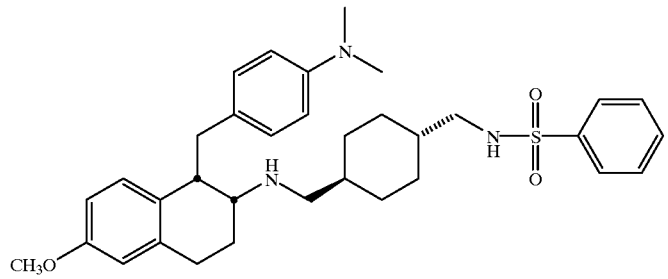
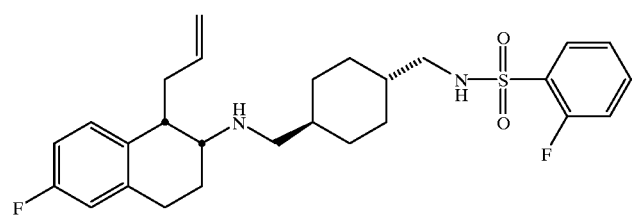
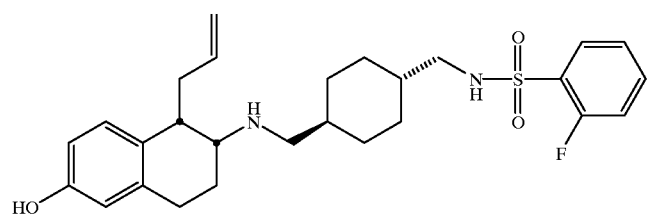
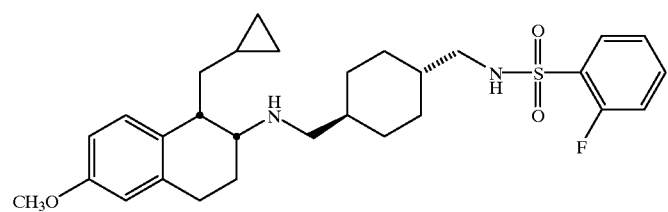
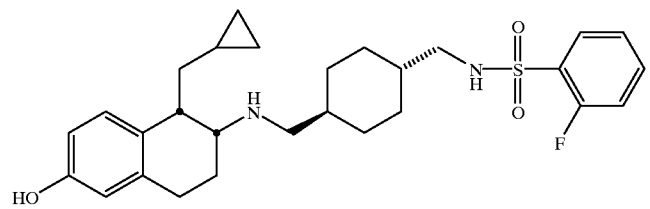
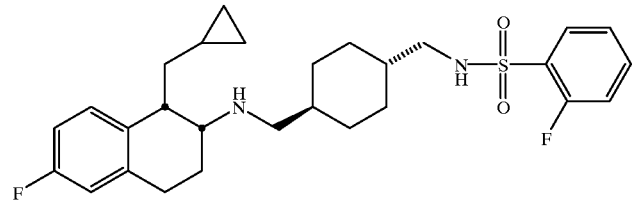

-continued
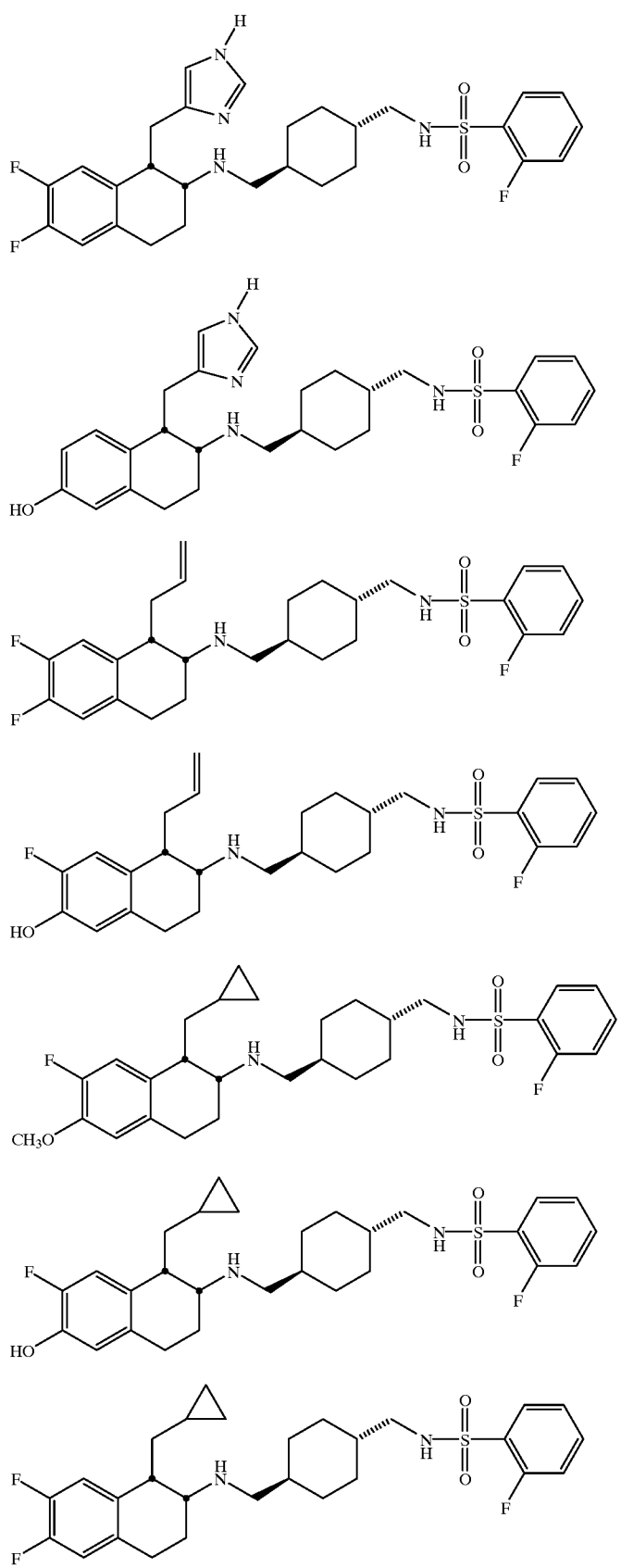

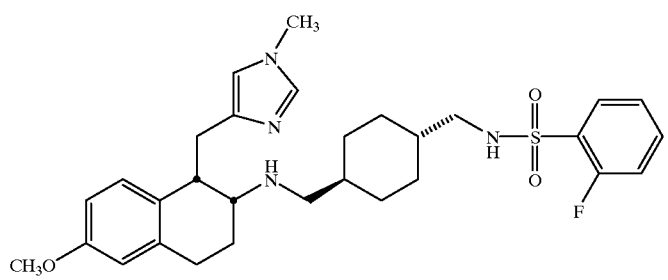
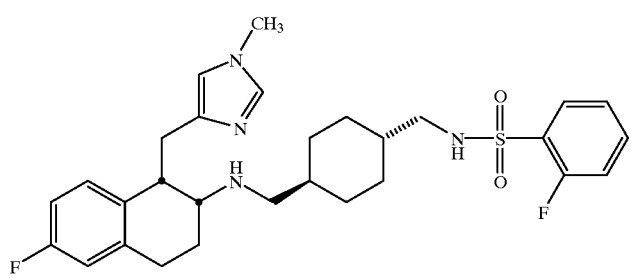
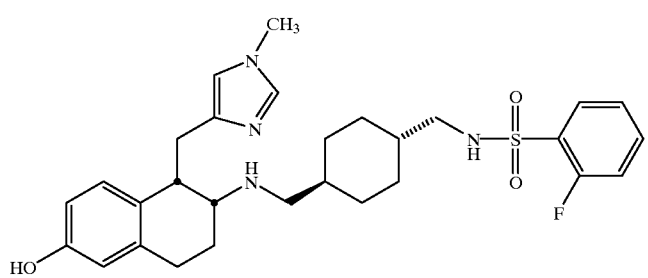
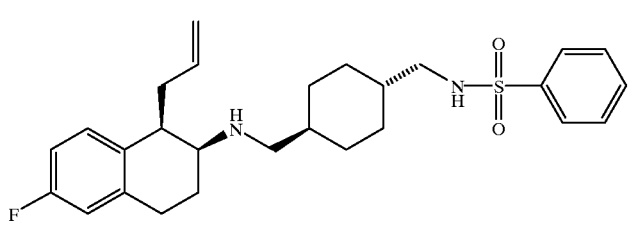
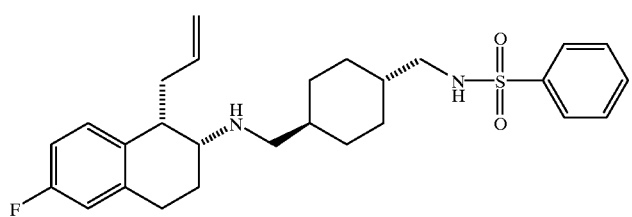
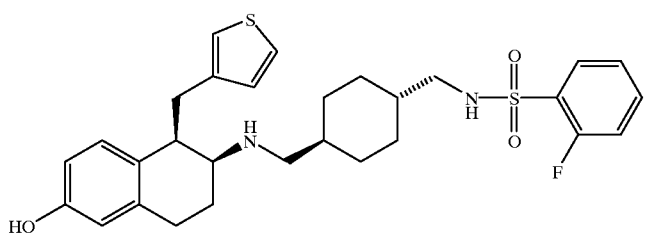

-continued

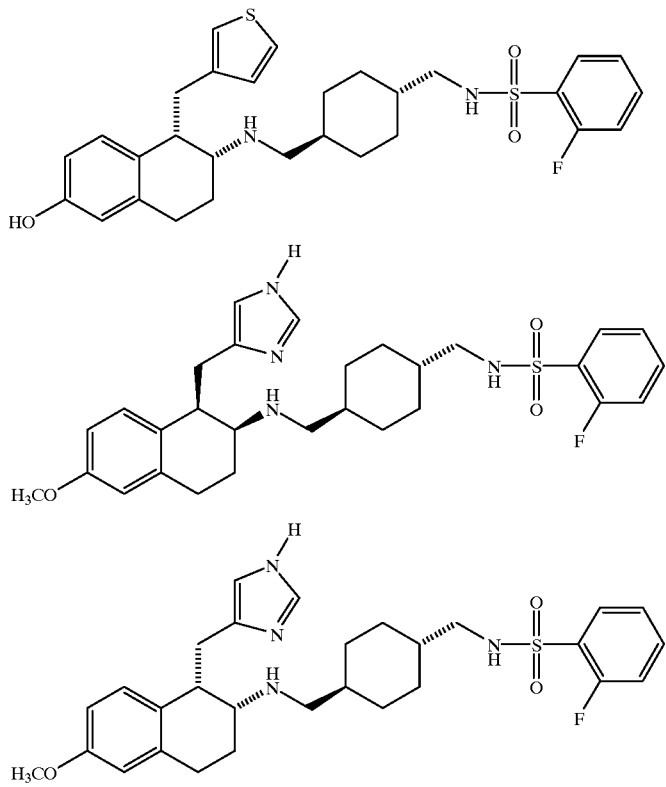

DETAILED DESCRIPTION OF THE INVENTION

The N-substituted aminotetralins of formula 1 that comprise this invention are synthesized via several distinct chemical syntheses as outlined in Schemes 1–5; each synthetic route consists of several sequential chemical operations that can be generalized as described below:

Introduction of the α-substituent onto the tetralone nucleus

Conversion to the corresponding α-substituted-β-aminotetralin

Acylation of the aminotetralin or reductive amination of the α-substituted-β-tetralone Reduction to re-generate the aminotetralin system (if needed) and/or Sulfonylation (if needed) (protecting group manipulations may be needed at various stages)

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halohydrocarbon solvents. In those cases wherein the product is isolated as the acid addition salt the free base is obtained by techniques known to those skilled in the art.

Specifically, an appropriately substituted ,B tetralone (II) is reacted with an aryl or heteroaryl aldehyde in the presence of a base such as piperidine, in an inert halohydrocarbon, ethereal or hydrocarbon solvent, such as benzene, from ambient temperature to reflux, to afford the corresponding α-benzylidenyl-β-tetralone or α-heteroarylmethylidenyl-β-tetralone (III). The p-tetralone (III) is dissolved in an inert hydrocarbon, ethereal, ester or alcohol solvent, such as methanol, and reacted with hydrogen gas from ambient pressure to about 100 p.s.i. in the presence of a suitable catalyst such as palladium on carbon. The reaction is performed at a temperature from ambient temperature to reflux, to yield the desired α-substituted-β-tetralone product (IV) (Scheme 1).

An alternative method for the preparation of α-substituted-β-tetralones (IV) involves the reaction of an appropriately substituted β-tetralone (II) with a base such as pyrrolidine in an inert halohydrocarbon solvent such as dichloromethane or hydrocarbon solvent such as benzene, under Dean-Stark conditions (removal of water) or in an alcohol solvent such as methanol, at a temperature from ambient temperature to reflux, to afford enamine (V). Alkylation of enamine (V) is accomplished by reaction with a benzylic, heterocyclicalkyl or an allylic halide in an inert solvent such as acetonitrile, at a temperature from ambient temperature to reflux, to afford the α-substituted-β-iminium salt (VI). Hydrolysis of the salt (VI) to produce the desired -substituted-p-tetralone product (IV) is accomplished by reaction of (VI) with water and an inorganic or organic acid such as hydrochloric or glacial acetic acid in an inert hydrocarbon, ethereal, alcohol or halohydrocarbon solvent, or a mixture thereof, such as methanol and dichloromethane (Scheme 1).

Scheme 1

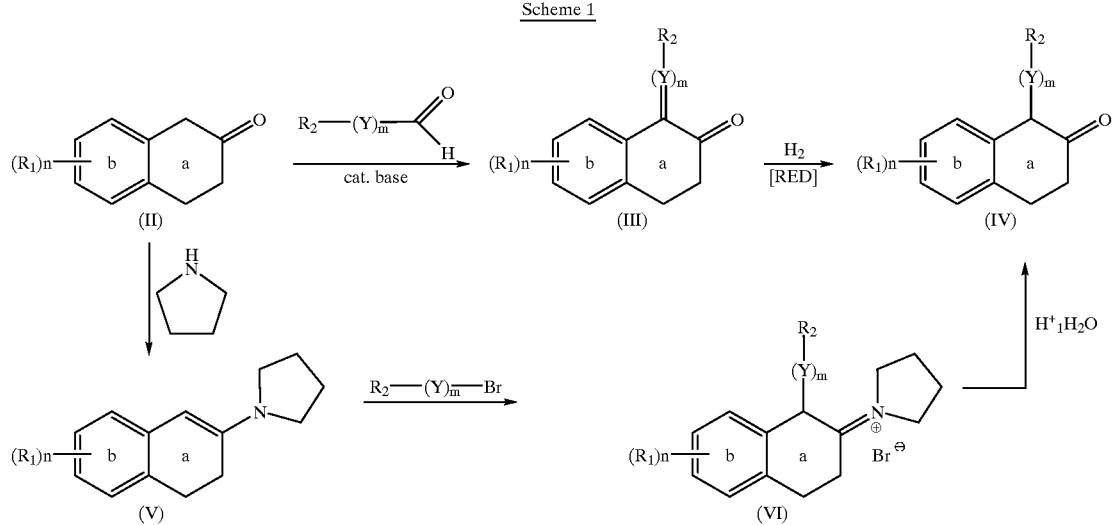

The α-substituted-β-tetralones (IV) are converted to the corresponding aminotetralins via reaction with an ammonium salt such as ammonium acetate in the presence of a reducing agent such as sodium cyanoborohydride, for example, in an inert halohydrocarbon, hydrocarbon, ethereal or alcohol solvent such as methanol to produce the cis-aminotetralin (VII). In some cases, the trans-aminotetralin (VIII) is also formed as a minor product. The cis-aminotetralins (VII) can also be isolated as acid addition salts by treatment with an organic or an inorganic acid, such as trifluoroacetic acid or hydrochloric acid, for example (Scheme 2).

Scheme 2

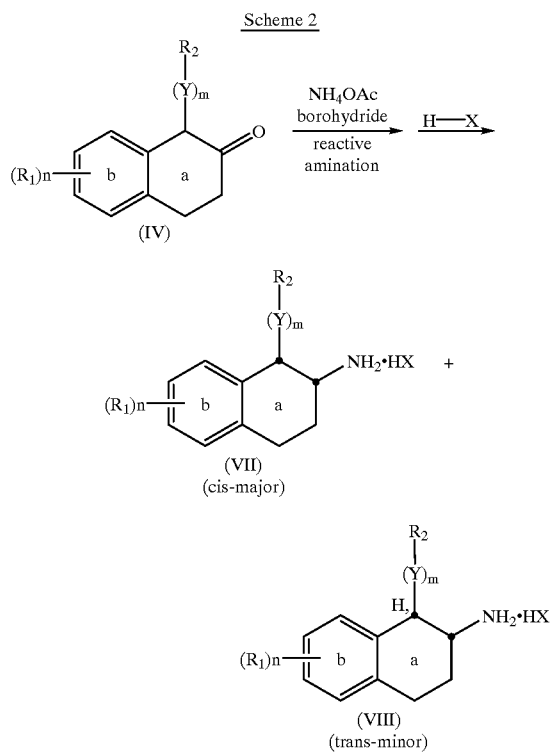

An alternative method for the preparation of the α-substituted-β-aminotetralins (VII) consists of reacting an appropriately α-substituted-β-tetralone with dibenzylamine in an inert halohydrocarbon, ethereal, alcohol or hydrocarbon solvent, such as benzene, under Dean-Stark conditions (removal of water), to afford enamine (IX). Alkylation of the enamine (IX) is accomplished via reaction with a benzylic or heterocyclicalkyl halide in an inert solvent such as acetonitrile, at a temperature from ambient temperature to reflux, to afford the α-substituted-β-iminium salt (X). The iminium salt (X) is dissolved in an inert hydrocarbon, ethereal or ester solvent such as ethyl acetate or alcohol solvent such as methanol and reacted with hydrogen gas at a pressure from ambient pressure to 100 p.s.i. in the presence of a suitable catalyst such as palladium on carbon, at a temperature from ambient temperature to reflux, to yield the desired β-aminotetralin (VII) (Scheme 3).

Scheme 3

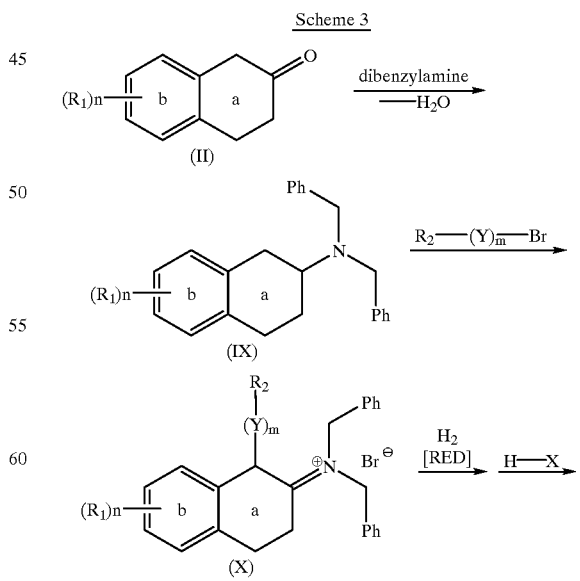

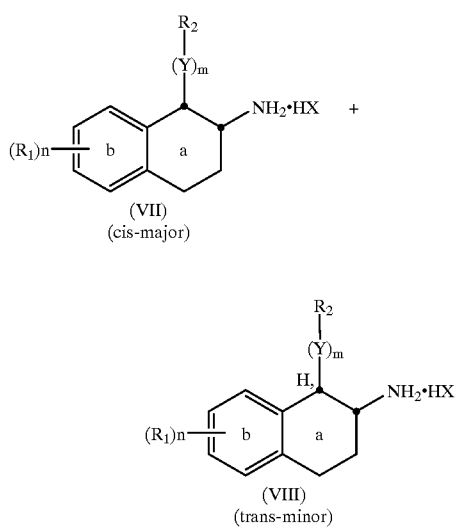

(VII) (cis-major)

(VIII) (trans-minor)

The β-aminotetralins described above are acylated via suitable amidation methods (see Gross and Meienhofer, Eds., "*The Peptides*", Vols. 1–3, Academic Press, New York, N.Y., 1979–1981). A carboxylic acid is converted to an activated ester via peptide coupling methods known to those skilled in the art, and subsequently reacted with an aminotetralin (VII) to afford the corresponding amide product. For example, a carboxylic acid such as trans-4-(2-naphthylsulfonamido)methylcyclohexane carboxylic acid or 4-(tert-butoxycarbonyl)aminomethylcyclohexane carboxylic acid is reacted with HBTU (2-(1H-benzotrazole-1-yl)-1,1,3,3-tetramethyluronium hexafluorophosphate and a β-aminotetralin (VII) in the presence of a base such as diisopropylethylamine, in an inert solvent such as N,N-dimethylformamide, at a temperature from ambient temperature to reflux, to afford amide (XI) or (XII) respectively. Cleavage of the BOC (butoxycarbonyl) protecting group with trifluoroacetic acid produces the free amine, which is sulfonylated to yield amide (XI).

Alternatively, the sulfonamido-carboxylic acid is treated with an amine base, such as triethylamine, in an inert hydrocarbon, ethereal or halohydrocarbon solvent, such as dichloroethane, and subsequently reacted with isobutyl chloroformate at a temperature from about −20° C. to 80° C. This mixture is then reacted with , aminotetralin (VII), in suitable inert solvent such a dichloromethane at a temperature from about −20° C. to reflux, affords the tetralinamide (XI).

The N-substituted aminotetralin compounds (I) of the invention are prepared via reduction of tetralinamide (XI) by reaction with a suitable reducing agent such as borane-tetrahydrofuran complex or lithium aluminum hydride in an inert hydrocarbon solvent such as toluene or ethereal solvent such as tetrahydrofuran, at a temperature from ambient temperature to reflux. The final product can be isolated as an acid addition salt upon treatment with a suitable organic acid such as trifluoroacetic acid or inorganic acid such as hydrochloric acid (Scheme 4).

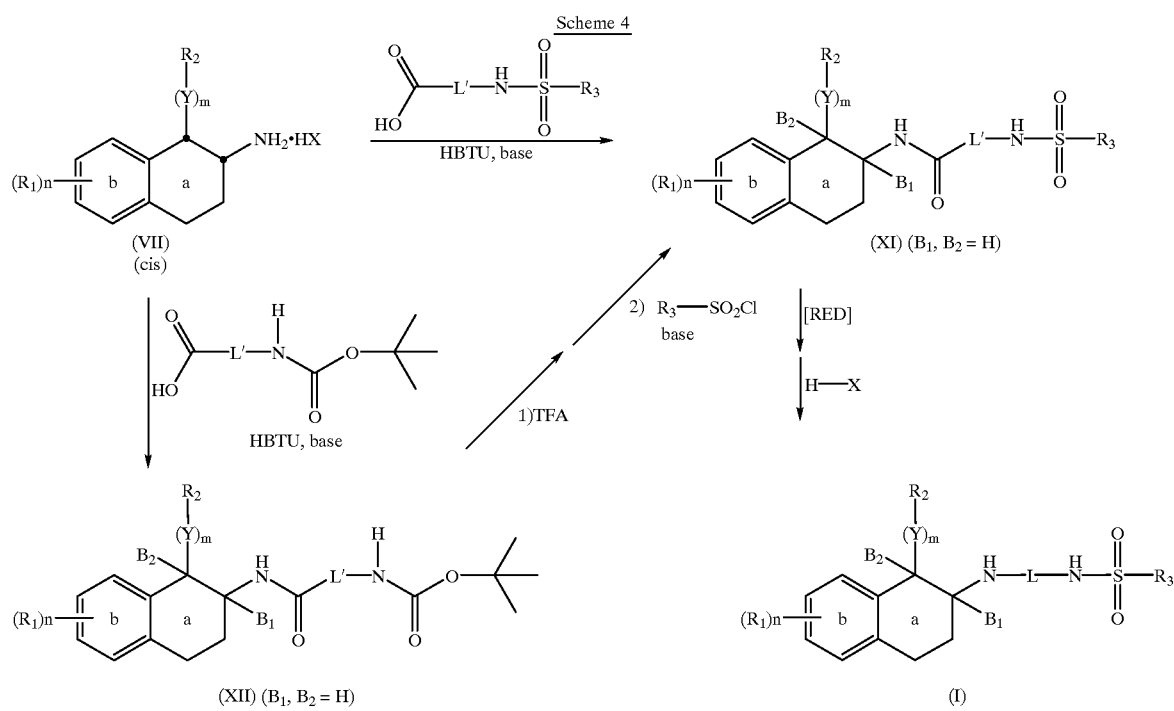

Scheme 4

L' = L less —CH$_2$—

An alternative method for the synthesis of N-substituted aminotetralins (I) entails the reaction of an appropriately α-substituted β-tetralone (IV) with an amine (H₂N—L—NHSO₂—R₃) in the presence of a reducing agent such as sodium borohydride, or sodium triacetoxyborohydride, for example, in an inert ethereal, halohydrocarbon, or alcohol solvent such as dichloromethane or methanol respectively, at a temperature from ambient temperature to reflux, to yield the desired N-substituted aminotetralin product (I) (Scheme 5).

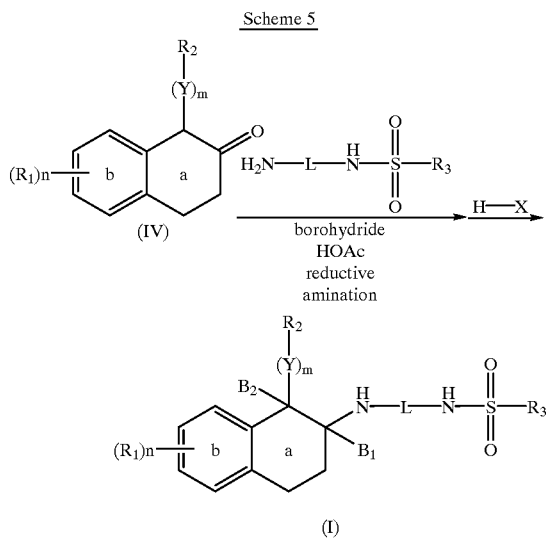

In the above reaction schemes, X is halo such as chloro, bromo and iodo and Ph is phenyl.

EXAMPLES

The following examples describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data is reported in parts per million downfield from tetramethylsilane. Mass spectra data is reported in mass/charge (m/z) units. Unless otherwise noted, the materials used in the examples were obtained from readily available commercial sources or synthesized by standard methods known to those skilled in the art.

Example 1
rac-[1α,2α(trans)]-N-[[[[[1,2,3,4-tetrahydro-6-methoxy-1-(phenylmethyl)-2-naphthalenyl]amino]methyl]-4-cyclohexyl]methyl]2-naphthalenesulfonamide (10)

A. 6-Methoxy-β-tetralone 1 (3.0 g, 17.0 mmol) was placed in a 250 mL round-bottom flask and dissolved in benzene (90 mL). Pyrrolidine (2.4 mL, 28.8 mmol) was added with stirring and the flask was flushed with argon. A Dean-Stark trap and a reflux condenser were attached and the solution was heated at reflux for 67 hours. After cooling, the solvent was removed in vacuo to yield enamine 2 as a orange glassy solid which was used in subsequent reactions without further purification. MS (MH⁺) 230; ¹H NMR (CDCl₃) δ1.92 (m, 4 H), 2.45 (t, 2H), 2.84 (t, 2H), 3.26 (m, 4H), 3.79 (s, 3H), 5.11 (s, 1H), 6.65 (m, 2H), 6.81 (m, 1H).

B. Enamine 2 was dissolved in acetonitrile (90 mL) in a 250 mL round-bottom flask and benzyl bromide (3.4 mL, 29 mmol) was added to this solution with stirring. The flask was flushed with argon and a reflux condenser was attached. The solution was heated at reflux for 19 hours. After cooling, the solvents were removed in vacuo, the resulting orange glassy solid was titurated with ethyl ether and filtered repeatedly until all traces of the benzyl bromide had been removed. The resulting iminium salt 3 was used in the next step without further purification. MS (MH⁻) 320.

C. The iminium salt 3 from the previous reaction was transferred to a 500 mL Erlenmeyer flask and methanol (100 mL), dichloromethane (50 mL), water (50 mL), and glacial acetic acid (3 mL) were added. The resulting mixture was flushed with nitrogen, capped, and stirred for 14 hours. The solvents were removed in vacuo. The resulting oil was dissolved in ethyl acetate (250 mL) and washed with water (4×100 mL). The organic extract was dried over magnesium sulfate, filtered, and the solvents removed in vacuo to yield an oily crude product. This material was purified via chromatography (silica gel column (dimensions 2.5×27 cm); 25% ethyl acetate: 75% hexanes (v/v) as the eluent). After evaporation of the appropriate fractions, 3,4-dihydro-6-methoxy-1-(phenylmethyl)-2(1H)-naphthalenone 4 was obtained as a thick yellow oil (2.13 g, 8.0 mmol). MS (MH⁺) 267; ¹H NMR (CDCl₃) δ2.43–2.60 (m, 3H), 2.75–2.81 (m, 1H), 3.18 (dd, 1H), 3.68 (dd, 2H), 3.79 (s, 3H), 6.58–6.91 (m, 5H), 7.15 (m, 3H). (FIG. 1).

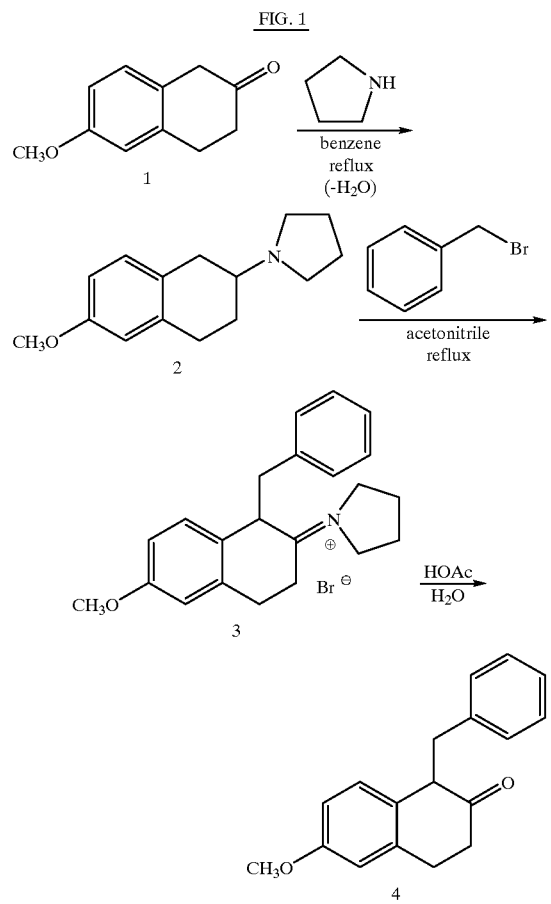

FIG. 1

Alternatively, 3,4-dihydro-6-methoxy-1-(phenylmethyl)-2(1H)-naphthalenone 4 is prepared as follows:

6-Methoxy-β-tetralone 1 (1.0 g, 5.7 mmol) was dissolved in benzene (25 mL) with stirring in a 50 mL round-bottom flask. To this solution, benzaldehyde (0.60 mL, 5.9 mmol) was added followed by catalytic piperidine (0.014 mL, 0.14 mmol). The flask was flushed with argon and a reflux condenser equipped with a Dean-Stark trap was attached. The solution was heated at reflux for 28 hours and then cooled to room temperature. The solvent was removed in vacuo to yield a dark orange oil. This crude product was dissolved in ethyl ether (100 mL) and then washed with 3N HCl (2×50 mL), water (1×50 mL), and lastly with saturated brine solution (1×50 mL). The organic extract was dried over magnesium sulfate, filtered, and the solvents removed in vacuo. The resultant oil was purified via column chromatography (silica gel column (dimensions 5×25 cm); 25% ethyl acetate:75% hexanes (v/v) as the eluent). After evaporation of the appropriate fractions, 3,4-dihydro-6-methoxy-1-(phenylmethylidenyl)-2-naphthalenone 5 was obtained as a pale yellow oil (0.70 g, 2.6 mmol) which solidified upon storage in a refrigerator. MS (MH$^+$) 265; $^1$H NMR (CDCl$_3$) δ2.54 (t, 2H), 2.98 (t, 2H), 3.79 (s, 3H), 6.63 (dd, 1H), 6.96 (d, 1H), 7.12 (d, 1H), 7.29 (m, 3H), 7.40–7.48 (m, 3H).

Compound 5 (0.464 g, 1.8 mmol) was placed in a 250 mL Parr shaker bottle and dissolved in ethyl acetate (25 mL). Separately, 10% palladium on carbon (0.029 g) was placed in a vial and to it was added methanol (25 mL) in order to create a slurry. This material was then carefully added to the Parr vessel and the mixture was hydrogenated under a pressure of approximately 50 psi for 19 hours. The reaction solution was filtered over a pad of Celite. The solvents were removed in vacuo and the resulting oil was purified by column chromatography (silica gel column (dimensions 2.5×26 cm); 25% ethyl acetate:75% hexanes (v/v) as the eluent). After evaporation of the appropriate fractions, 3,4-dihydro-6-methoxy-1-(phenylmethyl)-2(1H)-naphthalenone 4 was obtained as an off-white oil (0.40 g, 1.50 mmol) (FIG. 2).

FIG. 2

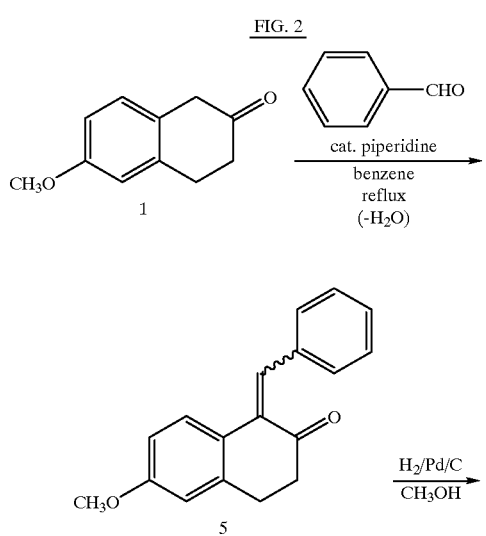

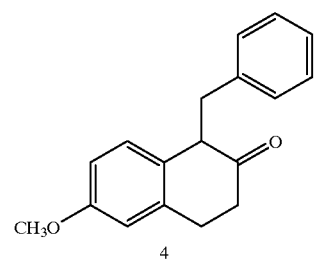

D. Ammonium acetate (10.7 g, 138 mmol) was added to a solution of 3,4-dihydro-6-methoxy-1-(phenylmethyl)-2(1H)-naphthalenone 4 (3.64 g, 13.6 mmol) in methanol (530 mL) in a I L round-bottom flask with vigorous stirring. Sodium cyanoborohydride (4.29 g, 68.3 mmol) was added and the flask was flushed with argon. A condenser was attached, and the solution was heated at reflux for 21 hours. The solution was cooled to room temperature and the solvents were removed in vacuo. The cream colored solid was dissolved in a mixture of ethyl ether (600 mL) and 0.1 M sodium hydroxide solution (225 mL). The aqueous phase was removed and the organics were washed with an additional 0.1 M sodium hydroxide solution (1×225 mL), and then with water (1×200 mL). The combined aqueous extracts were back extracted with ethyl ether (3×100 mL). The combined organic extracts were dried over magnesium sulfate, filtered, and the solvents were removed in vacuo to afford cis-1,2,3,4-tetrahydro-6-methoxy-1-(phenylmethyl)-2-naphthalenamine 6. The crude product was dissolved in ethyl ether (75 mL) and an excess of 1 M hydrogen chloride in ethyl ether was added. This resulted in a precipitate of the product as a HCl salt. The ethyl ether was removed in vacuo and any large chunks were crushed with a spatula. Ethyl acetate (25 mL) was added, the resultant slurry was heated to reflux and then cooled to room temperature. The solids were filtered off and rinsed with a small portion of ethyl acetate and then with ethyl ether and dried via aspiration to afford cis-1,2,3,4-tetrahydro-6-methoxy-1-(phenylmethyl)-2-naphthalenamine hydrochloride 6a as an off-white powder (2.13 g, 7.0 mmol). MS (MH$^+$) 268; $^1$H NMR (CDCl$_3$) δ2.05–2.30 (m, 2H), 2.50–2.60 (m, 1H), 2.83–3.03 (m, 3H), 3.30–3.40 (m, 2H), 3.71 (s, 3H), 6.00 (d, 1H), 6.35 (dd, 1H), 6.60 (d, 1H), 7.02–7.16 (m, 5H), 8.53 (bs, 1H), 8.96 (bs, 2H) (FIG. 3).

FIG. 3

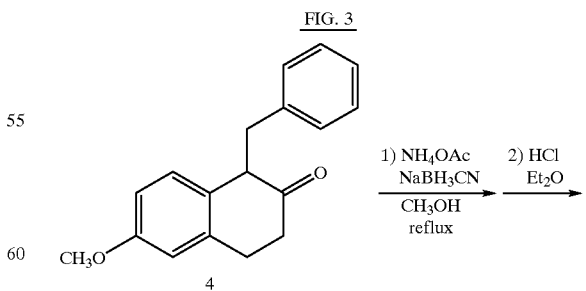

-continued

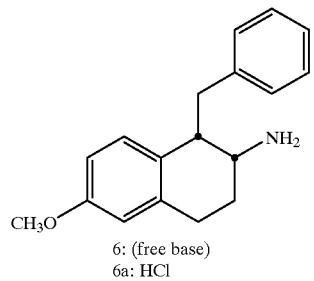

6: (free base)
6a: HCl

Alternatively, cis-1,2,3,4-tetrahydro-6-methoxy-1-(phenylmethyl)-2-naphthalenamine 6 is prepared as follows:

6-Methoxy-2-tetralone 1 (2.0 g, 11.3 mmol) was dissolved in benzene (60 mL) in a 100 mL round-bottom flask with stirring. N,N-dibenzylamine (2.4 mL, 12.5 mmol) was added and the flask was flushed with argon. A Dean-Stark trap and a condenser were attached and the solution was heated at reflux for 19 hours. After cooling, the solvents were removed in vacuo to afford enamine 7 which was used without further purification. MS (MH$^+$) 356.

Enamine 7 was dissolved in acetonitrile (60 mL) in a 100 mL round-bottom flask and benzyl bromide (1.5 mL, 12.6 mmol) was added. The flask was flushed with argon and a reflux condenser was attached. The solution was heated at reflux for 14 hours. After cooling, the solvents were removed in vacuo to yield iminium salt 8 as a glassy orange solid which was used without further purification. MS (MH$^-$) 446.

Approximately half of the iminium salt from the previous reaction was transferred to a 250 mL Parr Shaker bottle along with methanol (50 mL). Separately, 10% palladium hydroxide on carbon (0.30 g) was placed into a vial and methanol (50 mL) was added carefully to form a slurry. This material was added to the iminium salt solution and the mixture was hydrogenated under a pressure of approximately 50 p.s.i. for 17 hours. The reaction solution was filtered over a pad of Celite to remove the catalyst. The solvent was removed in vacuo. The resulting oil was dissolved in ethyl acetate (300 mL) and this solution was washed with 0.2 M sodium hydroxide solution (2×125 mL) and then with water (1×100 mL). The aqueous layers were back extracted with ethyl acetate (1×50 mL). The combined organic extracts were dried over magnesium sulfate, filtered, and the solvents were removed in vacuo. The resulting oil was purified via chromatography (silica gel column (dimensions 5×28 cm) eluting first with dichloromethane (400 mL) and then with dichloromethane/acetone/methanol (50:50:5) (v/v). After evaporation of the appropriate fractions, cis-1,2,3,4-tetrahydro-6-methoxy-1-(phenylmethyl)-2-naphthalenamine 6 was obtained as a brown oil (0.37 g, 1.4 mmol). MS (MH$^+$) 268; $^1$H NMR (CDCl$_3$) δ1.45 (bs, 2H), 1.86 (m, 2H), 2.80–3.07 (m, 5H), 3.20 (m, 1H), 3.75 (s, 3H), 6.52–6.67 (m, 3H), 7.10–7.30 (m, 5H). (FIG. 4).

FIG. 4

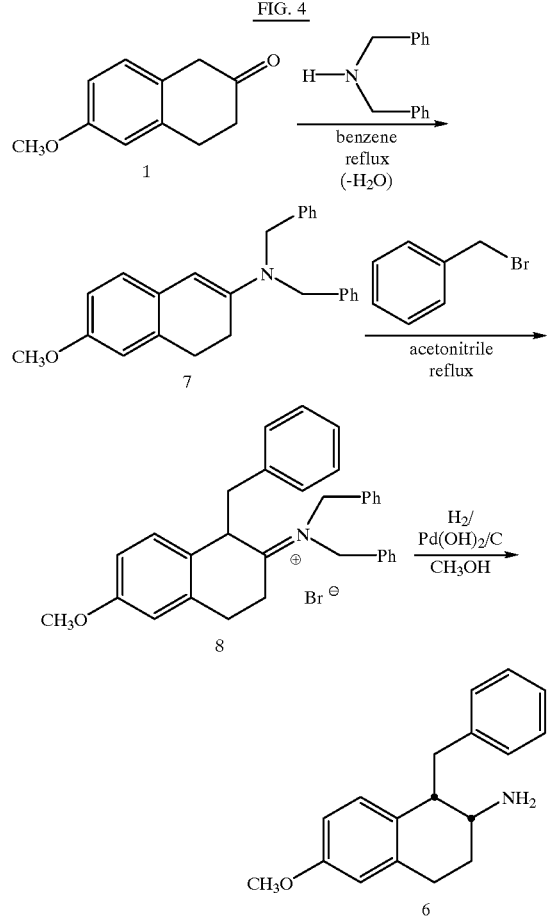

E. trans-4-(2-Naphthylsulfonamido)methylcyclohexanecarboxylic acid (0.394 g, 1.13 mmol) was placed in a 50 mL round-bottom flask and suspended in dichloromethane (10 mL). Triethylamine (0.32 mL, 2.3 mmol) was added which resulted in dissolution. Isobutylchloroformate (0.29 mL, 2.3 mmol) was slowly added and the mixture was stirred for 1 hour, presumably forming the anhydride species. cis-1,2,3,4-Tetrahydro-6-methoxy-1-(phenylmethyl)-2-naphthalenamine 6 (0.364 g, 1.36 mmol) was dissolved in dichloromethane (10 mL) and this solution was added to the solution prepared above. The reaction mixture was stirred for 3 hours at ambient temperature at which time an additional dichloromethane (50 mL) was added. This mixture was washed with 0.25 M sodium hydroxide solution (35 mL). The organic layer was separated and the aqueous layer was extracted with additional dichloromethane (2×25 mL). The organic extracts were combined and washed with brine (1×25 mL). The organics were dried over magnesium sulfate, filtered, and the solvents were removed in vacuo. The residue obtained was purified via chromatography (silica gel column (dimensions 2.5×26 cm) eluting with a gradient of: 100% dichloromethane (100 mL), 98:2 dichloromethane/acetone (100 mL), 96:4 dichloromethane/acetone (100 mL), 94:6 dichloromethane/acetone (100 mL), 92:8 dichloromethane/acetone (100 mL), then the remainder with 90:10 dichloromethane/acetone (100 mL). After evaporation of the appropriate fractions, [1α,2α(trans)]-4-[[(2-naphthalenylsulfonyl)amino]methyl]-N-[1,2,3,4-tetrahydro-6-methoxy-1-(phenylmethyl)-2-naphthalenyl]-cyclohexanecarboxamide 9 (0.314 g, 0.526 mmol) was obtained as an off-white powder. MS (MH+) 597; $^1$H NMR (DMSO-$d_6$) 50.71–0.85 (m, 2H), 1.25–1.38 (m, 3H), 1.69 (m, 5H), 1.90 (m, 1H), 2.10 (m, 1H), 2.43–2.63 (m, 3H), 2.79–2.96 (m, 3H), 3.11 (s, 1H), 3.65 (s, 3H), 3.82–3.92 (m, 1H), 6.31 (d, 1H), 6.45 (dd, 1H), 6.63 (d, 1H), 6.97 (app d, 2H), 7.13–7.26 (m, 3H), 7.68 (m, 3H), 7.85 (app d, 2H), 8.05 (app d, 1H), 8.15 (m, 2H), 8.44 (s, 1H).

F. The amide 9 from the previous reaction (0.282 g, 0.473 mmol) was suspended in tetrahydrofuran (20 mL) in a 50 mL round-bottom flask and lithium aluminum hydride solution (1.4 mL of a 1 M solution in THF) was added. The flask was flushed with argon and a condenser was attached. The reaction mixture was heated at reflux and during the course of the reaction more LAH solution was added (2.5 mL) and more THF was added (20 mL). After a reflux period of 50 hours, the reaction was cooled to room temperature and excess ethyl acetate was added to quench the remaining LAH. The solution was filtered over Celite to remove the inorganic salts. The solvents were removed in vacuo. The crude product was dissolved in ethyl acetate (150 mL) and washed with 1 M hydrochloric acid (2×50 mL). The organic extract was dried over magnesium sulfate, filtered, and the solvents were removed in vacuo. Excess ethereal hydrogen chloride (approx. 15 mL of a 1 M solution) was added and the solvents and excess HCl were removed in vacuo. The product was recrystallized from ethyl acetate (15 mL)/acetone (19 mL) to yield [1α,2α(trans)]-N-[[[[1,2,3,4-tetrahydro-6-methoxy-1-(phenylmethyl)-2-naphthalenyl]amino]methyl]-4-cyclohexyl]methyl]2-naphthalenesulfonamide hydrochloride 10a (0.082 g, 0.132 mmol) as a white powder. MS (MH+) 583; $^1$H NMR (DMSO-$d_6$) δ0.82–1.07 (m, 4H), 1.39 (m, 1H), 1.64–1.96 (m, 5H), 2.17 (m, 2H), 2.45 (m, 1H), 2.65 (m, 2H), 2.83–3.12 (m, 6H), 3.47 (m, 1H), 3.64 (s, 3H), 5.84 (d, 1H), 6.31 (d, 1H), 6.68 (app s, 1H), 7.06 (m, 2H), 7.27 (m, 4H), 7.70 (m, 2H), 7.83 (app d, 1H), 8.05 (app d, 1H), 8.16 (m, 2H), 8.43 (s, 1H), 8.95 (bs, 2H). (FIG. 5).

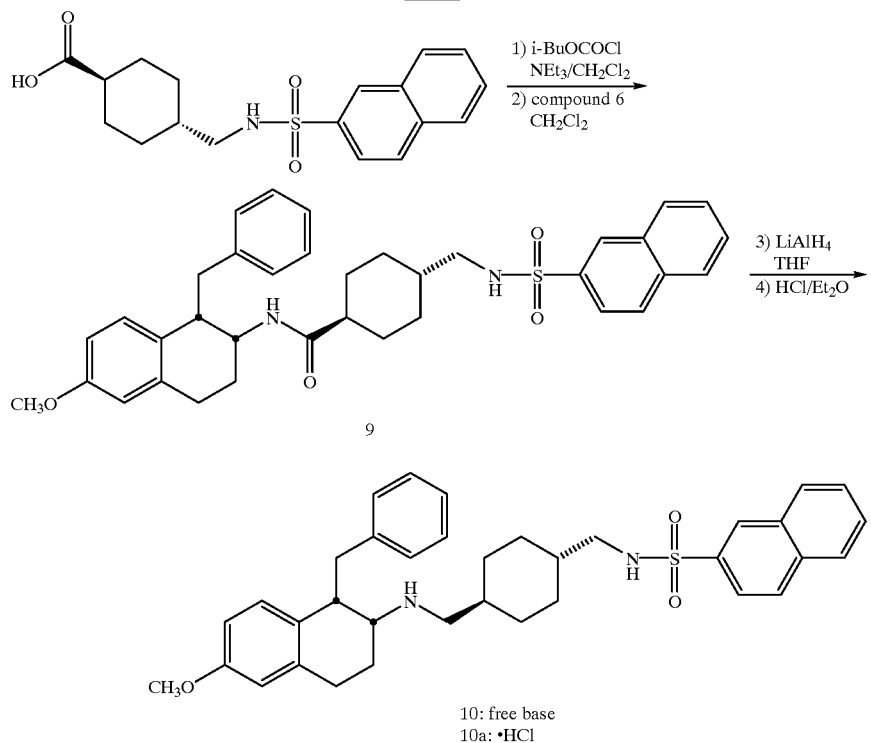

FIG. 5

Example 2 rac-[1α,2α(trans)]-N-[[[[[1,2,3,4-tetrahydro-6-methoxy-1-(phenylmethyl)-2-naphthalenyl]amino]-5-pentyl]2-naphthalenesulfonamide (11)

3,4-Dihydro-6-methoxy-1-(phenylmethyl)-2(1H)-naphthalenone 4 (0.136 g, 0.511 mmol) was dissolved in methanol (5 mL) in a 20 mL screw cap vial equipped with a stir bar. After dissolution, 1-amino-5-(2-naphthalenylsulfonamido)pentane hydrochloride salt (0.170 g, 0.517 mmol) was added followed by sodium cyanoborohydride (0.098 g, 1.60 mmol). The vial was flushed with nitrogen and capped. Stirring was continued for 17 hours after which time dichloromethane (25 mL) and saturated sodium bicarbonate (25 mL) was added. The organics were removed and the aqueous layer was extracted with dichloromethane (2×25 mL). The organic extracts were combined and washed with brine (1×25 mL), dried over magnesium sulfate, filtered, and the solvents were removed in vacuo. The crude product was purified via chromatography (silica gel column (dimensions 2.5×17 cm); 25% dichloromethane:75% acetone (v/v) as the eluent). After evaporation of the appropriate fractions, the product was dissolved in ethyl ether and 1 M hydrogen chloride in ethyl ether was added to precipitate [1α,2α(trans)]-N-[[[[[1,2,3,4- tetrahydro-6-methoxy-1-(phenylmethyl)-2-naphthalenyl]amino]-5-pentyl]2-naphthalenesulfonamide hydrochloride 11a (0.036 g, 0.062 mmol) as an off-white powder. MS (MH⁺) 543. (FIG. 7)

the hydrogenation was repeated for 20 hours. The catalyst was then removed by filtration over Celite. Removal of the solvents in vacuo yielded 3,4-dihydro-6-methoxy-1-(3-pyridinylmethyl)-2(1H)-naphthalenone 13 as an

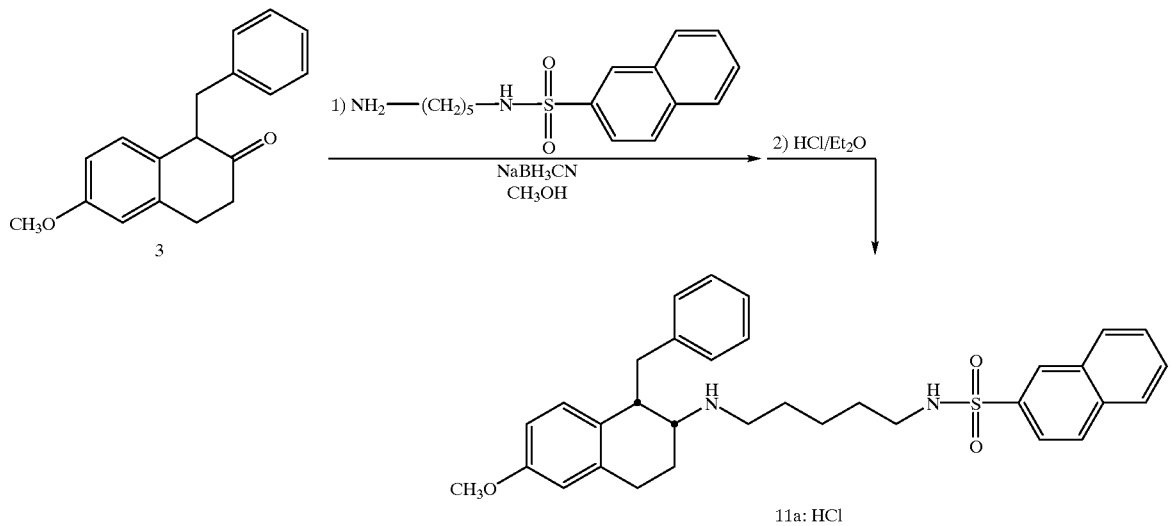

FIG. 7

Example 3
rac-[1α,2α(trans)]-N-[[[[[1,2,3,4-tetrahydro-6-methoxy-1-(3-pyridinylmethyl)-2-naphthalenyl]amino]methyl]-4-cyclohexyl]methyl]2-naphthalenesulfonamide (18)

A. 6-Methoxy-β-tetralone 1 (2.0 g, 11.3 mmol) and diisopropylethylamine (0.20 mL, 1.1 mmol) were dissolved in benzene (60 mL) with stirring in a 100 mL round-bottom flask. 3-Pyridylcarboxaldehyde (1.1 mL, 11.7 mmol) was added and the reaction vessel was flushed with argon and a Dean-Stark trap with reflux condenser was attached. The mixture was heated at reflux for 19 hours. After cooling, HPLC analysis indicated that no products had formed. Piperidine (0.094 mL, 1.1 mmol) was added at this time and heating at reflux was continued for 23 hours. The solvents were removed in vacuo to yield a glassy orange solid. Chromatographic purification (silica gel column (dimensions 5×29 cm) eluting with a gradient of: 100% hexane (400 mL), 75%/25% hexane/ethyl acetate (v/v) (400 mL), 50%/50% hexane/ethyl acetate (v/v) (400 mL), 25%/75% hexane/ethyl acetate (v/v) (400 mL), and finally with 100% ethyl acetate) was performed. After evaporation of the appropriate fractions, 3,4-dihydro-6-methoxy-1-((3-pyridinyl)methylidenyl)-2-naphthalenone 12 (1.484 g, 5.59 mmol) was obtained as a orange oil which solidified upon standing in the refrigerator. MS (MH⁺) 266; ¹H NMR (CDCl₃) δ2.67 (t, 2H), 3.02 (t, 2H), 3.83 (s, 3H), 6.60 (dd, 1H), 6.82 (d, 1H), 7.19 (m, 2H), 7.51 (s, 1H), 7.71 (d, 1H), 8.49 (dd, 1H), 8.65 (d, 1H).

B. The naphthalen-2-one 12 (1.442 g, 5.44 mmol) obtained above was dissolved in absolute ethanol (50 mL) and transferred to a 250 mL Parr hydrogenation bottle. Separately, ethanol was carefully added to 10% palladium on carbon (0.020 g) and this slurry was added to the Parr bottle. The mixture was hydrogenated under a pressure of 50 psi for 16 hours. The catalyst was removed by filtration over Celite. Spectroscopic evidence indicated the presence of some starting material and so more palladium catalyst (0.081 g) was added to the ethanol solution and orange oil which was used in the next step without further purification. MS (MH⁺) 268.

C. Naphthalen-2-one 13 obtained above was dissolved in methanol (275 mL) in a 1 L round-bottom flask. Ammonium acetate (4.27 g, 55.4 mmol) was added to the stirred methanol solution and was allowed to completely dissolve before proceeding. Sodium cyanoborohydride (1.703 g, 27.5 mmol) was then added to the methanol solution. The reaction vessel was flushed with nitrogen and the solution refluxed for 18 hours. The solvents were then removed in vacuo to yield a yellow solid which was dissolved in ethyl ether (500 mL) and 0.1 M sodium hydroxide solution (275 mL). The organic layer was removed and washed with an additional 0.1 M sodium hydroxide solution (275 mL) and with water (250 mL). The combined aqueous washes were back extracted with ethyl ether (3×100 mL). The organic extracts were combined and dried over sodium sulfate. The solvents were removed in vacuo and the residue was taken up in ethyl ether and a minimum amount of dichloromethane. An excess of 1 M hydrogen chloride in ethyl ether was added and a dark tan precipitate formed. The solvents were removed in vacuo and the resulting solid was titurated with ether and dried in a vacuum oven to yield 1,2,3,4-tetrahydro-6-methoxy-1-(3-pyridinylmethyl)-2-naphthalenamine bis-hydrochloride 14 as a tan-orange solid (1.208 g, 3.54 mmol) MS (MH⁺) 269; ¹H NMR (DMSO-d₆) δ1.95–2.20 (m, 2H), 2.68–3.29 (m, 4H), 3.30–3.48 (m, 2H), 3.69 (s, 3H), 5.98 (d, 1H), 6.41 (dd, 1H), 6.75 (d, 1H), 7.98 (dd, 1H), 8.36 (d, 1H), 8.68–8.89 (m, 5H).

D. The 2-naphthalenamine 14 (1.193 g, 3.50 mmol) was dissolved in N,N-dimethylformamide (30 mL) in a 100 mL round-bottom flask and diisopropylethylamine (2.0 mL, 11.5 mmol) was added to the solution. N-(tert-Butoxycarbonyl)aminomethylcyclohexane carboxylic acid (0.912 g, 3.54 mmol) was added followed by HBTU (1.336 g, 3.52 mmol). The reaction mixture was stirred for 2 hours and then poured into water (400 mL). A fine precipitate formed which was separated by centrifugation followed by decanting, adding fresh water and re-centrifugation followed by a final decanting. The remaining material was dried in a vacuum oven and then purified via chromatography (silica gel column (5×17 cm) eluting with a gradient of: 75% hexane/ethyl acetate (v/v) (300 mL), 50% hexane/ethyl acetate (300 mL), 25% hexane/ethyl acetate (300 mL), and finally with 100% ethyl acetate. After evaporation of the appropriate fractions the resulting yellow solid was titurated with ethyl ether and then dried in a vacuum oven to yield [1α,2α(trans)]-4-[[(tert-butoxycarbonyl)amino]methyl]-N-[1,2,3,4-tetrahydro-6-methoxy-1-(3-pyridinylmethyl)-2-naphthalenyl]-cyclohexanecarboxamide 15 (0.629 g, 1.24 mmol) MS (MH+) 508; ¹H NMR (DMSO-d₆) δ0.81–1.04 (m, 2H), 1.31–1.54 (m, 13H), 1.70–2.02 (m, 7H), 2.80–3.04 (m, 6H), 3.35 (m, 1H), 3.79 (s, 3H), 4.27 (m, 1H), 4.59 (m, 1H), 5.42 (d, 1H), 6.58–6.77 (m, 3H), 7.47 (d, 1H), 8.34 (s, 1H), 8.48 (d, 1H).

E. The carboxamide 15 obtained above (0.603 g, 1.19 mmol) was suspended in 100 mL dioxane in a 250 mL round-bottom flask. While cooling with an ice bath, hydrogen chloride gas was bubbled into the solution until saturated. The solvents were removed in vacuo and the resulting material was dissolved in methanol and an excess of ethereal hydrogen chloride was added. The solvents were removed in vacuo and the resulting product was titurated with ethyl ether and filtered. The resultant hygroscopic off-white solid was dried at 40° C. in a vacuum oven to afford [1α,2α(trans)]-4-(aminomethyl)-N-[1,2,3,4-tetrahydro-6-methoxy-1-(3-pyridinylmethyl)-2-naphthalenyl]-cyclohexanecarboxamide bis-hydrochloride 16 (0.502 g, 1.04 mmol). MS (MH+) 408; ¹H NMR (DMSO-d₆) δ0.80–1.03 (m, 2H), 1.19–1.42 (m, 2H), 1.44–1.89 (m, 6H), 1.93 (m, 1H), 2.10 (m, 1H), 2.56–2.70 (m, 2H), 2.71–3.01 (m, 3H), 3.09 (m, 1H), 3.34 (m, 1H), 3.70 (s, 3H), 3.91 (m, 1H), 6.58–6.63 (m, 2H), 6.71 (s, 1H), 7.87–8.11 (m, 5H), 8.22 (d, 1H), 8.59 (s, 1H), 8.75 (d, 1H).

F. The amine hydrochloride 16 obtained above (0.102 g, 0.212 mmol) was mixed with dichloromethane (13 mL) and diisopropylethylamine (0.125 mL, 0.718 mmol). 2-Napthylsulfonylchloride (0.048 g, 0.212 mmol), dissolved in dichloromethane (12 mL), was added to the mixture. The resulting solution was stirred for 1 hour after which the solvents were removed in vacuo. The residue was taken up in dichloromethane (75 mL) and this mixture was washed with 0.1 M sodium hydroxide solution (2×55 mL) and water (1×50 mL). The organics were dried over magnesium sulfate and the solvents were removed in vacuo to yield [1α,2α(trans)]-4-[[(2-naphthalenylsulfonyl)amino]methyl]-N-[1,2,3,4-tetrahydro-6-methoxy-1-(3-pyridinylmethyl)-2-naphthalenyl]-cyclohexanecarboxamide 17 (0.126 g, 0.211 mmol). MS (MH+) 598.

G. The carboxamide 17 obtained above (0.119 g, 0.199 mmol) was dissolved in tetrahydrofuran (15 mL) in a 100 mL round-bottom flask. Borane-tetrahydrofuran (2.00 mL of a 1 M solution, 2.00 mmol) was added. The resultant mixture was stirred for 3 hours at room temperature at which time it was found that the reaction was proceeding very slowly (HPLC). A reflux condenser was attached and the solution was heated at reflux for 1 hour. After the solution had cooled, water (2 mL) was added to quench the excess borane. The solvents were then removed in vacuo. Hydrochloric acid (15 mL of a 6 M solution) was added to the residue and this mixture was heated at reflux for 30 minutes. The solution was cooled and dichloromethane (100 mL) and 1 M sodium hydroxide solution (100 mL) were added. The organic extract was removed and the aqueous layer was washed with dichloromethane (2×100 mL). The organic extracts were combined and dried over magnesium sulfate and the solvents were removed in vacuo. Ethyl ether (100 mL) was added along with enough methanol to solubilize the free base. An excess of ethereal hydrogen chloride was added and the solvents were removed in vacuo. The product was titurated with ethyl ether and dried in a vacuum oven to yield [1α,2α(trans)]-N-[[[[[1,2,3,4-tetrahydro-6-methoxy-1-(3-pyridinylmethyl)-2-naphthalenyl]amino]methyl]-4-cyclohexyl]methyl]2-naphthalenesulfonamide bis-hydrochloride 18a (0.110 g, 0.167 mmol). MS (MH+) 584; ¹H NMR (DMSO-d₆) δ0.70–1.03 (m, 4H), 1.19–1.44 (m, 2H), 1.65–1.87 (m, 3H), 1.88–2.02 (m, 2H), 2.07–2.30 (m, 2H), 2.64 (dd, 2H), 2.69–3.19 (m, 4H), 3.33–3.62 (m, 3H), 3.65 (s, 3H), 5.82 (d, 1H), 6.35 (dd, 1H), 6.72 (dd, 1H), 7.63–7.88 (m, 4H), 7.93 (dd, 1H), 8.05 (d, 1H), 8.16 (m, 2H), 8.30 (d, 1H), 8.42 (s, 1H), 8.71 (s, 1H), 8.75 (d, 1H), 9.08 (br, 1H), 9.53 (br, 1H) (FIG. 8).

FIG. 8

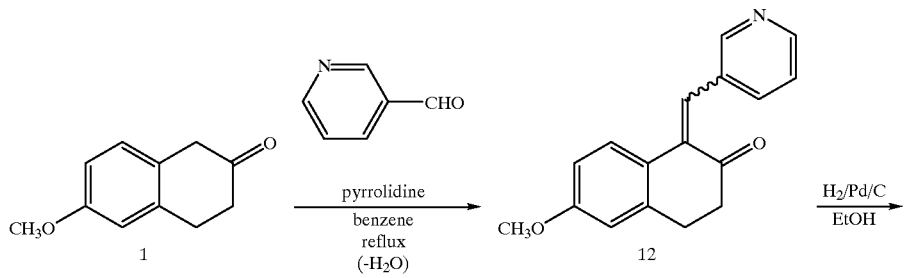

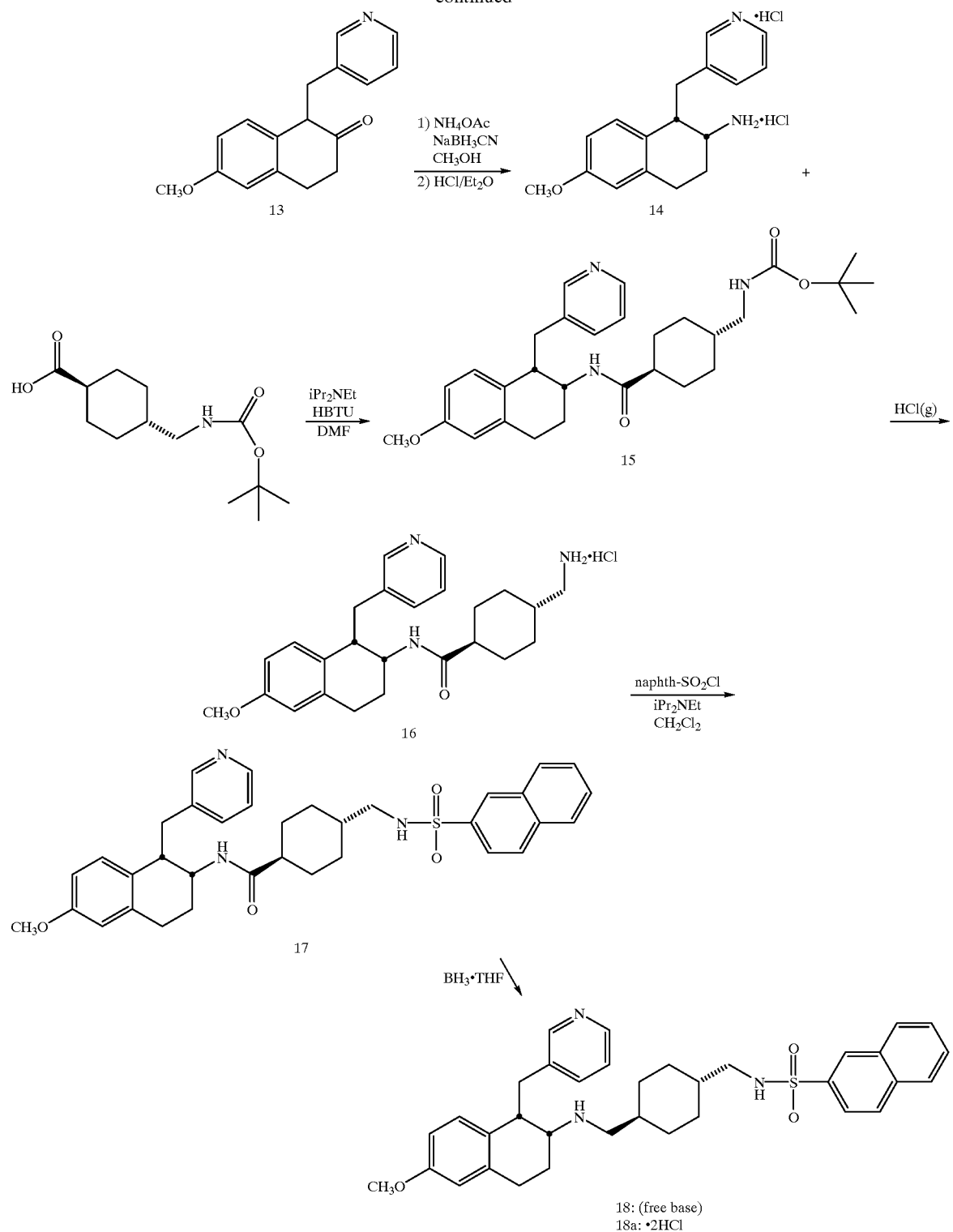

Example 4
rac-[1α,2α(trans)]-N-[[[[[1,2,3,4-tetrahydro-6-fluoro-1-(3-phenylmethyl)-2-naphthalenyl]amino]methyl]-4-cyclohexyl]methyl]2-fluorobenzenesulfonamide (26)

A. 3,4-Dihydro-6-fluoro-2(1H)-naphthalenone was prepared using a modified procedure of Stjernlof, P.; et. al. (*J. Med. Chem.* 1995, 38, 2202). A solution of 4-fluorophenylacetic acid (10.0 g, 64.9 mmol) and thionyl chloride (11.8 mL, 0.162 mol) in 1,2-dichloroethane (150 mL) was heated at reflux for 4 h, in a 500 mL round-bottom flask. The solvent was evaporated in vacuo. The residue was dissolved in 1,2-dichloroethane and the solvent evaporated in vacuo (in order to remove excess thionyl chloride). The residue was dissolved in dichloromethane (50 mL) and the solution was added dropwise, over 20 min, to a cooled suspension of aluminum chloride (21.6 g, 162 mmol) in dichloromethane (250 mL) at −10 to −5° C. The suspension was stirred at −10° C. for 10 min. Ethylene was bubbled rapidly through the suspension for 20 min at −10 to 5° C. Bubbling was continued at a very slow rate for the next 2 h while maintaining a temperature of −5° C. The reaction mixture was quenched with ice (100 g), and the organic layer was separated and washed twice with water and once with a saturated aqueous sodium bicarbonate solution. The organic solution was dried over magnesium sulfate and the solvent was evaporated in vacuo to give the crude tetralone (13.2 g), as a yellow solid. The tetralone was used without purification in the subsequent reaction although a portion of the crude product was recrystallized from hexanes to give purified 3,4-dihydro-6-fluoro-2(1H)-naphthalenone as a colorless solid (-50% recovery). $^1$H NMR (CDCl$_3$) δ2.55 (t, 2H), 3.05 (t, 2H), 3.54 (s, 2H), 6.85–6.97 (m, 2H) and 7.05–7.12 (m, 1H).

B. Pyrrolidine (1.78 mL, 21.4 mmol) was added to a solution 3,4-dihydro-6-fluoro-2(1H)-naphthalenone (3.2 g, 19.5 mmol) in benzene (40 mL) in a 100 mL round-bottom flask and the resultant solution was stirred at room temperature for 1 h. The solvent was evaporated in vacuo. The residue was dissolved in 1,2-dichloroethane and the solvent was evaporated in vacuo (to remove excess pyrrolidine). The crude product, 6-fluoro-2-(pyrrolidin-1-yl)-3,4-dihydronaphthalene 19 was used without purification in the subsequent step.

C. Benzyl bromide (2.8 mL, 23.4 mmol) was added to a solution of the crude enamine 19 (19.5 mmol) in acetonitrile (60 mL) in a 100 mL round-bottom flask and the resultant solution was stirred at room temperature for 1.5 h. The solvent was evaporated in vacuo and the residue was crystallized from hot tetrahydrofuran. The suspension was cooled and the iminium salt 20 was collected by filtration to give a white solid, 4.4 g (58%). MS m/e (M$^+$) 308. $^1$H NMR (DMSO-d$_6$): δ1.70–2.03 (m, 4H), 2.91–3.13 (m, 3H), 3.17–3.29 (m, 2H), 3.38–3.61 (m, 2H), 3.81–3.93 (m, 1H), 3.96–4.07 (m, 1H), 4.13-4.27 (m, 1H), 4.52 (t, 1H), 6.87–7.02 (m, 2H), 7.09–7.17 (m, 2H) and 7.20–7.32 (m, 2H).

D. The iminium salt 20 (4.4 g, 11.33 mmol) was mixed with acetic acid (5 mL, 87.3 mmol), dichloromethane (50 mL), water (50 mL) and methanol (100 mL) in a 500 mL round-bottom flask, and stirred at room temperature for 16 h. An organic layer formed and was separated and the aqueous layer was extracted with dichloromethane. The organic extracts were combined, washed twice with water and once with a saturated solution of aqueous sodium bicarbonate, and then dried over magnesium sulfate. The solvent was evaporated in vacuo to give 3,4-dihydro-6-fluoro-1-(phenylmethyl)-2(1H)-naphthalenone 21 as a tan oil, 3.0 g (100%). This material was used without further purification in the subsequent step.

E. A solution of 3,4-dihydro-6-fluoro-1-(phenylmethyl)-2 (1H)-naphthalenone 21 from above (2.9 g, 11.4 mmol) was dissolved in methanol (50 mL) in a 250 mL round-bottom flask. Ammonium acetate (13.2 g, 0.171 mol) was added and the mixture was stirred at room temperature for 10 min. Sodium cyanoborohydride (3.58 g, 57 mmol) was added and the resultant solution was heated at reflux for 1 h. The solvent was evaporated in vacuo, and the residue was treated with aqueous sodium hydroxide (50 mL of a 1 N solution). The product was extracted into dichloromethane (2×50 mL) and washed twice with water and dried over sodium sulfate. The solvent was evaporated in vacuo, and the residue was dissolved in diethyl ether (50 mL) and treated with ethereal hydrochloric acid (15 mL of a 1 N solution) which resulted in the precipitation of a solid. This material was collected by filtration, washed with diethyl ether and dried in vacuo to give cis-1,2,3,4-tetrahydro-6-fluoro-1-(phenylmethyl)-2-naphthalenamine hydrochloride 22 as a pale pink solid (1.6 g, 48%). MS m/e (MH$^+$) 256. $^1$H NMR (DMSO-d$_6$): δ1.96–2.13 (m, 2H), 2.40 (t, 1H), 2.82–3.12 (m, 2H), 3.17 (dd, 1H), 3.28–3.37 (m, 1H), 3.47–3.60 (br m, 1H), 5.98 (m, 1H), 6.62 (m, 1H), 6.98 (m, 1H), 7.08 (d, 2H), 7.18–7.30 (m, 3H), 8.64 (brs, 3H).

F. cis-1,2,3,4-Tetrahydro-6-fluoro-1-(phenylmethyl)-2-naphthalenamine hydrochloride 22 (0.96 g, 3.29 mmol) was dissolved in N,N-dimethylformamide (50 mL) in a 250 mL round-bottom flask with stirring. Diisopropylethylamine (1.30 mL, 7.46 mmol) was added followed by 4-(tert-butoxycarbonyl)aminomethylcyclohexane carboxylic acid (0.85 g, 3.31 mmol). To this stirred solution, HBTU (1.25 g, 3.29 mmol) was added slowly. The flask was flushed with argon, capped, and allowed to stir for 3 hours. At this time the reaction solution was poured into 500 mL water. A precipitate immediately formed and this slurry was stirred overnight. The solid was then filtered and rinsed with additional portions of water. Air was pulled over the solid until nearly dry. This solid was added to methanol (15 mL) and the solid-liquid mixture was heated to reflux for several minutes. After cooling the solution to room temperature, the white solid was filtered away from the orange-brown liquid. The filtrate was evaporated slightly to provide a second batch of white solid which was filtered as before and combined with the first batch. This white solid was dried in vacuo to afford [1α,2α(trans)]-4-[[(tert-butoxycarbonyl)amino]methyl]-N-[1,2,3,4-tetrahydro-6-fluoro-1-(3-phenylmethyl)-2-naphthalenyl]-cyclohexanecarboxamide 23 (1.28 g, 2.59 mmol). MS m/e (MH$^+$) 256. $^1$H NMR(CDCl$_3$): δ0.79–1.00 (m, 2H), 1.23–1.53 (m, 12H), 1.70–2.08 (m, 7H), 2.75–3.03 (m, 6H), 3.37 (m, 1H), 4.29 (m, 1H), 4.55 (m, 1H), 5.33 (d, 1H), 6.67–6.87 (m, 3H), 7.12 (d, 2H), 7.37–7.18 (m, 3H).

G. The carboxamide 23 obtained above (1.28 g, 2.58 mmol) was dissolved in —dioxane (150 mL) in a 250 mL round-bottom flask and cooled in an ice bath. Excess gaseous hydrogen chloride was added to the resultant solid-liquid mixture until saturation. The clear solution was then warmed to room temperature and stirred until the starting material was completely consumed (HPLC). The solvents were removed in vacuo and the resulting solid titurated with diethyl ether to yield a white solid which upon filtration and drying in vacuo afforded [1α, 2α(trans)]-4-(aminomethyl)-N-[1,2,3,4-tetrahydro-6-fluoro-1-(phenylmethyl)-2-naphthalenyl]-cyclohexanecarboxamide hydrochloride 24. MS m/e (MH$^+$) 395; $^1$H NMR (DMSO-d$_6$): δ0.84–1.05 (m, 2H), 1.28–1.49 (m, 2H), 1.50–1.62 (m, 1H), 1.65–2.04 (m, 6H), 2.09–2.27 (m, 1H), 2.51–2.59 (m, 1H), 2.60–2.73 (m, 2H), 2.77–3.04 (m, 3H), 3.12–3.26 (m, 1H), 3.92 (m, 1H), 6.41 (dd, 1H), 6.73 (dt, 1H), 6.89–7.05 (m, 3H), 7.13–7.32 (m, 3H), 7.88 (br, 3H), 7.97 (d, 1H).

H. The naphthalenyl carboxamide 24 (0.087 g, 0.20 mmol) was dissolved in a dichloromethane solution (15 mL) of diisopropylethylamine (0.080 mL, 0.46 mmol) with stirring, in 100 mL round-bottom flask. A solution of 2-fluorobenzenesulfonyl chloride (0.045 g, 0.23 mmol) in dichloromethane (15 mL) was added. The reaction mixture was allowed to stir overnight at room temperature. The solvent was removed in vacuo to give a glassy colorless material. This material was dissolved in dichloromethane (100 mL) and the solution was washed with 0.1 M sodium hydroxide solution (2×55 mL) and then with water (1×50 mL). The organics were dried over magnesium sulfate, filtered, and the solvents removed in vacuo to yield [1α,2α(trans)]-4-[[(2-fluorobenzenesulfonyl)amino]methyl]-N-[1,2,3,4-tetrahydro-6-fluoro-1-(phenylmethyl)-2-naphthalenyl]-cyclohexanecarboxamide 25 (0.110 g, 0.199 mmol) as a tan powder. MS m/e (MH$^+$) 553; $^1$H NMR (DMSO-d$_6$): δ0.71–0.91 (m, 2H), 1.18–1.43 (m, 3H), 1.61–1.81 (m, 5H), 1.85–2.00 (m, 1H), 2.03–2.19 (m, 1H), 2.51 (m, 1 H, obscured by DMSO), 2.71 (t, 2H), 2.79–3.03 (m, 3H), 3.08–3.24 (m, 1H), 3.91 (m, 1H), 6.42 (dd, 1H), 6.72 (dt, 1H), 6.86–7.02 (m, 3H), 7.08–7.29 (m, 3H), 7.33–7.52 (m, 2H), 7.65–7.77 (m, 1H), 7.79 (dt, 1H), 7.84–7.99 (m, 2H).

I. The carboxamide 25 obtained above (0.110 g, 0.199 mmol) was dissolved in THF (15 mL) and with stirring, a solution of borane-tetrahydrofuran complex solution (1 M in THF, 2.0 mL, 2.0 mmol) was added. The solution was flushed with nitrogen and then heated at reflux for about 1 hour. After cooling to room temperature, water (2 mL) was added dropwise to the solution with stirring and the solvents were removed in vacuo to give a white film. Hydrochloric acid (15 mL of a 6 M solution) was added to this material and the mixture was heated at reflux for approximately 30 minutes. After cooling to room temperature sodium hydroxide (100 mL of a 1 N solution) was added. This aqueous mixture was extracted with dichloromethane (3×100 mL). The organic extracts were combined and dried over magnesium sulfate, filtered, and the solvents were removed in vacuo. The residue was dissolved in THF (4 mL) and ethereal hydrogen chloride (2 mL of a 1 M solution) was added. The solvents were removed in vacuo to give a white gelatinous solid. Methanol and dichloromethane were added to break up the solid and then removed in vacuo to give a white powder. Isopropanol (4 mL) was added and the slurry was briefly heated at reflux then cooled. The solvent was removed and the moist product was dried under vacuum to afford [1α,2α(trans)]-N-[[[[[1,2,3,4-tetrahydro-6-fluoro-1-(3-phenylmethyl)-2-naphthalenyl]amino]methyl]-4-cyclohexyl]methyl]2-fluorobenzenesulfonamide 26 (0.087 g, 0.151 mmol) as a white powder. MS m/e (MH$^+$) 539; $^1$H NMR (DMSO-d$_6$): δ0.71–1.03 (m, 4H), 1.24–1.43 (m, 1H), 1.61–1.97 (m, 5H), 2.03–2.25 (m, 2H), 2.44 (m, 1H), 2.73 (t, 2H), 2.83–3.18 (m, 5H), 3.40–3.59 (m, 2H), 5.96 (dd, 1H), 6.59 (dt, 1H), 6.98 (dd, 1H), 7.07 (d, 2H), 7.17–7.32 (m, 3H), 7.36–7.53 (m, 2H), 7.73 (q, 1H), 7.81 (dt, 1H), 7.98 (t, 1H), 8.85 (br, 2H) (FIG. 9).

FIG. 9

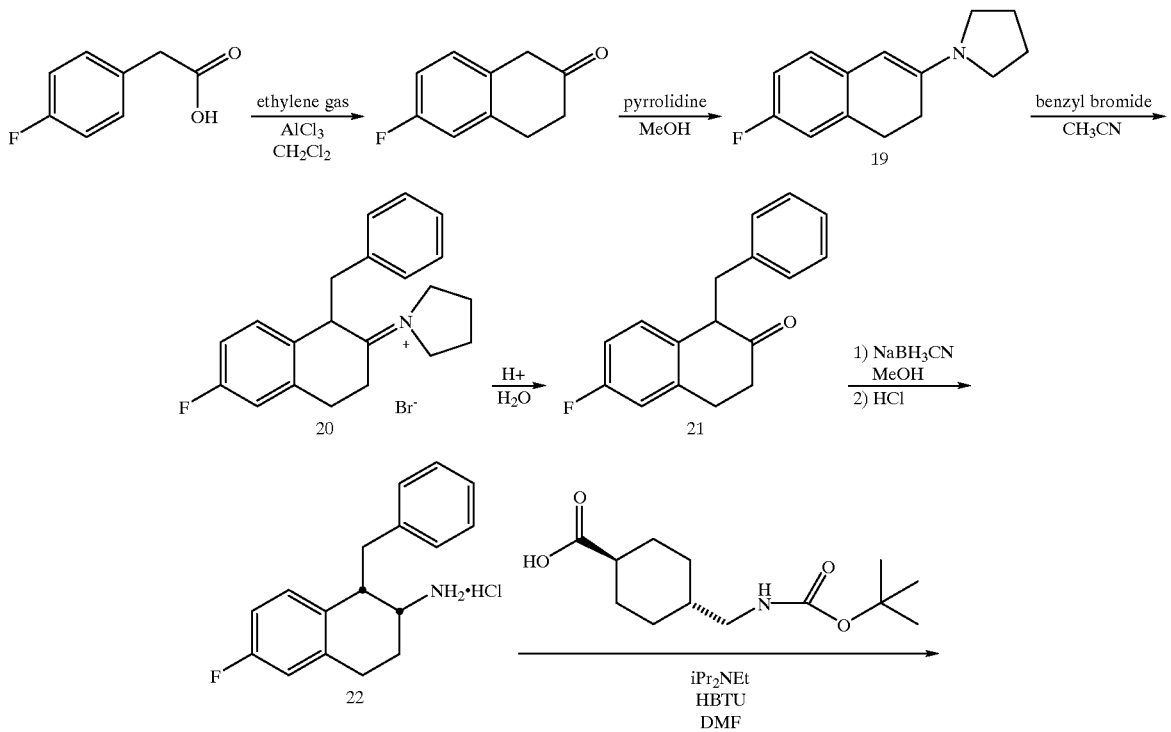

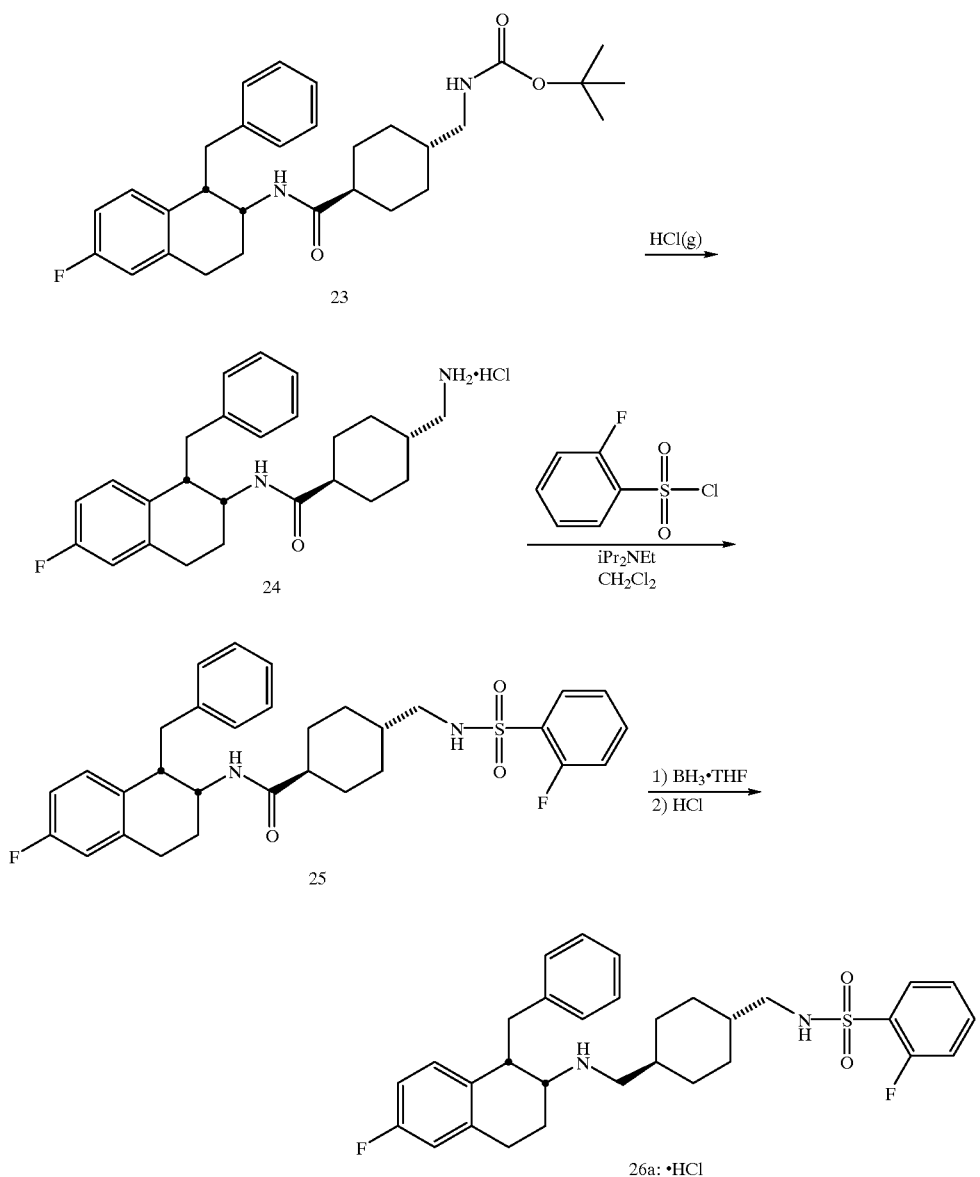

Example 5 rac-[1α,2α(trans)]-N-[[[[[1,2,3,4-tetrahydro-6-fluoro-1-phenyl-2-naphthalenyl]amino]methyl]-4-cyclohexyl]methyl]2-naphthlenesulfonamide (34)

A. A solution of phenylmagnesium bromide in diethyl ether (3.0 M, 23 mL, 69 mmol) was added dropwise to a solution of 6-methoxy-1,2,3,4-tetrahydronaphthalen-1-one 27 (10.0 g, 56.7 mmol) in diethyl ether (100 mL) at room temperature. The reaction mixture was heated at reflux for 1.5 h. An additional portion of phenylmagnesium bromide solution (10 mL, 60 mmol) was added to the cooled reaction mixture, and the resultant mixture was heated at reflux for an additional 2.5 h. The cooled mixture was poured into a saturated solution of ammonium chloride (200 mL), and stirred for 15 min. The organic layer was separated, washed with a saturated solution of sodium chloride, and dried over magnesium sulfate. The solvent was evaporated in vacuo, and the resultant oil was treated with a solution of sulfuric acid (8 mL) in acetic acid (30 mL) at room temperature for 1.5 h. Ice water (300 mL) was added to the solution, and the product was extracted into dichloromethane (200 mL), washed with water, and a saturated aqueous solution of sodium bicarbonate, and dried over magnesium sulfate. The solvent was evaporated in vacuo and the residue was purified by medium pressure chromatography using ethyl acetate 0 to 3% in hexanes as the eluent, to give the 6-methoxy-1-phenyl-3,4-dihydronaphthalene 28 in two crops 4.0 g (29%) and an impure fraction 5.02 g (37%) as an oil.

B. Borane in tetrahydrofuran (34 mL of a 1M solution, 34 mmol) was added to tetrahydrofuran (50 mL) and the resultant solution was cooled to 0° C. A solution of 6-methoxy-1-phenyl-3,4-dihydronaphthalene 28 (5.0 g, 21.2 mmol) in tetrahydrofuran (10 mL) was added. The resultant mixture was stirred at ambient temperature for 18 h. A solution of water (5 mL) in tetrahydrofuran (20 mL) was slowly added to the cooled solution which resulted in considerable foaming. Additional water (10 mL) was added followed by 10% aqueous sodium hydroxide (15 mL) and 30% hydrogen peroxide (30 mL). The resultant mixture was stirred at room temperature for 6 h. The organic layer was separated and the aqueous layer was extracted with diethyl ether (2×50 mL). The combined organic solutions were washed with a saturated aqueous sodium chloride and dried over magnesium sulfate. The solvent was evaporated in vacuo, and the residue was purified by flash chromatography using 30 to 40% ethyl acetate in hexanes as the eluent, to afford trans-6-methoxy-1-phenyl-1,2,3,4-tetrahydronaphthalen-2-ol 29 as an oil (2.0 g, 37%). $^1$H NMR(CDCl$_3$) δ1.77 (d, 1H), 1.83–1.97 (m, 1H), 2.13–2.22 (m, 1H), 2.94–3.05 (m, 2H), 3.78 (s, 3H), 3.90 (d, 1H), 3.98–4.07 (m, 1H), 6.59–6.70 and 7.16–7.39 (m, 8H).

C. A solution of para-toluenesulfonyl chloride (1.8 g, 9.43 mmol) in dichloromethane (10 mL) was added to a solution of trans-6-methoxy-1-phenyl-1,2,3,4-tetrahydronaphthalen-2-ol 29 (2.0 g, 7.86 mmol), N,N-diisopropylethylamine (4.8 mL, 27.5 mmol) and 4-dimethylaminopyridine (1.15 g, 9.43 mmol) in dichloromethane (40 mL) at 0C. The resultant solution was stirred at ambient temperature for 16 h. The solution was washed successively with 1 N aqueous sodium hydroxide (×2) and a saturated aqueous solution of sodium chloride, then dried over sodium sulfate. The solvent was evaporated in vacuo to give crude trans-6-methoxy-1-phenyl-2-(4-methylbenzenesulfonyl)oxy-1,2,3,4-tetrahydronaphthalene 30 (3.47 g), as a pale yellow solid which was used without further purification in the subsequent step. $^1$H NMR(CDCl$_3$) δ1.90–2.04 (m, 1H), 2.14–2.24 (m, 1H), 2.42 (s, 3H), 2.83–3.07 (m, 2H), 3.77 (s, 3H), 4.16 (d, 1H), 4.80–4.87 (m, 1H), 6.60–6.67 (m, 3H), 6.82–6.90 (m, 2H), 7.13–7.23 (m, 5H), 7.58 (d, 2H).

D. A N,N-dimethylformamide solution (50 mL) of crude trans-6-methoxy-1-phenyl-2-(4-methylbenzenesulfonyl)oxy-1,2,3,4-tetrahydronaphthalene 30 (3.4 g), sodium azide (3.78 g, 58.3 mmol) and 15-crown-5 (6.61 mL, 33.2 mmol) was heated at 75° C. for 7 h. The reaction mixture was poured into ice water (200 mL), and the product was extracted into diethyl ether (3×50 mL). The organic extracts were combined and washed successively with water (4×100 mL) and a saturated aqueous solution of sodium chloride, and dried over sodium sulfate. The solvent was evaporated in vacuo, and the remaining residue was purified by medium pressure chromatography using 3% ethyl acetate in hexanes as the eluent to give crude cis-2-azido-6-methoxy-1-phenyl-1,2,3,4-tetrahydronaphthalene 31 (1.35 g, ~62%) as an oil which was used without further purification in the subsequent step.

E. The azido-tetrahydronaphthalene 31 obtained above (1.3 g) was dissolved in isopropanol (50 mL) and this solution was hydrogenated at 50 psi over 10% palladium on carbon (0.2 g) at room temperature for 18 h. The catalyst was removed by filtration and the solvent was evaporated in vacuo to afford crude cis-1,2,3,4-tetrahydro-6-methoxy-1-phenyl-2-naphthalenamine 32 as an oil, which was used in the subsequent step without purification (FIG. 10). MS m/e (MH$^+$) 254.

F. A solution of isobutylchloroformate (0.88 mL, 6.76 mmol) in dichloromethane (5 mL) was added dropwise to a solution of trans-4-(2-napthylsulfonamido)methylcyclohexanecarboxylic acid (1.12 g, 3.22 mmol) and triethylamine (1.35 mL, 9.66 mmol) in dichloromethane (30 mL) at 0° C. The resultant solution was stirred at room temperature for 1 h. A solution of naphthalenamine 32 (4.65 mmol) in dichloromethane was added dropwise to the reaction mixture at 0° C. The reaction was stirred at ambient temperature for 16 h after which time, solvents and other volatile materials were evaporated in vacuo. The resultant residue was treated with a solution of 1 N aqueous sodium hydroxide (20 mL) and tetrahydrofuran (20 mL) for 30 min. The solution was concentrated in vacuo and acidified with 1N aqueous hydrochloric acid (30 mL). The product was extracted into 10% isopropanol in dichloromethane (2×50 mL). The solvent was evaporated in vacuo and the residue was purified by medium pressure chromatography using 2% methanol in dichloromethane as the eluent, to give [1α,2α (trans)]-4-[[(2-naphthalenylsulfonyl)amino]methyl]-N-[1,2,3,4-tetrahydro-6-methoxy-1-phenyl-2-naphthalenyl]-cyclohexanecarboxamide 33 (0.95 g, 52%) as a glass, which was crystallized from diethyl ether to give a colorless solid (0.38 g, 20%). MS m/e (MH$^+$) 583; $^1$H NMR(DMSO-d$_6$) δ0.68–0.83 (m, 2H), 1.20–1.37 (m, 3H), 1.50–1.77 (m, 6H), 1.87–1.99 (m, 1H), 2.60 (t, 2H), 2.90–3.02 (m, 2H), 3.73 (s, 3H), 3.94–4.07 (m, 1H), 4.40 (d, 1H), 6.61–6.81 (m, 5H), 7.14–7.32 (m, 4H), 7.63–7.75 (m, 3H), 7.81 (d, 1H), 8.04 (d, 1H), 8.14 (t, 2H) and 8.43 (s, 1H).

G. A 1 M solution of borane in tetrahydrofuran (5 mL, 5 mmol) was added dropwise to a solution of carboxamide 33 (0.25 g, 0.43 mmol) in tetrahydrofuran (15 mL) and stirred at ambient temperature for 5 h. Water (5 mL) in tetrahydrofuran (15 mL) was added dropwise to the solution at 0° C. over 10 min. Hydrochloric acid (5 mL of a 4 N solution) was added to the solution, and the resultant mixture was stirred at 0° C for 16 h. The reaction mixture was concentrated in vacuo, and neutralized with aqueous sodium bicarbonate. The product was extracted into dichloromethane (2×50 mL). The organic extracts were combined and the solvent was evaporated in vacuo. The resultant residue was purified by preparative reverse phase HPLC using 0.1% trifluoroacetic acid in acetonitrile and water as the eluent. The product eluted at 55% acetonitrile to afford the trifluoroacetic acid salt of [1α,2α(trans)]-N-[[[[1,2,3,4-tetrahydro-6-methoxy-1-phenyl-2-naphthalenyl]amino]methyl]-4-cyclohexyl]methyl]2-naphthlenesulfonamide 34 as a colorless solid (0.125 g, 43%). MS (MH$^+$) 569; 1H NMR(DMSO-d$_6$) δ0.73–0.90 (m, 4H), 1.23–1.36 (m, 1H), 1.40–1.57 (m, 1H), 1.60–1.75 (m, 4H), 1.83–2.09 (m, 2H), 2.60 (t, 2H, collapses to d with D$_2$O), 2.64–2.77 (m, 1H), 2.87–3.16 (m, 3H), 3.62–3.76 (m, 1H), 3.73 (s, 3H), 4.58 (d, 1H), 6.68 (dd, 1H), 6.76–6.80 (m, 2H), 7.13 (d, 2H), 7.24–7.37 (m, 3H), 7.67–7.77 (m, 3H, collapses to 2H with D$_2$O), 7.83 (d, 1H), 7.87–8.00 (br s, 1H, exchanges with D$_2$O), 8.06 (d, 1H), 8.10–8.26 (m, 3H) and 8.43 (s, 1H). (FIG. 11).

FIG. 10
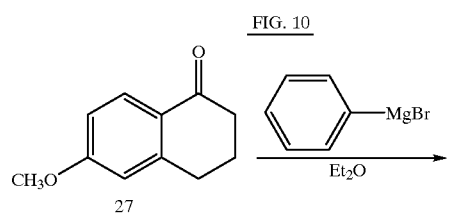
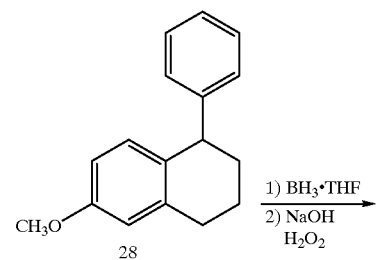
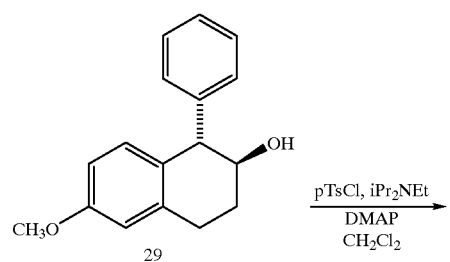
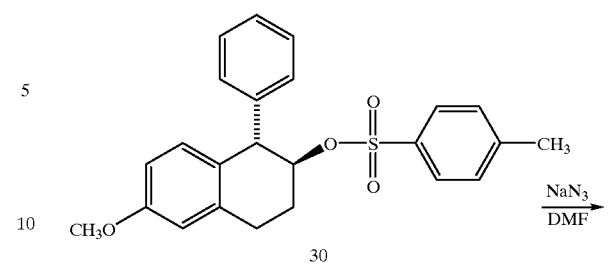
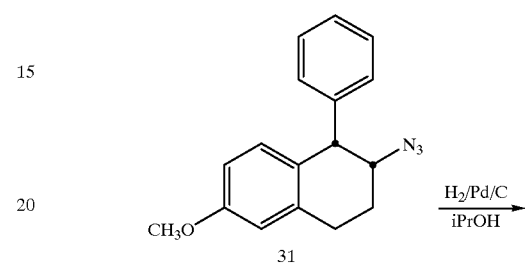
FIG. 11
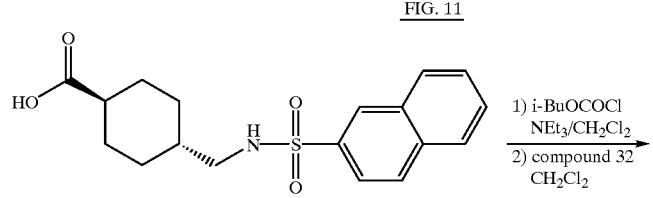
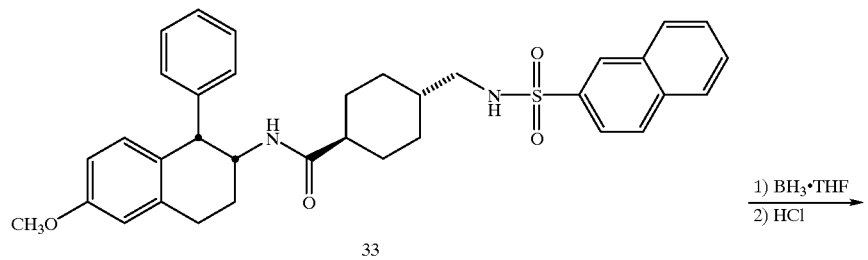

Example 6 rac-[1α,2α(trans)]-N-[[[[[1,2,3,4-tetrahydro-6-methoxy-1-(1-propene-3-yl)-2-naphthalenyl]amino]methyl]4-cyclohexyl]methyl] benzenesulfonamide (39)

A. 3,4-Dihydro-6-methoxy-2-(pyrrolidin-1-yl) naphthalene 2 was prepared by reacting a solution of 6-methoxy-β-tetralone (4.73 g, 26.8 mmol) in methanol (50 mL) with pyrrolidine (2.35 mL, 28.18 mmol) in a 100 mL round-bottom flask at room temperature for 30 min. The solvent, was evaporated in vacuo to afford the desired enamine 2 as a yellow solid (a single component by reverse phase HPLC), which was used without purification in the subsequent step.

B. Enamine 2 (26.8 mmol) was dissolved in acetonitrile (50 mL) in 100 mL round-bottom flask and allyl bromide (2.55 mL, 29.5 mmol) was added. After stirring at room temperature for 18 h, the solvent was evaporated in vacuo and the resultant residue was titurated with tetrahydrofuran. The corresponding iminium salt 35 was collected by filtration as a gummy solid and used without further purification in the subsequent step. The product is a single component by reverse phase HPLC. MS (M$^+$) 270. $^1$H NMR (CDCl$_3$): δ2.00–2.15 (m, 4H), 2.33–2.47 (m, 1H), 2.60–2.70 (m, 1H), 2.90–3.34 (m, 2H), 2.90–3.34 (m, 4H), 3.76 (m, 3H), 3.84–4.16 (m, 3H), 4.23–4.39 (m, 2H), 5.04 (d, 1H), 5.07 (s, 1H), 5.70–5.83 (m, 1H), 6.84 (d, 1H), 6.92 (s, 1H) and 7.14 (d, 1H).

C. The iminium salt 35 from above (26.8 mmol) was mixed with acetic acid (4 mL), dichloromethane (40 mL), methanol (80 mL) and water (40 mL) in a 250 mL round-bottom flask and stirred at room temperature for 18 h. The mixture separated into two phases and the organic phase was separated. The aqueous phase was extracted with dichloromethane. The organic extracts were combined, washed twice with water and once with saturated aqueous sodium bicarbonate and dried over magnesium sulfate. The solvents was evaporated in vacuo to give 3,4-dihydro-6-methoxy-1-(1-propene-3-yl)-2(1H)-naphthalenone 36 as an oil, a single component by HPLC (>95%), 2.5 g (46% from 2). $^1$H NMR (CDCl$_3$): δ2.52–2.70 (m, 4H), 2.92–3.15 (m, 2H), 3.45 (t, 1H), 3.81 (s, 3H), 4.97 (s, 1H), 5.03 (d, 1H), 5.65–5.81 (m, 1H), 6.74–6.82 (m, 2H) and 7.08 (d, 1H).

D. A solution of crude naphthalenone 36 (2.5 g, 11.6 mmol) in methanol (50 mL) was treated with ammonium acetate (13.4 g, 0.173 mol) in a 100 mL round-bottom flask and stirred at room temperature for 10 min. Sodium cyanoborohydride (3.58 g, 57 mmol) was added and the resultant solution was heated at reflux for 3 h. The solvent was evaporated in vacuo, and the residue was treated with aqueous sodium hydroxide (50 mL of a 1 N solution). The product was extracted into dichloromethane (2×50 mL). The organic extracts were combined, washed with water and dried over sodium sulfate. The solvent was evaporated in vacuo, and the residue was dissolved in diethyl ether (50 mL) and methanol (1–2 mL). The resultant solution was treated with ethereal hydrochloric acid (14 mL of a 1 N solution) to produce a gummy solid that coated the sides of the flask. The solvent was decanted and an additional 50 mL of ether was added, at which point the residue solidified. The product was collected by filtration, washed with diethyl ether and dried in vacuo to give cis-1,2,3,4-tetrahydro-6-methoxy-1-(1-propene-3-yl)-2-naphthalenamine hydrochloride 37a as a purple solid (1.75 g, a mixture of 2 components -3:1 by HPLC). MS m/e (MH$^+$) 218.

E. A solution of trans-4-[(benzenesulfonamido)methyl] cyclohexanecarboxylic acid (0.924 g, 3.31 mmol), 2-(1H-benzotriazole-1-yl)-1,1,3,3-tetramethyluronium hexafluorophosphate (HBTU), (1.26 g, 3.31 mmol) and N,N-diisopropylethylamine (1.7 mL, 9.77 mmol) in N,N-dimethylformamide (10 mL) was stirred at room temperature in a 50 mL round-bottom flask for 15 min. Naphthalenamine hydrochloride 37a (0.80 g, 3.15 mmol) was added to the solution. Stirring was continued for an additional hour, and the resultant solution was poured into water (~100 mL). A gummy solid formed on the sides of the flask. Ethanol was added and the product crystallized upon heating. The mixture was cooled to room temperature and the product was collected by filtration and dried in vacuo, to give [1α,2α(trans)]-4-[[(benzenesulfonyl)amino]methyl]-N-[1,2,3,4-tetrahydro-6-methoxy-1-(1-propene-3-yl)-2-naphthalenyl]-cyclohexanecarboxamide 38 a light gray solid, 0.67 g (43%), a single component by HPLC. MS (MH$^+$) 497; $^1$H NMR (CDCl$_3$): δ0.71–0.97 (m, 2H), 1.33–1.50 (m, 3H), 1.74–1.98 (m, 7H), 2.24–2.53 (m, 2H), 2.76–2.87 (m, 4H), 3.00–3.09 (m, 1H), 3.78 (s, 3H), 4.34–4.43 (m, 1H), 4.62 (t, H), 5.02 (s, 1H), 5.07 (d, 1H), 5.48 (d, 1H), 5.81–5.96 (m, H), 6.63 (s, 1H), 6.72 (d, 1H), 7.02 (d, 1H), 7.47–7.62 (m, 3H) and 7.84 (d, 2H).

F. A solution of lithium aluminum hydride in tetrahydrofuran (4 mL of a 1.0 M solution, 4 mmol) was carefully added to a solution of carboxamide 38 (0.21 g, 0.422 mmol) in tetrahydrofuran (10 mL) in a 50 mL round-bottom flask. The resultant solution was heated at reflux for 24 h. The solution was cooled in a water bath, and the excess hydride was quenched by careful addition of water (0.16 mL) in tetrahydrofuran (5 mL) followed by 15% aqueous sodium hydroxide (0.16 mL) in tetrahydrofuran (5 mL) and finally water (0.5 mL). The inorganic solids were removed by filtration and washed generously with tetrahydrofuran. The filtrate was evaporated in vacuo and the resulting residue was dissolved in ethanol and treated with a saturated solution of hydrochloric acid in ethanol (2 mL). Evaporation and tituration with diethyl ether afforded [1α,2α(trans)]-N-[[[[[1,2,3,4-tetrahydro-6-methoxy-1-(1-propene-3-yl)-2-naphthalenyl]amino]methyl]-4-cyclohexyl]methyl]-benzenesulfonamide hydrochloride 39a as a colorless solid, 0.118 g (54%), a single component by HPLC (>95%). MS (MH$^+$) 483; $^1$H NMR (DMSO-d$_6$) δ0.75–1.04 (m, 4H), 1.23–1.40 (m, 1H), 1.57–2.16 (m, 7H), 2.43–2.62 (m, 2H), 2.79–3.00 (m, 4H), 3.13–3.23 (m, 1H), 3.35–3.44 (m, 2H), 3.73 (s, 3H), 4.91 (d, 1H), 5.03 (d, 1H), 5.73–5.88 (m, 1H), 6.65–6.72 (m, 2H), 6.93 (d, 1H), 7.57–7.70 (m, 4H), 7.84 (d, 2H), 8.70 (br s, 1H, exchanges with D$_2$O),and 9.07 (br s, 1H, exchanges with D$_2$O). (FIG. 12).

FIG. 12

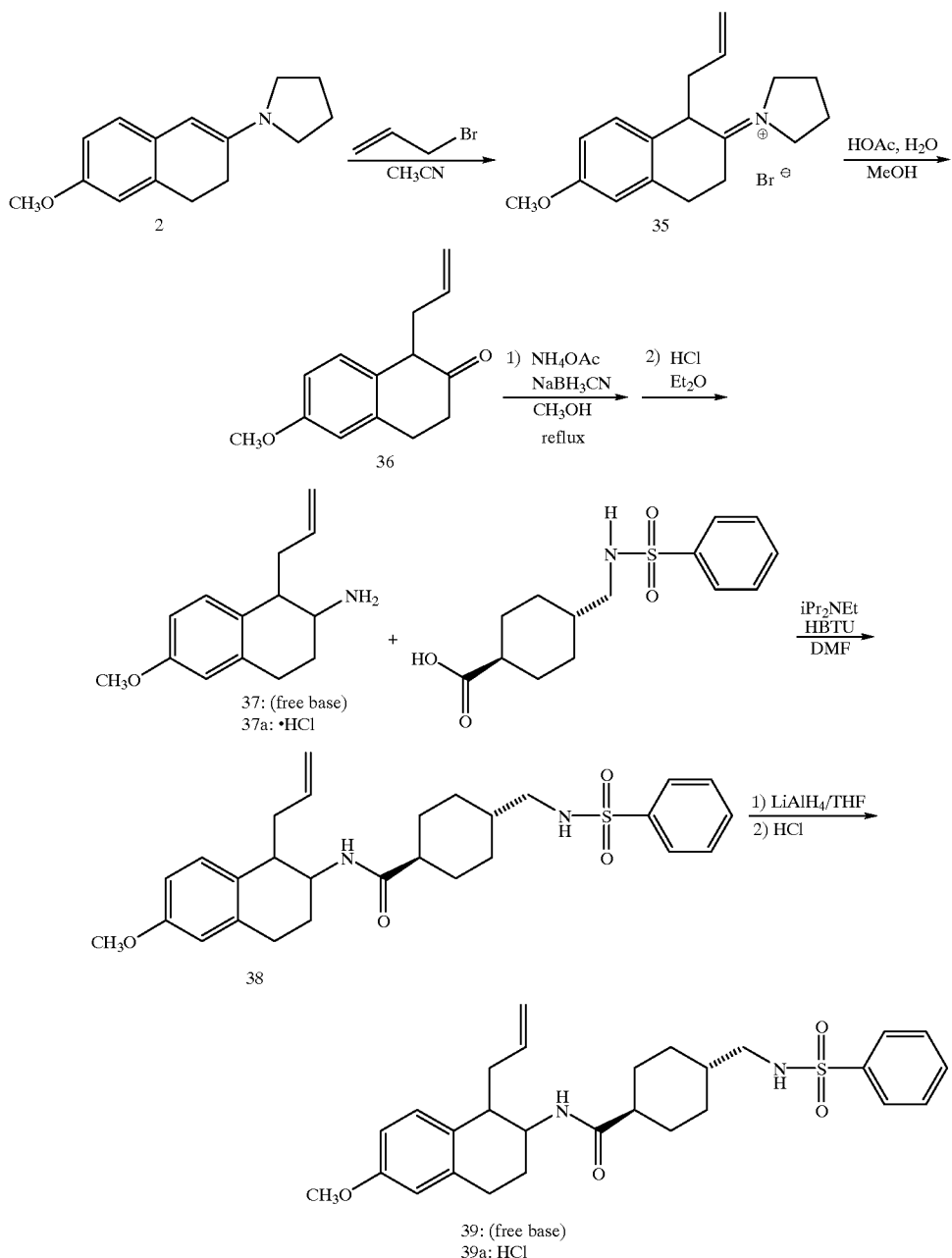

Example 7 rac-[1α,2α(trans)]-N-[[[[[1,2,3,4-tetrahydro-6-methoxy-1-(3-hydroxypropyl)-2-naphthalenyl]amino]methyl]-4-cyclohexyl]methyl] benzenesulfonamide (40)

A solution of borane (3.5 mL of a 1.0 M solution, 3.5 mmol) in tetrahydrofuran was added to a solution of carboxamide 38 (0.25 g, 0.503 mmol) in tetrahydrofuran (10 mL) in a 100 mL round-bottom flask. The resultant mixture was heated at reflux for 1 h. Water (1.5 mL) was carefully added and the mixture was heated at reflux for 1 h. Aqueous sodium hydroxide (50%, 0.5 mL) was added followed by hydrogen peroxide (30%, 1.0 mL). The two phase system was stirred vigorously for 2 h. The organic layer was separated, and the aqueous layer was extracted with dichloromethane. The organic extracts were combined, dried over sodium sulfate, and the solvent was evaporated in vacuo. The residue was dissolved in ethanol and treated with a saturated solution of hydrogen chloride in ethanol (2 mL). The solvent was evaporated and the residue was titurated with diethyl ether to give [1α,2α(trans)]-N-[[[[[1,2,3,4-tetrahydro-6-methoxy-1-(3-hydroxypropyl)-2-naphthalenyl]amino]methyl]-4-cyclohexyl]methyl] benzenesulfonamide hydrochloride 40 as a white solid 0.242 g (90%). The purity by HPLC is 80–90%. MS (MH$^+$) 501; $^1$H NMR (DMSO-d$_6$) δ 0.75–0.97 (m, 4H), 1.02–1.13 (m, 1H), 1.16–1.51 (m, 5H), 1.58–2.18 (m, 8H), 2.54–2.63 (m, 2H), 2.73–3.12 (m, 4H), 3.28–3.46 (m, 3H), 3.72 (s, 3H), 6.64–6.73 (m, 2H), 6.97 (d, 1H), 7.54–7.69 (m, 4H), 7.80 (d, 2H), 8.57 (br s, 1H, exchanges with $D_2O$),and 8.93 (br s, 1H, exchanges with $D_2O$) (FIG. 13).

Example 8
rac-[1α,2α(trans)]-N-[[[[[1,2,3,4-tetrahydro-6-methoxy-1-(n-propyl)-2-naphthalenyl]amino]methyl]-4-cyclohexyl]methyl] benzenesulfonamide (42)

A. The carboxamide 38 (0.4 g, 0.805 mmol) was dissolved in methanol/dioxane (20 mL/20 mL) and hydrogenated (55 psi) over 10% palladium on carbon (catalytic) for 18 h. The catalyst was removed by filtration, and the solvent was evaporated in vacuo to give [1α,2α(trans)]-4-[[(benzenesulfonyl)amino]methyl]-N-[1,2,3,4-tetrahydro-6-methoxy-1-(n-propyl)-2-naphthalenyl]-cyclohexanecarboxamide 41 as an off white solid (0.5 g, one component by HPLC). MS (MH$^+$) 499. 1 H (DMSO-d$_6$) δ0.75–0.92 (m, 7H), 1.22–2.17 (m, 11H), 2.13 (m, 1H), 2.57 (t, 2H), 2.67–2.88 (m, 3H), 3.70 (s, 3H), 3.90–4.03 (m, 1H), 4.16 (d, 1H), 6.62–6.73 (m, 2H), 6.97 (d, 1H), 7.56– 7.74 (m, 4H) and 7.80 (d, 2H); NMR also shows an unidentified impurity. This material was used without purification in the subsequent step.

B. A solution of borane in tetrahydrofuran (4.0 mL of a 1.0 M solution, 4.0 mmol) was added to a solution of the crude carboxamide 41 (0.43 g, 0.86 mmol) in tetrahydrofuran (10 mL). The resultant mixture was heated at reflux for 1 h. Water (1.5 mL) was slowly added to the cooled solution, which resulted in considerable foaming. Concentrated aqueous hydrogen chloride (0.75 mL) was added and the solution was heated to reflux for 1 h. The solution was concentrated and the pH adjusted to 7–8 with aqueous sodium hydroxide (1N). The resultant solid was collected by filtration and washed with water. This material was dissolved in ethanol and treated with a saturated solution of hydrogen chloride in ethanol. The hydrogen chloride salt of the product crystallized from the solution and was collected by filtration, washed with diethyl ether and dried in vacuo to give [1α,2α(trans)]-N-[[[[[1,2,3,4-tetrahydro-6-methoxy-1-(n-propyl)-2-naphthalenyl]amino]methyl]-4-cyclohexyl]methyl] benzenesulfonamide 42 as a colorless solid (0.147 g, a single component by HPLC). The mother liquors were evaporated, and the resultant residue titurated with diethyl ether to yield an additional 0.120 g of product. MS (MH$^+$) 485; $^1$H NMR (DMSO-d$_6$) δ0.75–0.96 (m, 7H), 1.12–1.37 (m, 4H), 1.56–2.16 (m, 7H), 2.58 (t, 2H), 2.54–2.63 (m, 2H), 2.72–3.09 (m, 5H), 3.24–3.36 (m, 1H), 3.71 (s, 3H), 6.65–6.74 (m, 2H), 6.96 (d, 1H), 7.56–7.68 (m, 4H), 7.80 (d, 2H), 8.56 (br s, 1 H, exchanges with $D_2O$),and 8.95 (br s, 1 H, exchanges with $D_2O$) (FIG. 13).

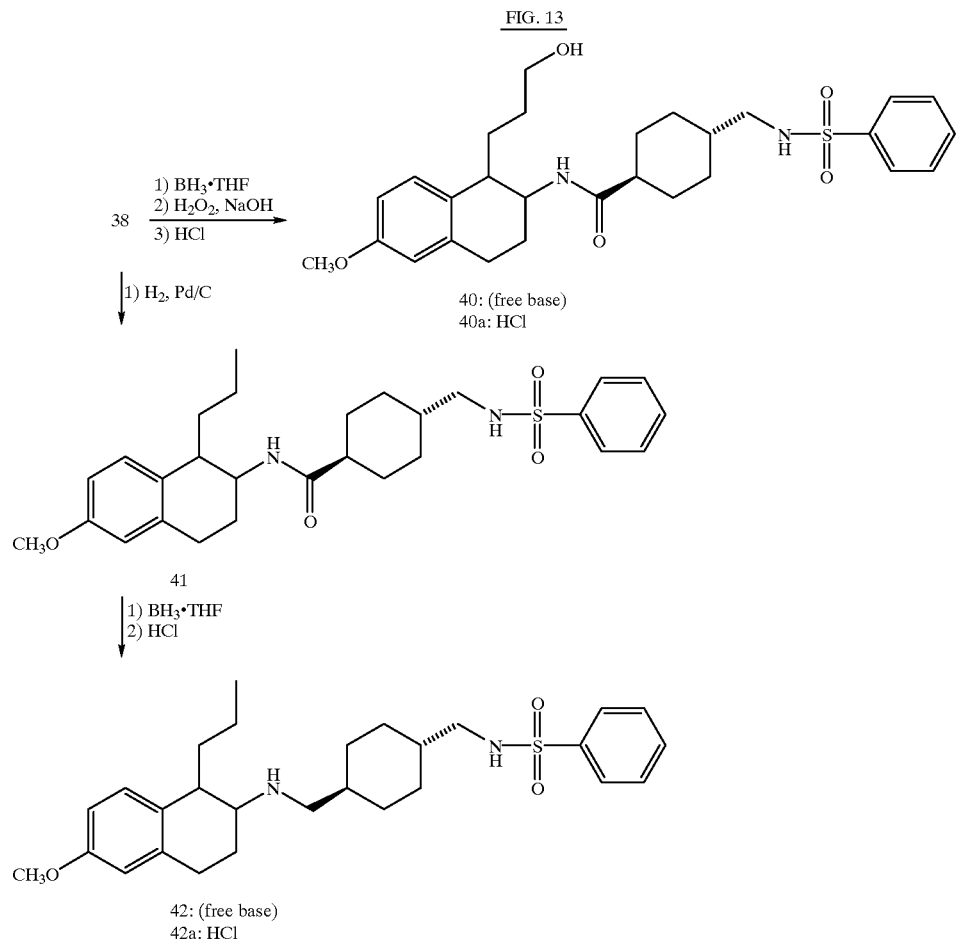

FIG. 13

Example 9
rac-[1α,2α(trans)]-N-[[[[[1,2,3,4-tetrahydro-6-hydroxy-1-(3-pyridinylmethyl)-2-naphthalenyl]amino]methyl]-4-cyclohexyl]methyl]2-fluorobenzenesulfonamide (44)

The bis-amine salt of the starting material 43 (0.109 g, 0.174 mmol) was put into a 100 mL round-bottom flask along with 30 mL dichloromethane. To this stirred solution was added diisopropylethyl amine (0.067 mL, 0.385 mmol) which resulted in the dissolution of the starting material. This stirred solution was cooled on an ice bath. Boron tribromide in dichloromethane (1.74 mL of a 1 M solution, 1.74 mmol) was added to the amine solution and a precipitate formed. This solution was stirred for about 2 hours while keeping on the ice bath at which time 4 mL methanol was added to quench the excess boron tribromide. The solvents were then removed in vacuo and the residue dissolved in 100 mL dichloromethane. The organic extract was washed twice with 100 mL 0.02 M sodium hydroxide. An emulsion formed which was broken up by the addition of solid sodium chloride. The organic extract was washed once with 100 mL brine and then dried over magnesium sulfate followed by the removal of the solvents in vacuo. The residue was dissolved in methanol and ethanolic hydrogen chloride was added. The solvents were removed in vacuo to give the crude product as a solid film. This material was further purified by heating briefly in isopropanol, allowing the solid to separate, followed by filtration, and then drying under vacuum to yield [1α,2α(trans)]-N-[[[[[1,2,3,4-tetrahydro-6-hydroxy-1-(3-pyridinylmethyl)-2-naphthalenyl]amino]methyl]-4-cyclohexyl]methyl]2-fluorobenzenesulfonamide bis-hydrochloride 44 as a tan powder (0.054 g, 0.088 mmol). MS (MH$^+$) 538; $^1$H NMR (DMSO-d$_6$): δ0.69–1.12 (m, 4H), 1.22–1.46 (m, 1H), 1.61–2.32 (m, 7H), 2.60–3.12 (m, 7H), 3.29–3.61 (m, 3H), 5.67 (d, 1H), 6.18 (dd, 1H), 6.52 (s, 1H), 7.30–7.51 (m, 2H), 7.63–7.84 (m, 2H), 7.85–8.02 (m, 2H), 8.27 (d, 1H), 8.62–8.84 (m, 2H), 9.03 (br, 1H), 9.45 (br, 1H) (FIG. 14).

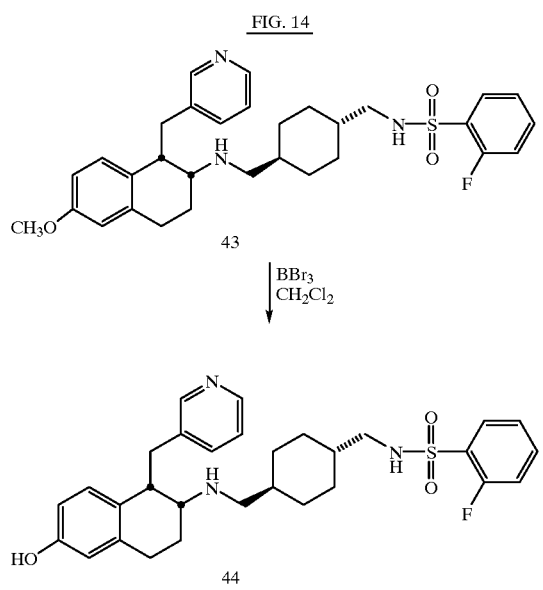

FIG. 14

Other compounds of this invention having the formula 1 can be prepared using the methods described herein. There are over one thousand compounds that contain a phenylacetic acid moiety that are commercially available, and many more that are known, and these compounds can be converted to the corresponding β-tetralones using the chemistry described in EXAMPLE 4. These intermediates can be converted to products of formula 1 that contain a wide variety of (R$_1$)$_n$ groups using the chemistry described in EXAMPLE 4. In some cases, the use of protecting groups may be needed and these manipulations are known to those skilled in the art. For example, aminophenylacetic acid can be converted to the corresponding phthalimide upon reaction with phthalic anhydride or N-carbethoxyphthalimide. Using the chemistry described in EXAMPLE 4A, phthalimido-β-tetralones can be prepared by substituting (phthalimido) phenyl acetic acids for 4-fluoroacetic acid, and these materials can be subsequently converted to products of formula 1 wherein, upon phthalimide cleavage, (R$_1$), is amino (NH$_2$). Alkylamino (–NHR) and dialkylamino (–NR'R") analogs can be prepared from the phthalimido-β-tetralone as well.

The use of alpha-substituted phenylacetic acid starting materials affords compounds of formula 1 wherein B$_2$ is alkyl or substituted alkyl and not hydrogen.

Compounds of this invention of formula 1 having a pyrimidyl, imidazolyl, thienyl or furyl substitutent as R$_2$ can be prepared using the chemistry described in EXAMPLE 3 in which a β-tetralone is reacted with a heteroaryl aldehyde. For example furan- and thienyl-carboxaldehydes can be substituted for 3-pyridylcarboxaldehyde in EXAMPLE 3A and reacted with p-tetralones and these intermediates can be subsequently converted to products of formula 1 wherein R$_2$ is 2-furyl or 3-furyl or 2-thienyl or 3-thienyl, and Y is methylene and m=1. Similarly, N-trityl imidazole-carboxaldehyde can be used to produce compounds of formula 1 in which R$_2$ is 2-imidazolyl or 4(5)-imidazolyl and Y is methylene and m=1. Compounds of formula 1 in which the R$_2$ substituent is cyclopropyl and Y=methylene and m=1 can be made using the chemistry described in EXAMPLE 1, substituting cyclopropylmethyl bromide for benzyl bromide. Compounds of formula 1 in which the R$_2$ substituent is phenoxy or thiophenyl can be prepared by substituting chloromethylphenyl ether or a chloromethylphenyl sulfide for benzyl bromide in EXAMPLE 1.

Compounds of formula 1 in which the R$_2$ substituent is piperidine can be made by reducing the corresponding pyridyl analog, such as that described in EXAMPLE 3, using catalytic hydrogenation conditions (i.e., platinum oxide on carbon).

Compounds of formula 1 in which the R$_3$ substituent is heteroaryl can be preparered by substituting a pyridinyl, thienyl or furyl sulfonylchloride for 2-naphthylsulfonamide in EXAMPLE 3F. N-alkylimidazolylsulfonyl chlorides can be used to prepare compounds of formula 1 in which the R$_3$ substituent is imidazolyl.

Additional compounds of this invention that were prepared using the experimental protocols described above include:

Mass Spectral Data of Compounds (1)

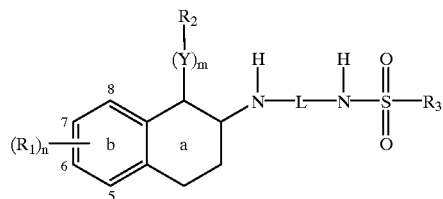

(1)

| # | R$_1$ | R$_2$ | Y=CH$_2$ m= | L | R$_3$ | Obs M$^+$ | Calc. Mass |
|---|---|---|---|---|---|---|---|
| 45 | (H) | Ph | 1 | (CH$_2$)$_4$ | 2-naphthyl | 499 | 498.7 |
| 46 | (H) | Ph | 1 | (CH$_2$)$_5$ | 2-naphthyl | 513 | 512.7 |
| 47 | 6-OMe | Ph | 1 | (CH$_2$)$_7$ | 2-naphthyl | 571 | 570.8 |
| 48 | 6-OMe | Ph | 1 | (CH$_2$)$_8$ | 2-naphthyl | 585 | 584.8 |
| 49 | 6-OMe | Ph | 1 | —H$_2$C—C$_6$H$_4$—CH$_2$— (para) | 2-naphthyl | 577 | 576.7 |
| 50 | 6-OMe | Ph | 1 | cyclohexyl | 2-naphthyl | 555 | 554.7 |
| 51 | 6-OMe | Ph | 1 | —H$_2$C—(trans-cyclohexyl)—CH$_2$— | 1-naphthyl | 583 | 582.8 |
| 52 | 6-OMe | Ph | 1 | —H$_2$C—(trans-cyclohexyl)—CH$_2$— | Ph | 533 | 532.7 |
| 53 | 6-OMe | Ph | 1 | —H$_2$C—(trans-cyclohexyl)—CH$_2$— | (3,4-diOMe)Ph | 593 | 592.8 |
| 54 | 6-OMe | Ph | 1 | —H$_2$C—(trans-cyclohexyl)—CH$_2$— | (2-NO$_2$)Ph | 578 | 577.7 |
| 55 | 6-OMe | Ph | 1 | —H$_2$C—(trans-cyclohexyl)—CH$_2$— | (4-SO$_2$Me)Ph | 611 | 610.8 |
| 56 | 6-OMe | Ph | 1 | —H$_2$C—(trans-cyclohexyl)—CH$_2$— | (3,5-diCl)Ph | 601 | 601.6 |
| 57 | 6-OMe | Ph | 1 | —H$_2$C—(trans-cyclohexyl)—CH$_2$— | (2-F)Ph | 551 | 550.7 |
| 58 | 6-OMe | Ph | 1 | —H$_2$C—(trans-cyclohexyl)—CH$_2$— | (4-F)Ph | 551 | 550.7 |

-continued

Mass Spectral Data of Compounds (1)

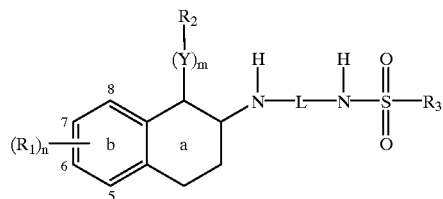

(1)

| # | $R_1$ | $R_2$ | Y=CH$_2$ m= | L | $R_3$ | Obs M$^+$ | Calc. Mass |
|---|---|---|---|---|---|---|---|
| 59 | 6-OMe | Ph | 1 | —H$_2$C-cyclohexyl-CH$_2$— | 2-thienyl | 539 | 538.8 |
| 60 | 6-OMe | Ph | 1 | —H$_2$C-cyclohexyl-CH$_2$— | (3-F)Ph | 551 | 550.7 |
| 61 | 6-OMe | Ph | 1 | —H$_2$C-cyclohexyl-CH$_2$— | (2,4-diCl)Ph | 601 | 601.6 |
| 62 | 6-OMe | Ph | 1 | —H$_2$C-cyclohexyl-CH$_2$— | (3-NO$_2$)Ph | 578 | 577.7 |
| 63 | 6-OMe | Ph | 1 | —H$_2$C-cyclohexyl-CH$_2$— | (4-NO$_2$)Ph | 578 | 577.7 |
| 64 | 6-Cl | Ph | 1 | —H$_2$C-cyclohexyl-CH$_2$— | (2-NO$_2$)Ph | 582 | 582.1 |
| 65 | 6-OMe | Ph | 1 | —H$_2$C-cyclohexyl-CH$_2$— | (2-CF$_3$)Ph | 601 | 600.7 |
| 66 | 6-OMe | Ph | 1 | —H$_2$C-cyclohexyl-CH$_2$— | (2-Cl)Ph | 567 | 567.1 |
| 67 | 6-OMe | Ph | 1 | —H$_2$C-cyclohexyl-CH$_2$— | (2-CH$_2$NH$_2$)Ph | 562 | 561.8 |
| 68 | 6-OMe | Ph | 1 | —H$_2$C-cyclohexyl-CH$_2$— | (2-Br)Ph | 611 | 611.6 |
| 69 | 6-OMe | Ph | 1 | —H$_2$C-cyclohexyl-CH$_2$— | (3-Br)Ph | 611 | 611.6 |

-continued

Mass Spectral Data of Compounds (1)

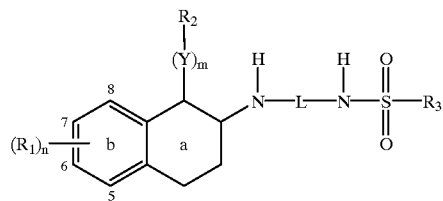

(1)

| # | R₁ | R₂ | Y=CH₂ m= | L | R₃ | Obs M⁺ | Calc. Mass |
|---|------|----|---------|---|------|--------|-----------|
| 70 | 6-OMe | Ph | 1 | —H₂C-cyclohexyl-CH₂— | (4-Br)Ph | 611 | 611.6 |
| 71 | 6-OH | Ph | 1 | —H₂C-cyclohexyl-CH₂— | Ph | 519 | 518.7 |
| 72 | 6-F | Ph | 1 | —H₂C-cyclohexyl-CH₂— | (2-NO₂)Ph | 566 | 565.7 |
| 73 | 6-F | Ph | 1 | —H₂C-cyclohexyl-CH₂— | (2-Cl)Ph | 555 | 555.1 |
| 74 | 6-F | Ph | 1 | —H₂C-cyclohexyl-CH₂— | (2-Br)Ph | 599 | 599.6 |
| 75 | 6-F | Ph | 1 | —H₂C-cyclohexyl-CH₂— | (2,3-diCl)Ph | 589 | 589.6 |
| 76 | 6-F | Ph | 1 | —H₂C-cyclohexyl-CH₂— | (2,4-diCl)Ph | 589 | 589.6 |
| 77 | 6-F | Ph | 1 | —H₂C-cyclohexyl-CH₂— | (2,6-diCl)Ph | 589 | 589.6 |
| 78 | 6-F | Ph | 1 | —H₂C-cyclohexyl-CH₂— | (3,4-diCl)Ph | 589 | 589.6 |
| 79 | 7-OMe | Ph | 1 | —H₂C-cyclohexyl-CH₂— | Ph | 533 | 532.7 |
| 80 | 7-OMe | Ph | 1 | —H₂C-cyclohexyl-CH₂— | 2-naphthyl | 583 | 582.8 |

-continued

Mass Spectral Data of Compounds (1)

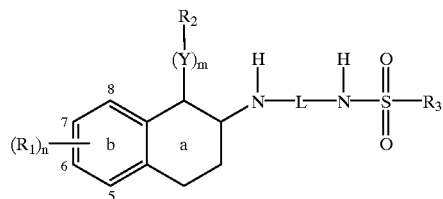

(1)

| # | $R_1$ | $R_2$ | Y=CH$_2$ m= | L | $R_3$ | Obs M$^+$ | Calc. Mass |
|---|---|---|---|---|---|---|---|
| 81 | 6-OMe | 2-naphthyl | 1 | —H$_2$C—(cyclohexyl)—CH$_2$— | Ph | 583 | 582.8 |
| 82 | 6-OMe | 2-naphthyl | 1 | —H$_2$C—(cyclohexyl)—CH$_2$— | 2-naphthyl | 633 | 632.9 |
| 83 | 6-OMe | (3-OMe)Ph | 1 | —H$_2$C—(cyclohexyl)—CH$_2$— | Ph | 563 | 562.8 |
| 84 | 6-OMe | (3-CMe)Ph | 1 | —H$_2$C—(cyclohexyl)—CH$_2$— | 2-naphthyl | 613 | 612.8 |
| 85 | 6-OMe | (2-OMe)Ph | 1 | —H$_2$C—(cyclohexyl)—CH$_2$— | Ph | 563 | 562.8 |
| 86 | 6-OMe | (4-OMe)Ph | 1 | —H$_2$C—(cyclohexyl)—CH$_2$— | Ph | 563 | 562.8 |
| 87 | 6-OMe | (4-NO$_2$)Ph | 1 | —H$_2$C—(cyclohexyl)—CH$_2$— | Ph | 578 | 577.7 |
| 88 | 6-OMe | (4-NO$_2$)Ph | 1 | —H$_2$C—(cyclohexyl)—CH$_2$— | (2-NO$_2$)Ph | 623 | 622.7 |
| 89 | 6-OMe | (2,6-diF)Ph | 1 | —H$_2$C—(cyclohexyl)—CH$_2$— | Ph | 570 | 568.7 |
| 90 | 6-OMe | (2,6-diF)Ph | 1 | —H$_2$C—(cyclohexyl)—CH$_2$— | (2-NO$_2$)Ph | 614 | 613.7 |
| 91 | 6-OMe | (2-OMe)Ph | 1 | —H$_2$C—(cyclohexyl)—CH$_2$— | (2-NO$_2$)Ph | 608 | 607.7 |

-continued

Mass Spectral Data of Compounds (1)

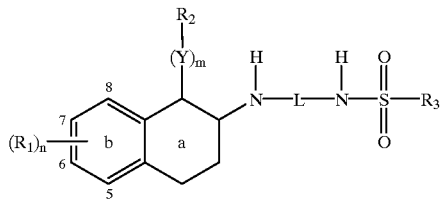

(1)

| # | R₁ | R₂ | Y=CH₂ m= | L | R₃ | Obs M⁺ | Calc. Mass |
|---|------|-----------|---|---------------|-----------|-----|-------|
| 92 | 6-F | 3-pyridyl | 1 | —H₂C-cyclohexyl-CH₂— | (2-Cl)Ph | 556 | 556.1 |
| 93 | 6-OMe | (3-Cl)Ph | 1 | —H₂C-cyclohexyl-CH₂— | 2-naphthyl | 617 | 617.2 |
| 94 | 6-OMe | (3-CF₃)Ph | 1 | —H₂C-cyclohexyl-CH₂— | 2-naphthyl | 651 | 650.8 |
| 95 | 6-OMe | (2-Cl)Ph | 1 | —H₂C-cyclohexyl-CH₂— | Ph | 567 | 567.2 |
| 96 | 6-OMe | (3-Cl)Ph | 1 | —H₂C-cyclohexyl-CH₂— | Ph | 567 | 567.2 |
| 97 | 6-OMe | (4-Cl)Ph | 1 | —H₂C-cyclohexyl-CH₂— | Ph | 567 | 567.2 |
| 98 | 6-OMe | (2-CF₃)Ph | 1 | —H₂C-cyclohexyl-CH₂— | Ph | 601 | 600.7 |
| 99 | 6-OMe | (3-CF₃)Ph | 1 | —H₂C-cyclohexyl-CH₂— | Ph | 601 | 600.7 |
| 100 | 6-OMe | (4-CF₃)Ph | 1 | —H₂C-cyclohexyl-CH₂— | Ph | 601 | 600.7 |
| 101 | 6-Br | Ph | 1 | —H₂C-cyclohexyl-CH₂— | Ph | 581 | 581.6 |
| 102 | 6-Cl | Ph | 1 | —H₂C-cyclohexyl-CH₂— | Ph | 537 | 537.1 |

-continued

Mass Spectral Data of Compounds (1)

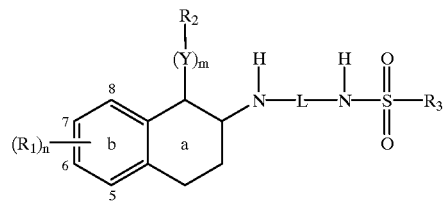

(1)

| # | R$_1$ | R$_2$ | Y=CH$_2$m= | L | R$_3$ | Obs M$^+$ | Calc. Mass |
|---|---|---|---|---|---|---|---|
| 103 | 6-F | Ph | 1 | —H$_2$C-cyclohexyl-CH$_2$— | Ph | 521 | 520.7 |
| 104 | 7-Cl | Ph | 1 | —H$_2$C-cyclohexyl-CH$_2$— | Ph | 537 | 537.1 |
| 105 | 5-Cl | Ph | 1 | —H$_2$C-cyclohexyl-CH$_2$— | Ph | 537 | 537.1 |
| 106 | 8-Cl | Ph | 1 | —H$_2$C-cyclohexyl-CH$_2$— | Ph | 537 | 537.1 |
| 107 | 6,7-F$_2$ | Ph | 1 | —H$_2$C-cyclohexyl-CH$_2$— | Ph | 539 | 538.7 |
| 108 | 6,7-diOMe | Ph | 1 | —H$_2$C-cyclohexyl-CH$_2$— | Ph | 563 | 562.8 |
| 109 | 6,7-diOH | Ph | 1 | —H$_2$C-cyclohexyl-CH$_2$— | Ph | 535 | 534.7 |
| 110 | 6-OH | CH=CH$_2$ | 1 | —H$_2$C-cyclohexyl-CH$_2$— | Ph | 469 | 468.6 |
| 111 | 6-F | 3-pyridyl | 1 | —H$_2$C-cyclohexyl-CH$_2$— | (2-F)Ph | 540 | 539.7 |
| 112 | (H) | 3-pyridyl | 1 | —H$_2$N-cyclohexyl-~~~ | Ph | 490 | 489. |

In Vitro Assays

NPY5 HTS Centrifugation Assay

The compounds described in this invention were evaluated for binding to the human neuropeptide Y5 receptor.

Stable Transfection

The human NPY5 receptor cDNA (Genbank Accession number U66275) was inserted into the vector pClneo (Invitrogen) and transfected into human embryonic kidney cells (HEK-293) via Calcium phosphate method (Cullen 1987). Stably transfected cells were selected with G-418

(600 ug/mL). Stably transfected cells served as the source for the membranes for the NPY5 receptor binding assay.

Membrane Preparation

NPY5-transfected HEK293 cells were grown to confluence in 150 cm² culture dishes. Cells were washed once with phosphate-buffered saline (Gibco Cat#14040–133). Cells were then incubated in phosphate-buffered saline without Calcium and without Magnesium, supplemented with 2 mM EDTA. Cells were incubated for 10 minutes at room temperature and the cells were collected by repetitive pipeting. Cells were formed into pellets and then frozen at −80 until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4C at 200 g. Supernatants were transferred to corex tubes and centrifuged for 25 minutes at 28,000 g. Pellets were re-suspended in Binding (20 mM HEPES, 10 mM NaCl, 0.22 mM $KH_2PO_4$, 1.3 mM $CaCl_2$, 0.8 mM $MgSO_4$, pH 7.4). Membranes were kept on ice until use.

A competition binding assay, known to those skilled in the art, was used in which aminotetralins (I) compete with $^{125}$I-PYY for binding to cell membranes. In simple terms, the less $^{125}$I-PYY bound to the membranes implies that a compound is a good inhibitor (competitor). Bound $^{125}$I-PYY is determined by centrifugation of membranes, aspirating supernatant, washing away residual $^{125}$I-PYY and subsequently counting the bound sample in a g-counter.

Procedure for Radioligand binding assay

Compounds to be tested were prepared as 10× stocks in binding buffer and added first to assay tubes (RIA vials, Sarstedt). Twenty (20) μL of each 10× compound stock is pipeted into vials and 80 μL of $^{125}$I-PYY (NEN catalog number NEX240), which has been diluted to a concentration of 200 pM in 0.25% BSA in binding buffer, is added to the compound tubes (final concentration of $^{125}$I-PYY is 80 pM). To each tube is added 100 μL of membranes and the mixture is agitated by pipeting 2 times. Samples are incubated for 1 hr at room temperature. Aluminum cast plates (Sarstedt) containing the vials are then centrifuged 10 minutes at 3200 rpm in a Sorvall RT6000. Supernatant is then aspirated. To each vial 400 μL PBS is added and this is then aspirated again. Vials are then put in carrier polypropylene 12×75 tube and counted in gamma counter (Packard). Non-specific binding is determined in the presence of 300 nM NPY. Percent inhibition of $^{125}$I-PYY binding is calculated by subtracting non-specific binding from the test samples (compound (I)), taking these counts and dividing by total binding, and multiplying by 100. Inhibitory concentration values ($IC_{50}$) of compounds that show appreciable inhibition of $^{125}$I-PYY binding are calculated by obtaining percent inhibition of $^{125}$I-PYY binding values at different concentrations of the test compound, and using a graphing program such as GraphPad Prism (San Diego, Calif.) to calculate the concentration of test compound that inhibits fifty-percent of $^{125}$I-PYY binding (Table 4). These operations are known to those skilled in the art.

TABLE 4

Binding Affinities of Compounds (1) for the Human NPY Y5 Receptor (expressed as % Inhibition of $^{125}$I-PYY Binding)

(1)

| # | $R_1$ | $R_2$ | Y=$CH_2$ m= | L | $R_3$ | % Inh @ 3 uM |
|---|---|---|---|---|---|---|
| 10 | 6-OMe | Ph | 1 | —$H_2C$–(cyclohexyl trans)–$CH_2$— | 2-naphthyl | 96 |
| 11 | 6-OMe | Ph | 1 | $(CH_2)_5$ | 2-naphthyl | 95 |
| 18 | 6-OMe | 3-pyridyl | 1 | —$H_2C$–(cyclohexyl trans)–$CH_2$— | 2-naphthyl | 96 |
| 26 | 6-F | Ph | 1 | —$H_2C$–(cyclohexyl trans)–$CH_2$— | (2-F)Ph | 107 |
| 34 | 6-OMe | Ph | 0 | —$H_2C$–(cyclohexyl trans)–$CH_2$— | 2-naphthyl | 46 |

TABLE 4-continued

Binding Affinities of Compounds (1) for the Human NPY Y5 Receptor
(expressed as % Inhibition of $^{125}$I-PYY Binding)

(1)

| # | R$_1$ | R$_2$ | Y=CH$_2$ m= | L | R$_3$ | % Inh @ 3 uM |
|---|---|---|---|---|---|---|
| 39 | 6-OMe | CH=CH$_2$ | 1 | —H$_2$C-cyclohexyl-CH$_2$— | Ph | 102 |
| 40 | 6-OMe | OH | 3 | —H$_2$C-cyclohexyl-CH$_2$— | Ph | 91 |
| 42 | 6-OMe | Me | 2 | —H$_2$C-cyclohexyl-CH$_2$— | Ph | 101 |
| 43 | 6-OMe | 3-pyridyl | 1 | —H$_2$C-cyclohexyl-CH$_2$— | (2-F)Ph | 100 |
| 44 | 6-OH | 3-pyridyl | 1 | —H$_2$C-cyclohexyl-CH$_2$— | (2-F)Ph | 101 |
| 45 | (H) | Ph | 1 | (CH$_2$)$_4$ | 2-naphthyl | 58 |
| 46 | (H) | Ph | 1 | (CH$_2$)$_5$ | 2-naphthyl | 89 |
| 47 | 6-OMe | Ph | 1 | (CH$_2$)$_7$ | 2-naphthyl | 79 |
| 48 | 6-OMe | Ph | 1 | (CH$_2$)$_8$ | 2-naphthyl | 68 |
| 49 | 6-OMe | Ph | 1 | —H$_2$C-cyclohexyl-CH$_2$— | 2-naphthyl | 60 |
| 50 | 6-OMe | Ph | 1 | cyclohexyl | 2-naphthyl | 44 |
| 51 | 6-OMe | Ph | 1 | —H$_2$C-cyclohexyl-CH$_2$— | 1-naphthyl | 95 |
| 52 | 6-OMe | Ph | 1 | —H$_2$C-cyclohexyl-CH$_2$— | Ph | 99 |
| 53 | 6-OMe | Ph | 1 | —H$_2$C-cyclohexyl-CH$_2$— | (3,4-diOMe)Ph | 100 |

TABLE 4-continued

Binding Affinities of Compounds (1) for the Human NPY Y5 Receptor
(expressed as % Inhibition of $^{125}$I-PYY Binding)

(1)

| # | R$_1$ | R$_2$ | Y=CH$_2$ m= | L | R$_3$ | % Inh @ 3 uM |
|---|-------|-------|-------------|---|-------|--------------|
| 54 | 6-OMe | Ph | 1 | —H$_2$C-cyclohexyl-CH$_2$— | (2-NO$_2$)Ph | 94 |
| 55 | 6-OMe | Ph | 1 | —H$_2$C-cyclohexyl-CH$_2$— | (4-SO$_2$Me)Ph | 90 |
| 56 | 6-OMe | Ph | 1 | —H$_2$C-cyclohexyl-CH$_2$— | (3,5-diCl)Ph | 73 |
| 57 | 6-OMe | Ph | 1 | —H$_2$C-cyclohexyl-CH$_2$— | (2-F)Ph | 98 |
| 58 | 6-OMe | Ph | 1 | —H$_2$C-cyclohexyl-CH$_2$— | (4-F)Ph | 91 |
| 59 | 6-OMe | Ph | 1 | —H$_2$C-cyclohexyl-CH$_2$— | 2-thienyl | 102 |
| 60 | 6-OMe | Ph | 1 | —H$_2$C-cyclohexyl-CH$_2$— | (3-F)Ph | 94 |
| 61 | 6-OMe | Ph | 1 | —H$_2$C-cyclohexyl-CH$_2$— | (2,4-diCl)Ph | 94 |
| 62 | 6-OMe | Ph | 1 | —H$_2$C-cyclohexyl-CH$_2$— | (3-NO$_2$)Ph | 95 |
| 63 | 6-OMe | Ph | 1 | —H$_2$C-cyclohexyl-CH$_2$— | (4-NO$_2$)Ph | 93 |
| 64 | 6-Cl | Ph | 1 | —H$_2$C-cyclohexyl-CH$_2$— | (2-NO$_2$)Ph | 93 |

TABLE 4-continued

Binding Affinities of Compounds (1) for the Human NPY Y5 Receptor
(expressed as % Inhibition of $^{125}$I-PYY Binding)

(1)

| # | $R_1$ | $R_2$ | Y=CH$_2$ m= | L | $R_3$ | % Inh @ 3 uM |
|---|---|---|---|---|---|---|
| 65 | 6-OMe | Ph | 1 | —H$_2$C—cyclohexyl—CH$_2$— | (2-CF$_3$)Ph | 0 |
| 66 | 6-OMe | Ph | 1 | —H$_2$C—cyclohexyl—CH$_2$— | (2-Cl)Ph | 99 |
| 67 | 6-OMe | Ph | 1 | —H$_2$C—cyclohexyl—CH$_2$— | (2-CH$_2$NH$_2$)Ph | 91 |
| 68 | 6-OMe | Ph | 1 | —H$_2$C—cyclohexyl—CH$_2$— | (2-Br)Ph | 100 |
| 69 | 6-OMe | Ph | 1 | —H$_2$C—cyclohexyl—CH$_2$— | (3-Br)Ph | 93 |
| 70 | 6-OMe | Ph | 1 | —H$_2$C—cyclohexyl—CH$_2$— | (4-Br)Ph | 95 |
| 71 | 6-OH | Ph | 1 | —H$_2$C—cyclohexyl—CH$_2$— | Ph | 102 |
| 72 | 6-F | Ph | 1 | —H$_2$C—cyclohexyl—CH$_2$— | (2-NO$_2$)Ph | 106 |
| 73 | 6-F | Ph | 1 | —H$_2$C—cyclohexyl—CH$_2$— | (2-Cl)Ph | 107 |
| 74 | 6-F | Ph | 1 | —H$_2$C—cyclohexyl—CH$_2$— | (2-Br)Ph | 105 |
| 75 | 6-F | Ph | 1 | —H$_2$C—cyclohexyl—CH$_2$— | (2,3-diCl)Ph | 100 |

TABLE 4-continued

Binding Affinities of Compounds (1) for the Human NPY Y5 Receptor
(expressed as % Inhibition of $^{125}$I-PYY Binding)

(1)

| # | $R_1$ | $R_2$ | Y=CH$_2$ m= | L | $R_3$ | % Inh @ 3 uM |
|---|---|---|---|---|---|---|
| 76 | 6-F | Ph | 1 | —H$_2$C-cyclohexyl-CH$_2$— (trans) | (2,4-diCl)Ph | 99 |
| 77 | 6-F | Ph | 1 | —H$_2$C-cyclohexyl-CH$_2$— (trans) | (2,6-diCl)Ph | 102 |
| 78 | 6-F | Ph | 1 | —H$_2$C-cyclohexyl-CH$_2$— (trans) | (3,4-diCl)Ph | 92 |
| 79 | 7-OMe | Ph | 1 | —H$_2$C-cyclohexyl-CH$_2$— (trans) | Ph | 93 |
| 80 | 7-OMe | Ph | 1 | —H$_2$C-cyclohexyl-CH$_2$— (trans) | 2-naphthyl | 75 |
| 81 | 6-OMe | 2-naphthyl | 1 | —H$_2$C-cyclohexyl-CH$_2$— (trans) | Ph | 89 |
| 82 | 6-OMe | 2-naphthyl | 1 | —H$_2$C-cyclohexyl-CH$_2$— (trans) | 2-naphthyl | 54 |
| 83 | 6-OMe | (3-OMe)Ph | 1 | —H$_2$C-cyclohexyl-CH$_2$— (trans) | Ph | 92 |
| 84 | 6-OMe | (3-OMe)Ph | 1 | —H$_2$C-cyclohexyl-CH$_2$— (trans) | 2-naphthyl | 82 |
| 85 | 6-OMe | (2-OMe)Ph | 1 | —H$_2$C-cyclohexyl-CH$_2$— (trans) | Ph | 74 |
| 86 | 6-OMe | (4-OMe)Ph | 1 | —H$_2$C-cyclohexyl-CH$_2$— (trans) | Ph | 25 |

TABLE 4-continued
Binding Affinities of Compounds (1) for the Human NPY Y5 Receptor
(expressed as % Inhibition of $^{125}$I-PYY Binding)
(1)
| # | R$_1$ | R$_2$ | Y=CH$_2$ m= | L | R$_3$ | % Inh @ 3 uM |
|---|---|---|---|---|---|---|
| 87 | 6-OMe | (4-NO$_2$)Ph | 1 |  | Ph | 84 |
| 88 | 6-OMe | (4-NO$_2$)Ph | 1 |  | (2-NO$_2$)Ph | 85 |
| 89 | 6-OMe | (2,6-diF)Ph | 1 |  | Ph | 98 |
| 90 | 6-OMe | (2,6-diF)Ph | 1 |  | (2-NO$_2$)Ph | 97 |
| 91 | 6-OMe | (2-OMe)Ph | 1 |  | (2-NO$_2$)Ph | 92 |
| 92 | 6-F | 3-pyridyl | 1 |  | (2-Cl)Ph | 100 |
| 93 | 6-OMe | (3-Cl)Ph | 1 |  | 2-naphthyl | 60 |
| 94 | 6-OMe | (3CF$_3$)Ph | 1 |  | 2-naphthyt | 45 |
| 95 | 6-OMe | (2-Cl)Ph | 1 |  | Ph | 84 |
| 96 | 6-OMe | (3-Cl)Ph | 1 |  | Ph | 100 |
| 97 | 6-OMe | (4-Cl)Ph | 1 |  | Ph | 90 |

TABLE 4-continued

Binding Affinities of Compounds (1) for the Human NPY Y5 Receptor
(expressed as % Inhibition of $^{125}$I-PYY Binding)

(1)

| # | R$_1$ | R$_2$ | Y=CH$_2$ m= | L | R$_3$ | % Inh @ 3 uM |
|---|---|---|---|---|---|---|
| 98 | 6-OMe | (2-CF$_3$)Ph | 1 | —H$_2$C—⟨cyclohexyl⟩—CH$_2$— | Ph | 30 |
| 99 | 6-OMe | (3-CF$_3$)Ph | 1 | —H$_2$C—⟨cyclohexyl⟩—CH$_2$— | Ph | 99 |
| 100 | 6-OMe | (4-CF$_3$)Ph | 1 | —H$_2$C—⟨cyclohexyl⟩—CH$_2$— | Ph | 93 |
| 101 | 6-Br | Ph | 1 | —H$_2$C—⟨cyclohexyl⟩—CH$_2$— | Ph | 100 |
| 102 | 6-Cl | Ph | 1 | —H$_2$C—⟨cyclohexyl⟩—CH$_2$— | Ph | 100 |
| 103 | 6-F | Ph | i | —H$_2$C—⟨cyclohexyl⟩—CH$_2$— | Ph | 98 |
| 104 | 7-Cl | Ph | 1 | —H$_2$C—⟨cyclohexyl⟩—CH$_2$— | Ph | 97 |
| 105 | 5-Cl | Ph | 1 | —H$_2$C—⟨cyclohexyl⟩—CH$_2$— | Ph | 98 |
| 106 | 8-Cl | Ph | 1 | —H$_2$C—⟨cyclohexyl⟩—CH$_2$— | Ph | 104 |
| 107 | 6,7-diF | Ph | i | —H$_2$C—⟨cyclohexyl⟩—CH$_2$— | Ph | 103 |
| 108 | 6,7-diOMe | Ph | 1 | —H$_2$C—⟨cyclohexyl⟩—CH$_2$— | Ph | 99 |

TABLE 4-continued

Binding Affinities of Compounds (1) for the Human NPY Y5 Receptor
(expressed as % Inhibition of $^{125}$I-PYY Binding)

(1)

[Structure of compound (1) showing a tetrahydronaphthalene with $R_1$ substituents at positions 5-8, $R_2(Y)_m$ group, NH-L-NH-SO$_2$-R$_3$ linker]

| # | R$_1$ | R$_2$ | Y=CH$_2$ m= | L | R$_3$ | % Inh @ 3 uM |
|---|---|---|---|---|---|---|
| 109 | 6,7-diOH | Ph | 1 | —H$_2$C—[cyclohexyl]—CH$_2$— | Ph | 101 |
| 110 | 6-OMe | CH=CH$_2$ | 1 | —H$_2$C—[cyclohexyl]—CH$_2$— | Ph | 100 |
| 111 | 6-F | 3-pyridyl | 1 | —H$_2$C—[cyclohexyl]—CH$_2$— | (2-F)Ph | 100 |
| 112 | (H) | 3-pyridyl | 1 | —H$_2$N—[cyclohexyl]— | Ph | 95 |

In Vivo Assays

Rodent Feeding Model: Measurement of Food Intake in Food-Deprived Rats

Male Long-Evans rats (180–200 grams) are housed individually and are maintained on a once-a-day feeding schedule (i.e. 10 a.m. until 4 p.m.) for five days following quarantine to allow the animals to acclimate to feeding on powdered chow (#5002 PMI Certified Rodent Meal) during the allotted time. The chow is made available in an open jar, anchored in the cage by a wire, with a metal follower covering the food to minimize spillage. Water is available ad-libitum.

Animals are fasted for 18 hours prior to testing. At the end of the fasting period, animals are administered either compounds of the invention or vehicle. Vehicle and test compounds are administered either orally (5 mL/kg) 60 minutes prior to the experiment, or 30 minutes prior when given subcutaneously (1 mL/kg) or intraperitoneally (1 mL/kg). Compounds of the invention are administered orally as a suspension in aqueous 0.5% methylcellulose-0.4% Tween 80, or intraperitoneally as a solution or suspension in PEG 200; compound concentrations typically range from 1 mg/kg to 100 mg/kg, preferably from 10–30 mg/kg. Food intake is measured at 2, 4, and 6 hours after administration by weighing the special jar containing the food before the experiment and at the specified times. Upon completion of the experiment, all animals are given a one-week washout period before retesting.

Percent reduction of food consumption is calculated subtracting the grams of food consumed by the treated group from the grams of food consumed by the control group divided by the grams of food consumed by the control group, multiplied by 100.

$$\% \text{ change} = \frac{\text{Treatment} - \text{Vehicle}}{\text{Vehicle}} \times 100$$

A negative value indicates a reduction in food consumption and a positive value indicates an increase in food consumption.

| | | Food Consumption (grams) | | |
|---|---|---|---|---|
| Compound | Dose (mg/kg) (# rats) | 0–2 hrs (% chg.) | 0–6 hrs (% chg.) | 2–6 hrs (% chg.) |
| Vehicle PEG-2000 | N = 8 | 8.63 g | 19.88 g | 11.25 g |
| 53 | 30 (i.p.) | 5.75 g | 11.88 g | 6.13 g |
| | N = 8 | (−33.3%) | (−40.2%) | (−45.6%) |
| Vehicle PEG-2000 | N = 8 | 8.00 g | 18.5 g | 10.5 g |
| 43 | 30 (i.p.) | 6.63 g | 15.25 g | 8.63 g |
| | N = 8 | (−17.1%) | (−17.6%) | (−17.8%) |
| 44 | 30 (i.p.) | 4.75 g | 14.00 g | 9.25 g |
| | N = 8 | (−40.6%) | (−24.3%) | (−11.9%) |
| 111 | 30 (i.p.) | 5.13 g | 12.63 g | 7.50 g |
| | N = 8 | (−35.9%) | (−31.7%) | (−28.6%) |

What is claimed is:
1. A compound of formula 1

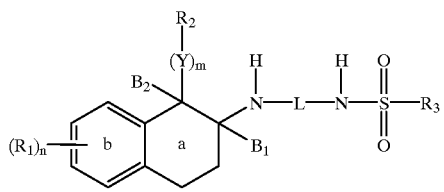
(1)

wherein
$R_1$ is independently selected from the group consisting of hydrogen; hydroxy; halo; $C_{1-8}$alkoxy; substituted $C_{1-8}$ alkoxy wherein the substituent is halo; trifluoroalkyl; $C_{1-8}$alkylthio and substituted $C_{1-8}$alkylthio wherein the substituent is selected from halo, trifluoroalkyl and $C_{1-8}$alkoxy; $C_{3-6}$cycloalkyl; $C_{3-8}$cycloalkoxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$B_2$ is selected from the group consisting of hydrogen; $C_{1-5}$alkyl; substituted $C_{1-5}$alkyl wherein the substituent is halogen;

Y is methylene m 0–3

$R_2$ is selected from the group consisting of hydrogen; hydroxy; $C_{1-6}$-alkyl; $C_{1-6}$alkenyl; $C_{3-7}$cycloalkyl; halo; phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; naphthyl; phenoxy; substituted phenoxy wherein the substituent is selected from halo, $C_{1-6}$alkyl, $C_{1-6}$alkoxy, trifluoro$C_{1-6}$alkyl, cyano and nitro; phenylthio and substituted phenylthio wherein the substituent is selected from halo, $C_{1-6}$alkyl, nitro and amino; a heteroaryl group such as pyridyl, pyrimidyl, furyl, thienyl, and imidazolyl; substituted heteroaryl wherein the substitutent is selected from $C_{1-6}$alkyl and halo; and heterocycloalkyl;

$B_1$ is selected from the group consisting of hydrogen; $C_{1-5}$alkyl; substituted $C_{1-5}$alkyl wherein the substituent is halo;

L is selected from the group consisting of $C_{1-8}$alkylene; $C_{2-10}$alkenylene; $C_{2-10}$alkynylene; $C_{1-4}$alkylenecycloalkyl$C_{1-4}$alkylene; $C_{2-4}$alkenylenecycloalkyl$C_{2-4}$alkenylene; $C_{2-4}$alkynylenecycloalkyl$C_{2-4}$alkynylene; $C_{1-4}$alkylenearyl$C_{1-6}$alkylene; and $C_{2-4}$alkenylenearyl$C_{2-4}$alkenylene;

$R_3$ is selected from $C_{1-8}$alkyl; substituted $C_{1-8}$alkyl wherein the substituent is selected from alkoxy and halo; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

and enantiomers, diastereomers, and pharmaceutically acceptable salts thereof with the proviso that when m is 0, R2 cannot be hydrogen or alkyl.

2. A compound of claim 1 selected from the group consisting of:

rac-[1α,2α(trans)]-N-[[[[[1,2,3,4-tetrahydro-6-methoxy-1-(phenylmethyl)-2-naphthalenyl]amino]methyl]4-cyclohexyl]methyl]2-naphthalenesulfonamide;

rac-[1α,2α(trans)]-N-[[[[[1,2,3,4-tetrahydro-6-methoxy-1-(phenylmethyl)-2-naphthalenyl]amino]-5-pentyl]2-naphthalenesulfonamide;

rac-[1α,2α(trans)]-N-[[[[[1,2,3,4-tetrahydro-6-methoxy-1-(3-pyridinylmethyl)-2-naphthalenyl]amino]methyl]-4-cyclohexyl]methyl]2-naphthalenesulfonamide;

rac-[1α,2α(trans)]-N-[[[[[1,2,3,4-tetrahydro-6-fluoro-1-(phenylmethyl)-2-naphthalenyl]amino]methyl]-4-cyclohexyl]methyl]2-fluorobenzenesulfonamide;

rac-[1α,2α(trans)]-N-[[[[[1,2,3,4-tetrahydro-6-fluoro-1-phenyl-2-naphthalenyl]amino]methyl]-4-cyclohexyl] methyl]2-naphthalenesulfonamide;

rac-[1α,2α(trans)]-N-[[[[[1,2,3,4-tetrahydro-6-methoxy-1-(1-propene-3-yl)-2-naphthalenyl]amino]methyl]4-cyclohexyl]methyl] benzenesulfonamide;

rac-[1α,2α(trans)]-N-[[[[[1,2,3,4-tetrahydro-6-methoxy-1-(3-hydroxypropyl)-2-naphthalenyl]amino]methyl]-4-cyclohexyl]methyl] benzenesulfonamide; and rac-[1α,2α(trans)]-N-[[[[[1,2,3,4-tetrahydro-6-methoxy-1-(n-propyl)-2-naphthalenyl]amino]methyl]-4-cyclohexyl]methyl] benzenesulfonamide.

3. A compound of claim 1 wherein the salt is a hydrochloride salt.

4. A compound of claim 1 of the formula:

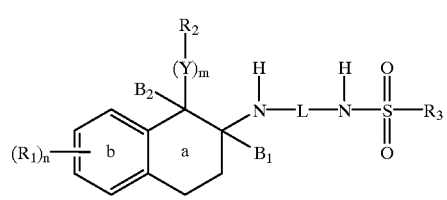
(1)

wherein
$R_1$ is independently selected from the group consisting of hydrogen; hydroxy; halo; $C_{1-8}$alkoxy; substituted $C_{1-8}$ alkoxy wherein the substituent is halo; trifluoroalkyl; $C_{1-8}$alkylthio and substituted $C_{1-8}$alkylthio wherein the substituent is selected from halo, such as chloro, bromo, fluoro and iodo, trifluoroalkyl and $C_{1-8}$alkoxy; $C_{3-6}$cycloalkyl; $C_{3-8}$cycloalkoxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$B_2$ hydrogen;

Y is methylene m 0–3

$R_2$ is selected from the group consisting of hydrogen; hydroxy; $C_{1-6}$alkyl; $C_{1-6}$alkenyl; halo; $C_{3-7}$cycloalkyl;

phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino and $C_{1-6}$dialkylamino; naphthyl; phenoxy; substituted phenoxy wherein the substituent is selected from halo, $C_{1-6}$alkyl, $C_{1-6}$alkoxy, trifluoro$C_{1-6}$alkyl, cyano and nitro; phenylthio and substituted phenylthio wherein the substituent is selected from halo, $C_{1-6}$alkyl, nitro and amino; a heteroaryl group such as pyridyl, pyrimidyl, furyl, thienyl, and imidazolyl; substituted heteroaryl wherein the substitutent is selected from $C_{1-6}$alkyl and halo; heterocycloalkyl;

$B_1$ is hydrogen;

L is selected from the group consisting of $C_{1-6}$alkylene; $C_{2-10}$alkenylene; $C_{2-10}$alkynylene; $C_{1-4}$alkylenecycloalkyl$C_{1-4}$alkylene; $C_{2-4}$alkenylenecycloalkyl$C_{2-4}$alkenylene; $C_{2-4}$alkynylenecycloalkyl$C_{2-4}$alkynylene; $C_{1-4}$alkylenearyl$C_{1-4}$alkylene; and $C_{2-4}$alkenylenearyl$C_{2-4}$alkenylene;

$R_3$ is selected from $C_{1-8}$alkyl; substituted $C_{1-8}$alkyl wherein the substituent is selected from alkoxy and halo; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

and enantiomers, diastereomers, and pharmaceutically acceptable salts thereof with the proviso that when m is 0, R2 cannot be hydrogen or alkyl.

5. A compound of claim 1 wherein:

$R_1$ is hydrogen, alkoxy, nitro, halo, amino, hydroxy or alkylamino;

$B_1$ and $B_2$ are hydrogen;

m is 0–3;

n is 1–2;

$R_2$ is phenyl, substituted phenyl, naphthyl, heteroaryl, substituted heteroaryl or cycloalkyl;

L=alkyl or alkylcycloalkyl;

$R_3$ is phenyl, substituted phenyl, naphthyl, or heteroaryl;

and the enantiomers, diastereomers and pharmaceutically acceptable salts thereof.

6. The compound of claim 5 wherein the heteroaryl group is selected from the group consisting of pyridyl, furyl, thienyl and imidazolyl.

7. A compound of claim 1 selected from the group consisting of:

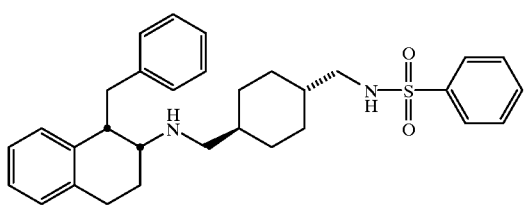

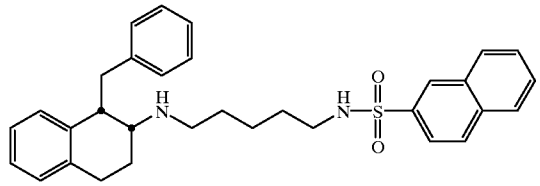

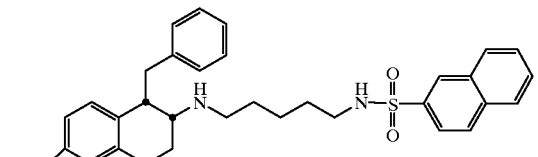

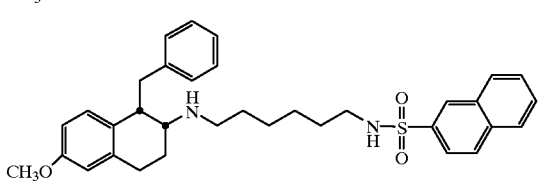

and

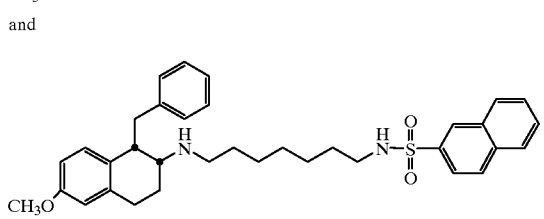

8. A compound of claim 1 selected from the group consisting of:

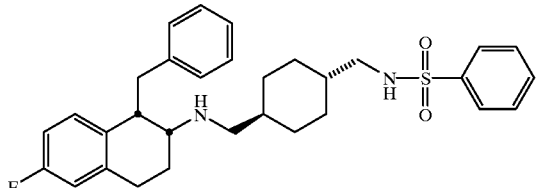

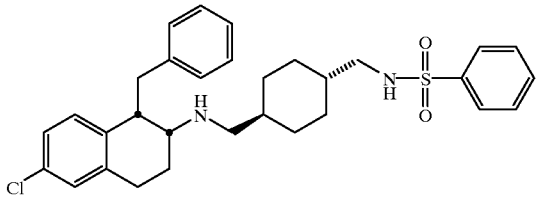

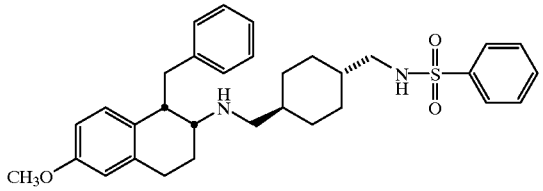

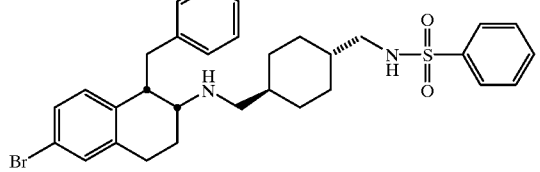

103
-continued
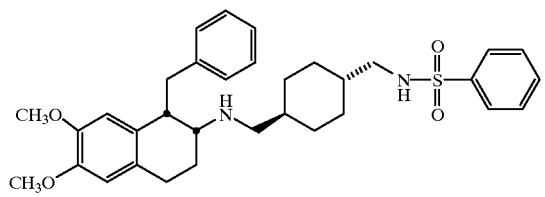
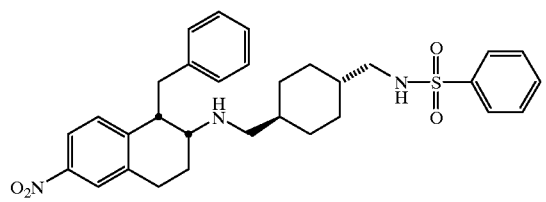
and
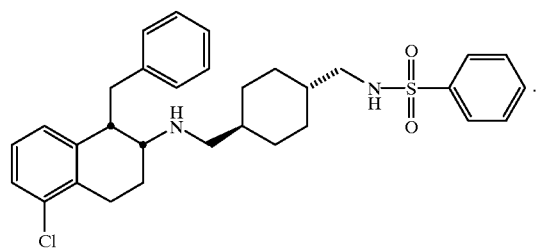
9. A compound of claim 1 selected from the group consisting of:
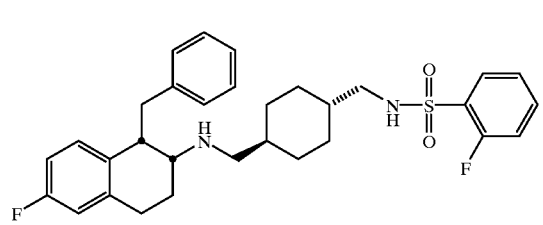
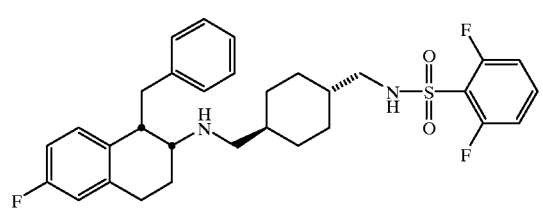
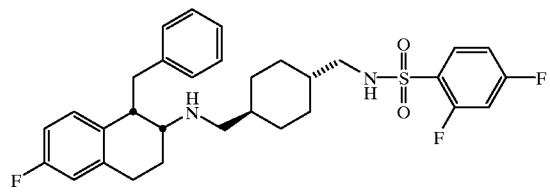
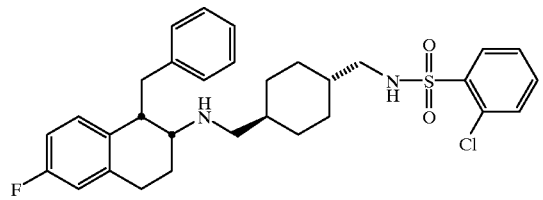
104
-continued
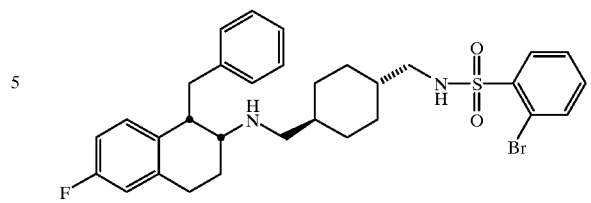
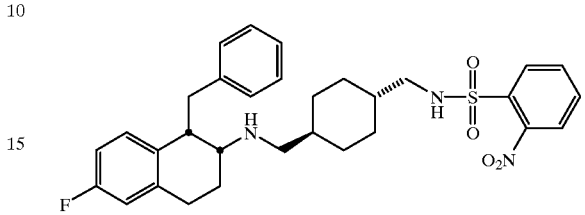
and
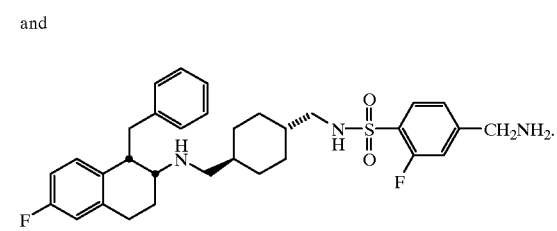
10. A compound of claim 1 selected from the group consisting of:
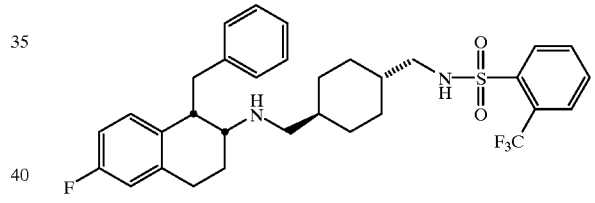
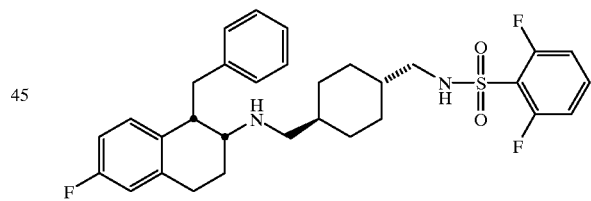
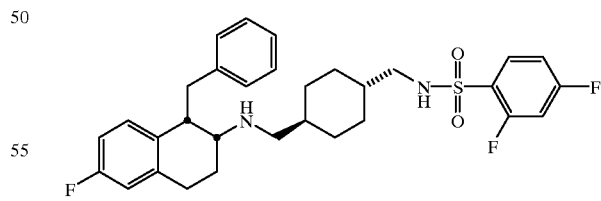
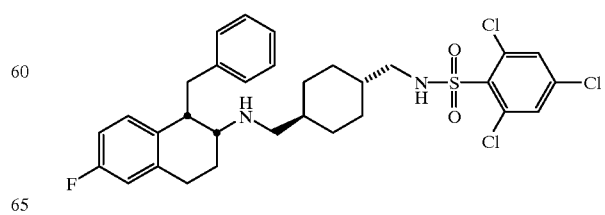

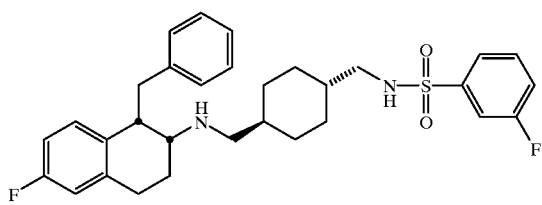
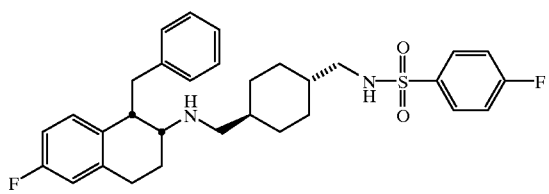
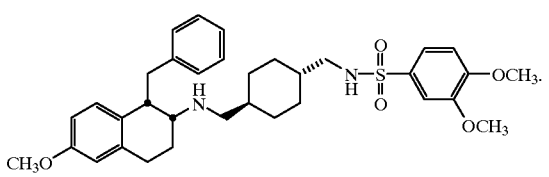
and
11. A compound of claim 1 selected from the group consisting of:
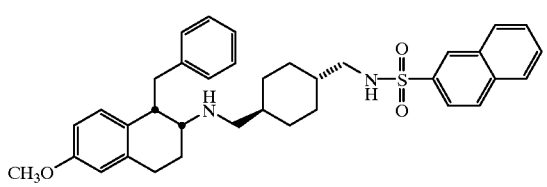
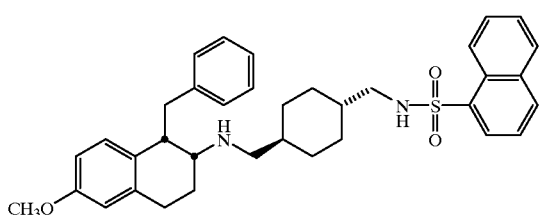
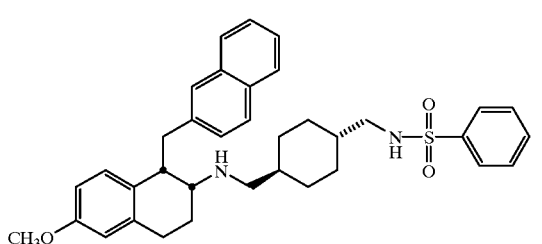
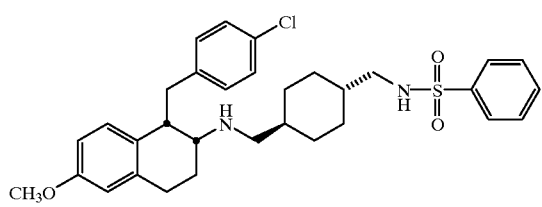
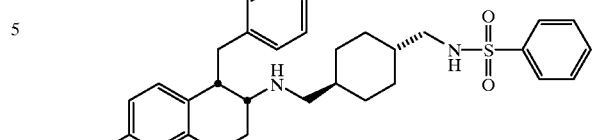
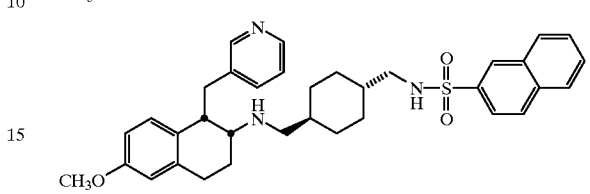
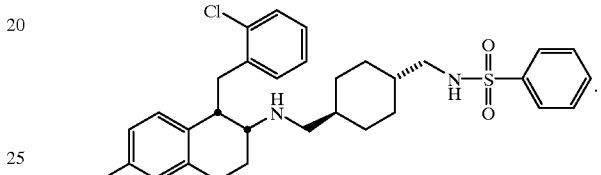
and
12. A compound of claim 1 selected from the group consisting of:
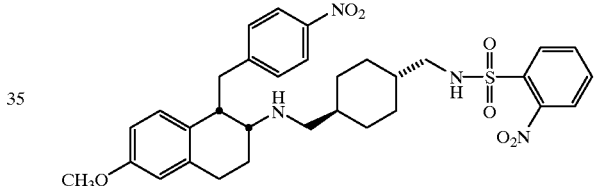
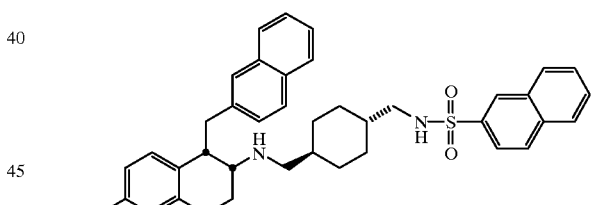
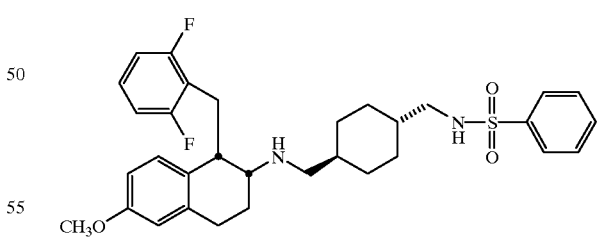
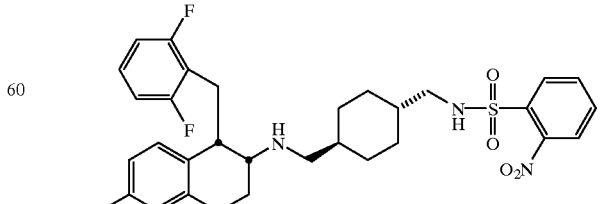

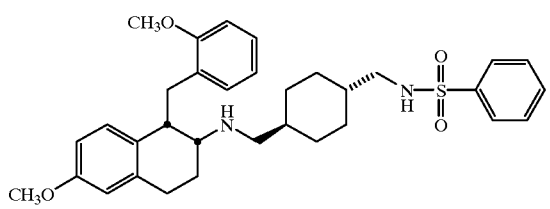
and
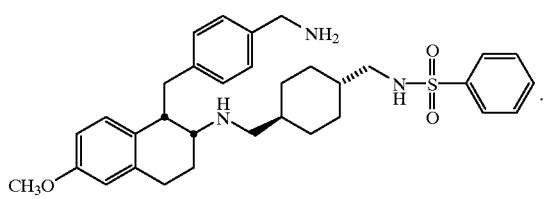
13. A compound of claim 1 selected from the group consisting of:
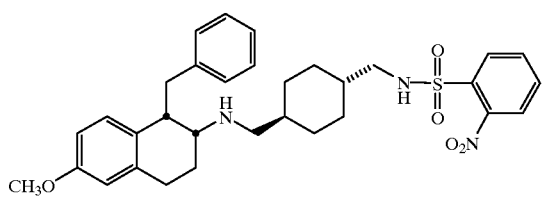
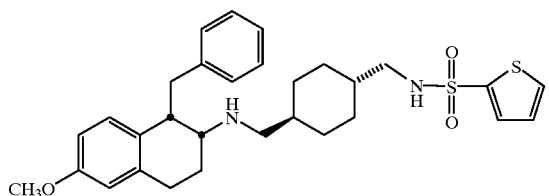
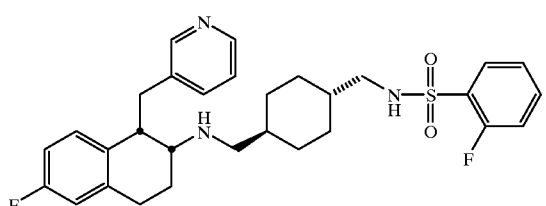
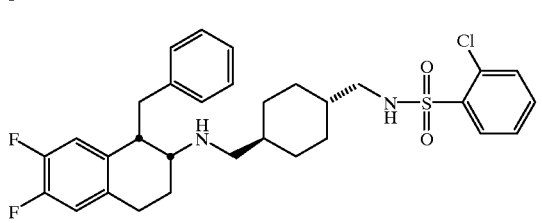
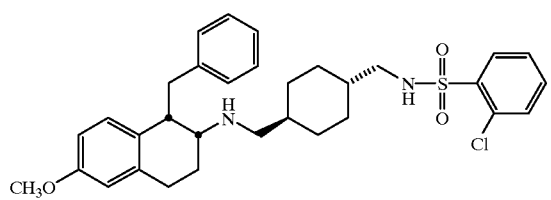
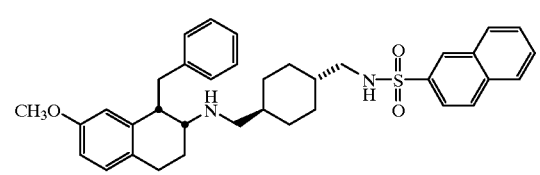
and
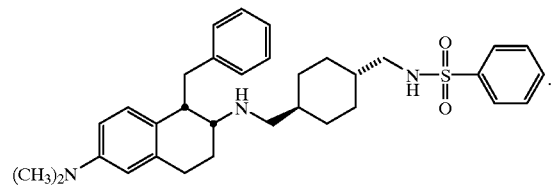
14. A compound of claim 1 selected from the group consisting of:
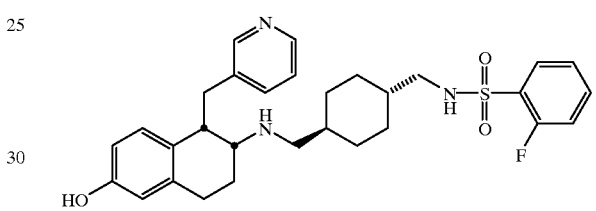
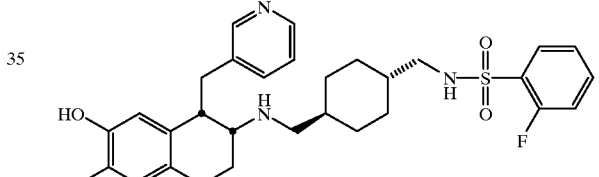
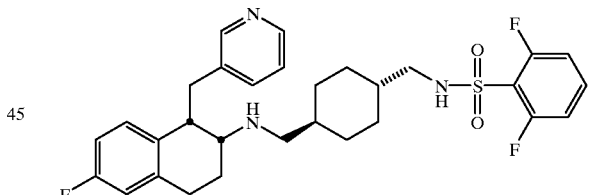
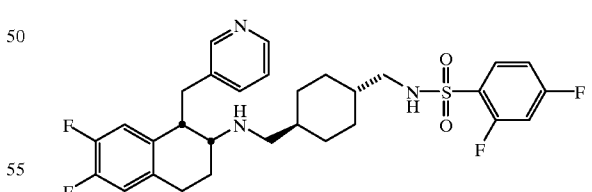

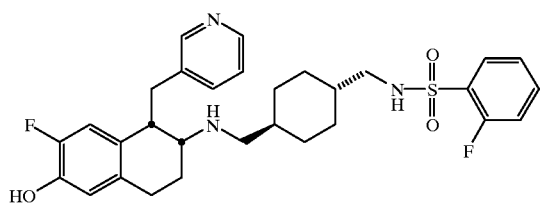
and
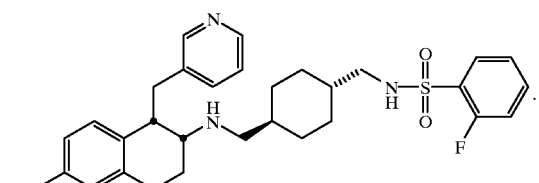
15. A compound of claim 1 selected from the group consisting of:
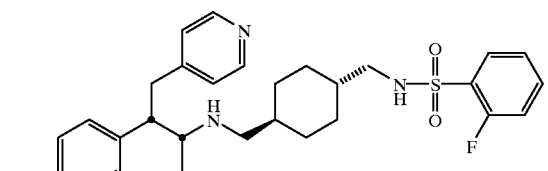
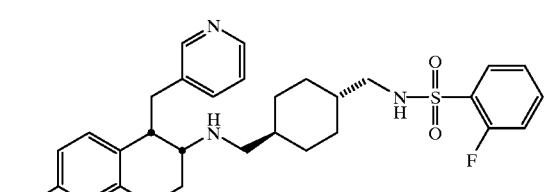
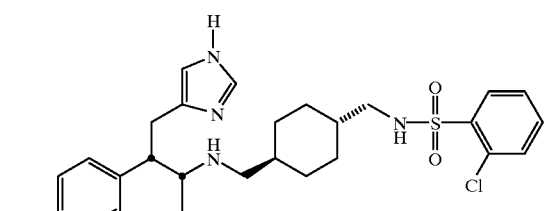
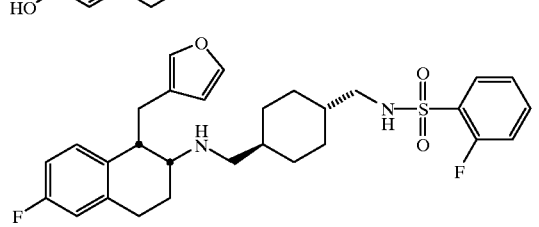
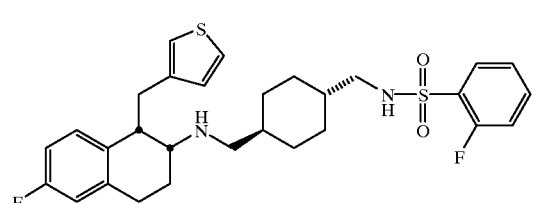
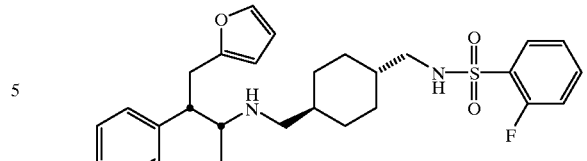
and
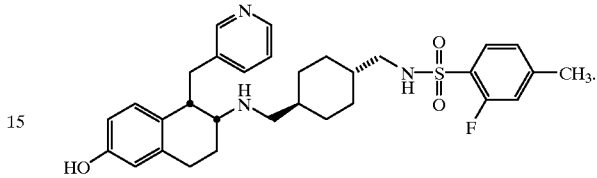
16. A compound of claim 1 selected from the group consisting of:
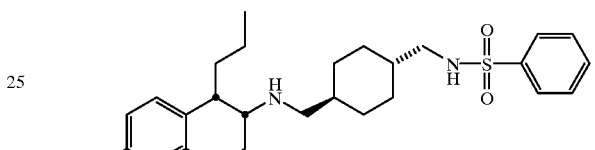
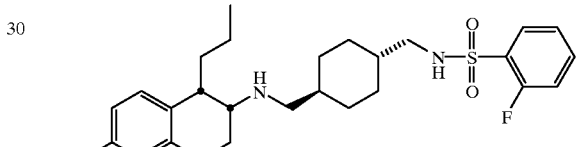
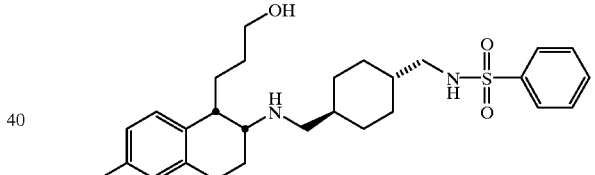
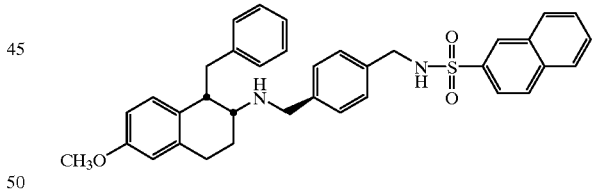
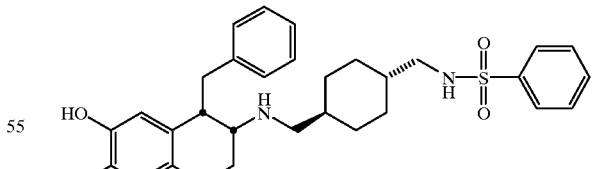
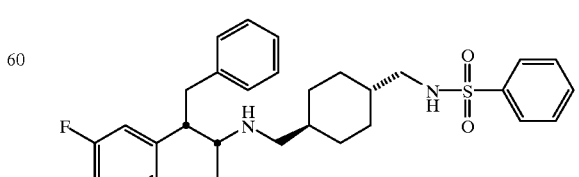

111
-continued
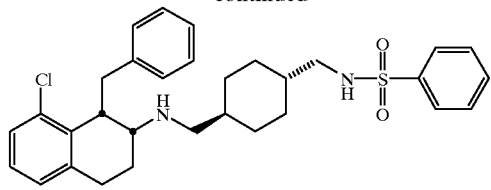
and
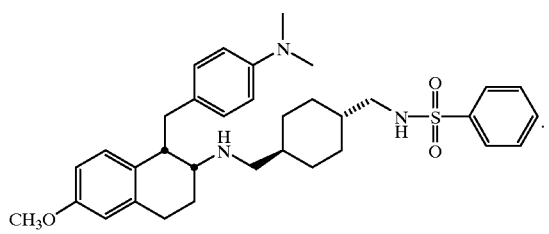
17. A compound of claim 1 selected from the group consisting of:
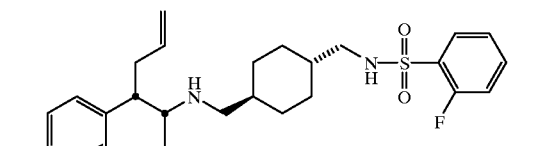
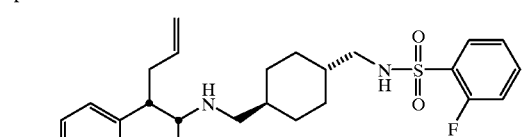
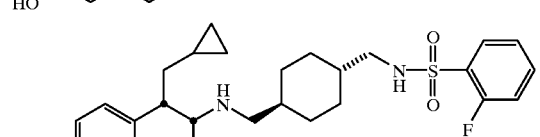
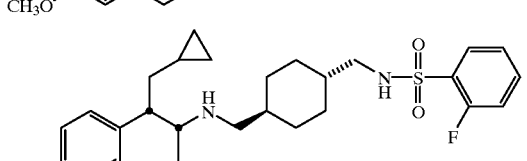
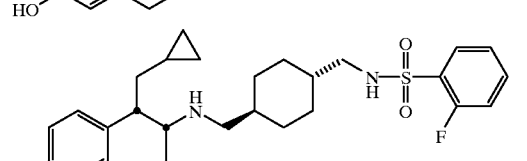
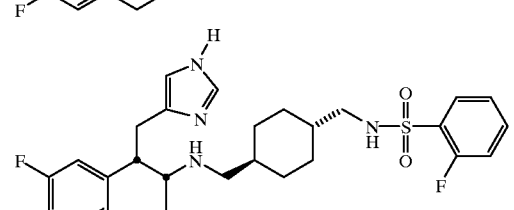
and
112
-continued
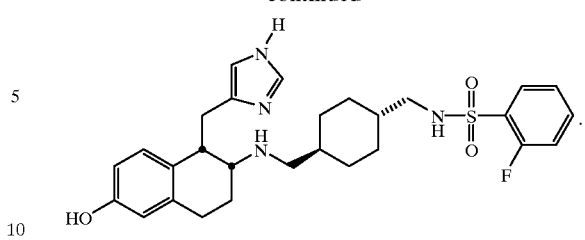
18. A compound of claim 1 selected from the group consisting of:
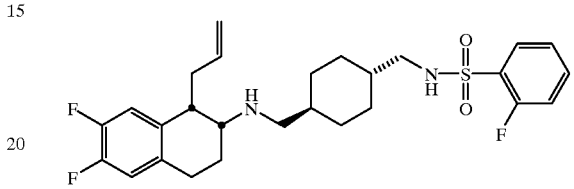
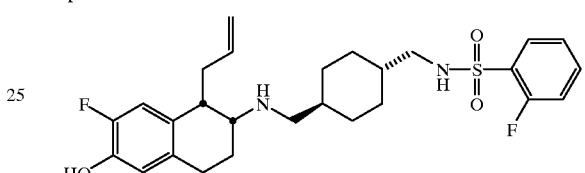
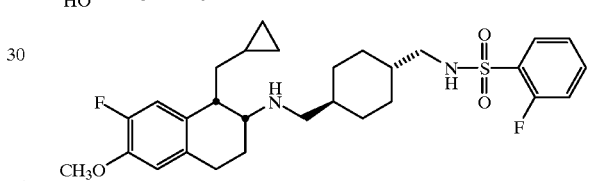
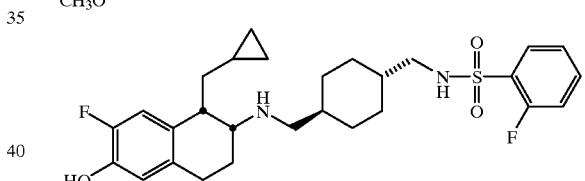
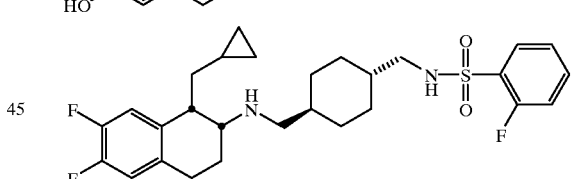
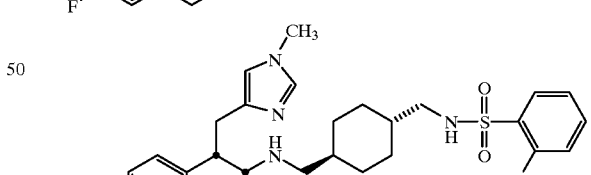
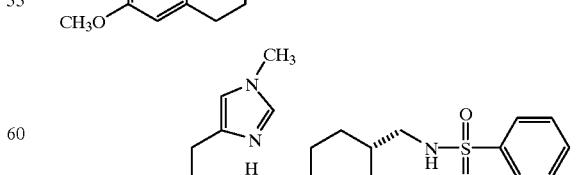
and -continued

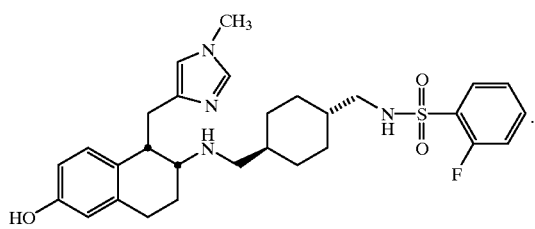

19. A compound selected from the group consisting of:

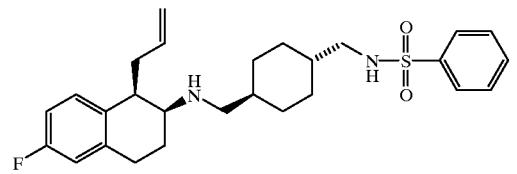

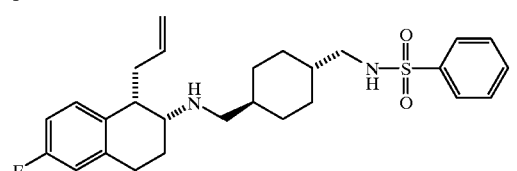

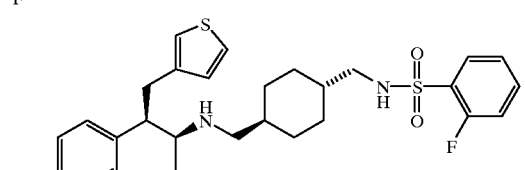

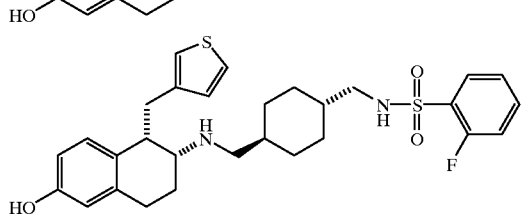

-continued

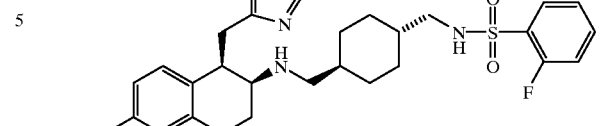

and

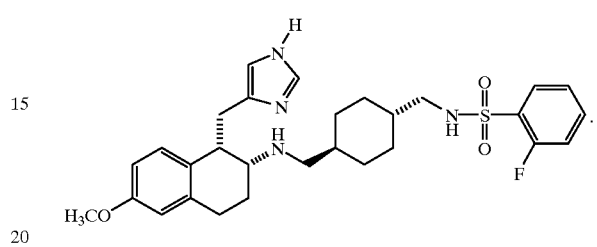

20. A method of treating disorders and diseases associated with neuropeptide receptor subtype 5 comprising administering to a mammal in need of such treatment a therapeutically effective amount of a compound of claim 1.

21. A pharmaceutical composition for the treatment of diseases or disorders associated with the neuropeptide Y5 receptor subtype 5 comprising a therapeutically effective amount of a compound of claim 1 and a pharmaceutically acceptable carrier.

22. A pharmaceutical composition for the treatment of disorders or disease states caused by eating disorders, obesity, bulimia nervosa, diabetes, dyspilipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea comprising a therapeutically effective amount of a compound of claim 1 and a pharmaceutically acceptable carrier.

* * * * *